US010533028B2

(12) United States Patent
Milstein et al.

(10) Patent No.: US 10,533,028 B2
(45) Date of Patent: Jan. 14, 2020

(54) RUTHENIUM COMPLEXES AND THEIR USES AS CATALYSTS IN PROCESSES FOR FORMATION AND/OR HYDROGENATION OF ESTERS, AMIDES AND RELATED REACTIONS

(71) Applicant: YEDA RESEARCH AND DEVELOPMENT CO. LTD., Rehovot (IL)

(72) Inventors: David Milstein, Rehovot (IL); Peng Hu, Rehovot (IL); Eran Fogler, Rehovot (IL); Jai Anand Garg Narayana Rao, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

(21) Appl. No.: 15/508,114

(22) PCT Filed: Sep. 3, 2015

(86) PCT No.: PCT/IL2015/050887
§ 371 (c)(1),
(2) Date: Mar. 2, 2017

(87) PCT Pub. No.: WO2016/035080
PCT Pub. Date: Mar. 10, 2016

(65) Prior Publication Data
US 2017/0283447 A1 Oct. 5, 2017

Related U.S. Application Data

(60) Provisional application No. 62/200,138, filed on Aug. 3, 2015.

(30) Foreign Application Priority Data

Sep. 4, 2014 (IL) .......................................... 234478

(51) Int. Cl.
*C07F 15/00* (2006.01)
*C07C 29/149* (2006.01)
(Continued)

(52) U.S. Cl.
CPC ........... *C07F 15/0046* (2013.01); *B01J 31/24* (2013.01); *B01J 31/2404* (2013.01); *C07C 29/149* (2013.01); *C07C 67/40* (2013.01); *C07C 213/00* (2013.01); *C07C 227/02* (2013.01); *C07C 231/08* (2013.01); *C07C 231/10* (2013.01); *C07C 249/02* (2013.01); *C07D 207/16* (2013.01); *C07D 241/08* (2013.01); *B01J 2231/641* (2013.01); *B01J 2231/763* (2013.01); *B01J 2531/0244* (2013.01); *B01J 2531/821* (2013.01); *C07C 2601/14* (2017.05)

(58) Field of Classification Search
CPC .................................................. C07F 15/0046
See application file for complete search history.

(56) References Cited

U.S. PATENT DOCUMENTS 4,356,321 A  10/1982  Hannam
4,788,289 A  11/1988  Su et al.
(Continued)

FOREIGN PATENT DOCUMENTS

CN  1569813 A  1/2005
CN  1820850 A  8/2006
(Continued)

OTHER PUBLICATIONS

Abbenhuis et al., "Ruthenium-Complex-Catalyzed N-(Cyclo)alkylation of Aromatic Amines with Diols. Selective Synthesis of N-(u)-Hydroxyalkyl)anilines of Type PhNH(CH2)nOH and of Some Bioactive Arylpiperazines," J. Org. Chem., 63:4282-4290 (1998).
Abdur-Rashid et al. "Catalytic Cycle for the asymmetric hydrogenation of prochiral ketones to chiral alcohols: Direct hydride and proton transfer from chiral catalysts trans-Ru (H) 2 (diphosphine)(diamine) to ketones and direct Addition of Dihydrogen to the Resulting Hydridoamido Complexes" Journal of the American Chemical Society. Aug. 1, 2001;123(30):7473-4.
Adair et al., "Oxidant-free oxidation: ruthenium catalysed dehydrogenation of alcohols," Tetrahedron Letters, 46(47):8233-8235 (2005).
Ahmad et al., "Complexes of Ruthenium, Osmium, Rhodium, and Iridium Containing Hydride Carbonyl, or Nitrosyl Ligands," Inorganic Syntheses, John Wiley & Sons, Inc., Hoboken, NJ, USA, vol. 15, pp. 45-64 (1974).
(Continued)

*Primary Examiner* — Joseph R Kosack
(74) *Attorney, Agent, or Firm* — Mark S. Cohen; Pearl Cohen Zedek Latzer Baratz LLP

(57) ABSTRACT

The present invention relates to novel Ruthenium complexes of formulae A1-A4 and their use, inter alia, for (1) dehydrogenative coupling of alcohols to esters; (2) hydrogenation of esters to alcohols (including hydrogenation of cyclic esters (lactones) or cyclic di-esters (di-lactones), or polyesters); (3) preparing amides from alcohols and amines—(including the preparation of polyamides (e.g., polypeptides) by reacting dialcohols and diamines and/or polymerization of amino alcohols and/or forming cyclic dipeptides from p-aminoalcohols; (4) hydrogenation of amides (including cyclic dipeptides, polypeptides and polyamides) to alcohols and amines; (5) hydrogenation of organic carbonates (including polycarbonates) to alcohols or hydrogenation of carbamates (including polycarbamates) or urea derivatives to alcohols and amines; (6) dehydrogenation of secondary alcohols to ketones; (7) amidation of esters (i.e., synthesis of amides from esters and amines); (8) acylation of alcohols using esters; (9) coupling of alcohols with water and a base to form carboxylic acids; and (10) preparation of amino acids or their salts by coupling of amino alcohols with water and a base. The present, invention further relates to the use of certain known Ruthenium complexes for the preparation of amino acids or their salts from amino alcohols.

42 Claims, 7 Drawing Sheets

(51) Int. Cl.

| | |
|---|---|
| C07C 213/00 | (2006.01) |
| C07C 227/02 | (2006.01) |
| C07C 231/08 | (2006.01) |
| C07C 231/10 | (2006.01) |
| B01J 31/24 | (2006.01) |
| C07C 67/40 | (2006.01) |
| C07C 249/02 | (2006.01) |
| C07D 207/16 | (2006.01) |
| C07D 241/08 | (2006.01) |

(56) References Cited

U.S. PATENT DOCUMENTS

| | | |
|---|---|---|
| 4,855,431 A | 8/1989 | Chang et al. |
| 6,074,447 A | 6/2000 | Jensen |
| 7,709,689 B2 | 5/2010 | Kilner et al. |
| 8,178,723 B2 | 5/2012 | Milstein et al. |
| 9,738,685 B2 | 8/2017 | Milstein et al. |
| 2005/0274440 A1 | 12/2005 | Tomiyama |
| 2009/0112005 A1 | 4/2009 | Milstein et al. |
| 2011/0042227 A1 | 2/2011 | Corbea |
| 2012/0253042 A1 | 10/2012 | Milstein |
| 2014/0134100 A1 | 5/2014 | Naeemi et al. |

FOREIGN PATENT DOCUMENTS

| | | |
|---|---|---|
| CN | 1859330 A | 10/2006 |
| CN | 101587779 B | 1/2011 |
| CN | 102010447 A | 4/2011 |
| CN | 102030657 A | 4/2011 |
| CN | 101602015 B | 9/2011 |
| CN | 102600888 A | 7/2012 |
| CN | 101961661 B | 8/2012 |
| CN | 202356105 U | 8/2012 |
| CN | 102690162 A | 9/2012 |
| CN | 102489315 B | 9/2013 |
| CN | 103420796 A | 12/2013 |
| EP | 0286280 A1 | 10/1988 |
| EP | 1475349 A2 | 10/2004 |
| EP | 2161251 | 3/2010 |
| JP | 2003-146966 A | 5/2003 |
| JP | 2004-345964 A | 12/2004 |
| JP | 2006-63050 A | 3/2006 |
| JP | 2008-285454 A | 11/2008 |
| JP | 2010-63986 A | 3/2010 |
| WO | WO 2003/093208 A1 | 11/2003 |
| WO | WO 2008/035123 A2 | 3/2008 |
| WO | WO 2010/018570 A1 | 2/2010 |
| WO | WO 2012/052996 A2 | 4/2012 |

OTHER PUBLICATIONS

Alberico et al. "Selective hydrogen production from methanol with a defined iron pincer catalyst under mild conditions" Angewandte Chemie International Edition, Dec. 23, 2013;52(52):14162-6.
Albrecht et al., "Platinum Group Organometallics Based on 'Pincer' Complexes: Sensors, Switches, and Catalysts," Angew. Chem. Int. Ed., 40(20):3750-3781 (2001).
Armarego et al. "Purification of Laboratory Chemicals" (4TH) Butterworth-Heinemann . New York. 1996.
Balaraman et al., "Direct Hydrogenation of Amides to Alcohols and Amines under Mild Conditions," J. Am. Chem. Soc., 132(47): 16756-16758 (2010).
Balaraman et al., "Unprecedented Catalytic Hydrogenation of Urea Derivatives to Amines and Methanol," Angewandte Chemie, International Edition 50(49): 11702-11705 (2011), and supporting information S11702/1-S11702/7.
Balaraman et al., "Efficient hydrogenation of organic carbonates, carbamates and formates indicates alternative routes to methanol based on C02 and CO," Nature Chemistry, 3(8):609-614 (2011).
Balaraman et al. "Direct Synthesis of Secondary Amines From Alcohols and Ammonia Catalyzed by a Ruthenium Pincer Complex" Catalysis Letters. Jan. 1, 2015:145(1):139-44.
Balaraman et al. "Efficient hydrogenation of biomass-derived cyclic di-esters to 1, 2-diols" Chemical Communications. 2012;48(8):1111-3.
Balaraman et al. Catalytic transformation of alcohols to carboxylic acid salts and H2 using water as the oxygen atom source. Nature Chemistry. Feb. 1, 2013;5(2):122-5.
Barrios-Francisco et al., "PNN Ruthenium Pincer Complexes Based on Phosphinated 2,2,-Dipyridinemethane and 2,2,-Oxobispyridine, Metal-Ligand Cooperation in Cyclometalation and Catalysis," Organometallics 32(10):2973-2982 (2013).
Beamson et al., "Selective hydrogenation of amides using Rh/Mo catalysts," Journal of Catalysis, 269(1):93-102 (2010).
Beamson et al., "Selective Hydrogenation of Amides using Ruthenium/ Molybdenum Catalysts," Adv. Synth. Catal., 352{5):869-883 (2010).
Ben-Ari et al., "Metal-Ligand Cooperation in C-H and H2 Activation by an Electron-Rich PNP Ir{I) System: Facile Ligand Dearomatization-Aromatization as Key Steps," J. Am. Chem. Soc., 128:15390-15391 (2006).
Benet-Buchholz et al., "Iron vs. ruthenium—a comparison of the stereoselectivity in catalytic olefin epoxidation," Dalton Transactions, {30):5910-5923 (2009).
Benet-Buchholz et al., "The RuIV=0-catalyzed sulfoxidation: a gated mechanism where O to S linkage isomerization switches between different efficiencies," Dalton Transactions, 39{13):3315-3320 (2010).
Blum et al., "Catalytically reactive (rl4-tetracyclone)(CO)2{H)2Ru and related complexes in dehydrogenation of alcohols to esters," Journal of Organometallic Chemistry, 282(1):C7-C10 (1985).
Boelrijk et al., "Oxidation of octyl a-D-glucopyranoside to octyl a-D-glucuronic acid, catalyzed by several ruthenium complexes, containing a 2-(phenyl)azopyridine or a 2-(nitrophenyl)azopyridine ligand," Journal of Molecular Catalysis A: Chemical, 103(2):73-85 (1995).
Bonnet et al., "Lanthanide mono(borohydride) complexes of diamide-diamine donor ligands: novel single site catalysts for the polymerisation of methyl methacrylate," Dalton Trans., 7(3):421-423 (2005).
Bray, "Large-scale manufacture of peptide therapeutics by chemical synthesis," Nature Reviews, 2(7):587-593 (2003).
Bunton et al. "Source of catalysis of dephosphorylation of p-nitrophenyldiphenylphosphate by metallomicelles", J. Chem. Soc., Perkin Trans. 2, 1996, 419-425.
Cantillo, "Mechanistic Insights on the Ruthenium-Catalyzed Hydrogenation of Amides—C—N vs. C-0 Cleavage," Eur. J. Inorg. Chem., 2011(19):3008-3013 (2011).
Cassidy et al., "Practical Synthesis of Amides from In Situ Generated Copper(I) Acetylides and Sulfonyl Azides," Angew. Chem. Int. Ed., 45(19):3154-3157 (2006).
Catalano et al., "Steric Modulation of Electrocatalytic Benzyl Alcohol Oxidation by [Ru(trpy)(R2dppi)(0)]2+ Complexes," Inorganic Chemistry, 37(9):2150-2157 (1998).
Catalano et al., "Synthesis, characterization, and electrocatalytic oxidation of benzyl alcohol by a pair of geometric isomers of [Ru{trpy){4,4•-Me2dppi)(OH2)]2+ where 4,4•-dppi is 3,6-di-(4-methylpyrid-2-yl)pyridazine," Polyhedron, 19{9):1049-1055 (2000).
Chaignaud et al., "New highlights in the synthesis and reactivity of 1,4-dihydropyrazine derivatives," Tetrahedron, 64(35):8059-8066 (2008).
Chan et al., "Oxidative Amide Synthesis and N-Terminal a-Amino Group Ligation of Peptides in Aqueous Medium," J. Am. Chem. Soc., 128(46): 14796-14797 (2006).
Chanda et al., "Ruthenium monoterpyridine complexes incorporating a,a•-diimine based ancillary functions. Synthesis, crystal structure, spectroelectrochemical properties and catalytic aspect," Polyhedron, 21(20):2033-2043 (2002).
Chardon-Noblat et al., "Electrosynthesis, physico-chemical and electrocatalytic properties of a novel electroactive Ru(0) material based on the (Ru(terpy)(CO)) frame (terpy-2,2':6',2"-terpyridine)," Journal of Electroanalytical Chemistry, 529:135-144 (2002).
Chatterjee et al., "Kinetics and catalysis of oxidation of phenol by ruthenium(IV)-oxo complex," Journal of Molecular Catalysis A: Chemical, 282(1-2):124-128 (2008).
Chatterjee et al., "Oxidation of catechol and L-ascorbic acid by [RuIII(tpy)(pic)(OH)]+ (tpy=2,22,•6•"-terpyridine; pic-=

(56) References Cited

OTHER PUBLICATIONS picolinate): Kinetic and mechanistic studies," Inorganic Chemistry Communications, 9(12):1219-1222 (2006).
Chatterjee et al., "Synthesis, characterization and reactivity of a novel ruthenium(II) complex containing polypyridyl ligand," Polyhedron, 26(1)176-183 (2007).
Chen et al., "Homogeneous Photocatalytic Oxidation of Alcohols by a Chromophore-Catalyst Dyad of Ruthenium Complexes," Angew. Chem. Int. Ed., 48(51 ):9672-9675 (2009).
Cho et al., "Copper-Catalyzed Hydrative Amide Synthesis with Terminal Alkyne, Sulfonyl Azide, and Water," J. Am, Chem. Sec., 127(46)16046-16047 (2005).
Cho et al. "Hydrogen Sortption in Hcl-Treated Polyaniline and Polypyrrole; New Potential Hydrogen Storage Media", Fuel Chemistry Division Preprints 2002, 47(2), 790.
Claustro et al., "Synthesis, spectroscopic and electrochemical properties of ruthenium-2-(2•-hydroxyphenyl)-benzoxazole complexes. Crystal structure of [Ru(terpy)(HPB)Cl]," Inorganica Chimica Acta, 342: 29-36 (2003).
Cobley et al., "Platinum catalysed hydrolytic amidation of unactivated nitriles," Tetrahedron Letters, 41(14):2467-2470 (2000).
Concepcion et al., One Site is Enough. Catalytic Water Oxidation by [Ru{tpy}{bpm)(OH2)]2+ and [Ru(tpy)(bpz)(OH2)]2+, Journal of the American Chemical Society, 130(49):16462-16463 (2008).
Concepcion et al., "Catalytic and Surface-Electrocatalytic Water Oxidation by Redox Mediator-Catalyst Assemblies," Angew. Chem., Int. Ed., 48 (50):9473-9476 (2009), and supporting information S9473/1-S9473/11.
Concepcion et al., "Catalytic Water Oxidation by Single-Site Ruthenium Catalysts," Inorganic Chemistry, 49(4): 1277-1279 (2010).
Concepcion et al., "Mechanism of Water Oxidation by Single-Site Ruthenium Complex Catalysts," Journal of the American Chemical Society, 132(5):1545-1557 (2010).
Crochet et al. "Ruthenium-catalyzed amide-bond formation" In Ruthenium in Catalysis 2014 (pp. 81-118). Springer International Publishing.
Cui et al. "N, N-Dimethyl-β-alanine as an inexpensive and efficient ligand for palladium-catalyzed Heck reaction" Organic letters. Jun. 8, 2006;8(12):2467-70.
Dakkach et al., "New Ru(II) Complexes with Anionic and Neutral N-Conor Ligands as Epoxidation Catalysts: An Evaluation of Geometrical and Electronic Effects," Inorganic Chemistry, 49(15):7072-7079 (2010).
Das et al., "Zinc-Catalyzed Reduction of Amides: Unprecedented Selectivity and Functional Group Tolerance," J. Am. Chem. Soc., 132(6):1770-1771 (2010).
Diao et al., "Studies on ruthenium catalyst with a ligand of copolymer and its performance in catalytic hydrogenation," Huaxue Tongbao, (12):34-37 (2000). Translated abstract.
Dick et al. "Novel bis ((trimethylsilyl) benzamidinato) titanium (III) complexes. Preparation and crystal structures of {PhC [(Me3Si) N] 2} 2Ti (. mu.-Cl) 2Li (TMEDA),{PhC [(Me3Si) N] 2} 2Ti (BH4), and {PhC [(Me3Si) N] 2} 2Ti (. eta. 3-allyl)" Inorganic Chemistry. May 1993;32(10)1959-62.
Dobson et al., "Complexes of the Platinum Metals. 7. Homogeneous Ruthenium and Osmium Catalysts for the Dehydrogenation of Primary and Secondary Alcohols," Inorganic Chemistry, 16(1 ):137-142 (1977).
Duan et al., "Isolated Seven-Coordinate Ru(IV) Dimer Complex with [HOHOH](−) Bridging Ligand as an Intermediate for Catalytic Water Oxidation," Journal of the American Chemical Society, 131 (30):10397-10399 (2009).
Fernandes et al., "Reduction of amides with silanes catalyzed by M002Cl2," Journal of Molecular Catalysis A: Chemical; 272(1-2):60-63 (2007).
Fogler et al., "New CNN-Type Ruthenium Pincer NHC Complexes. Mild, Efficient Catalytic Hydrogenation of Esters," Organometallics, 30(14):3826-3833 (2011).

Fogler et al. "System with potential dual modes of metal-ligand cooperation: highly catalytically active pyridine-based PNNH-Ru pincer complexes", Chemistry. Nov. 24, 2014;20(48):15727-31.
Francas et al., "A Ru-Hbpp-Based Water-Oxidation Catalyst Anchored on Rutile Ti02," ChemSusChem, 2(4):321-329 (2009).
Fujita et al., "Synthesis of Five-, Six-, and Seven-Membered Ring Lactams by Cp*Rh Complex-Catalyzed Oxidative N-Heterocyclization of Amino Alcohols," Organic Letters, 6(16):2785-2788 (2004).
Fustero et al. "A new and expeditious strategy for the synthesis of β-amino acids from Δ 2-oxazolines" Tetrahedron. Jan. 21, 2001;57(4):703-12.
Gargir et al. "PNS-Type ruthenium pincer complexes" Organometallics. Aug. 27, 2012;31(17):6207-14.
Gellrich et al. "Mechanistic Investigations of the Catalytic Formation of Lactams from Amines and Water with Liberation of H2" Journal of the American Chemical Society. Apr. 6, 2015;137(14):4851-9.
Ghosh et al., "Direct Amide Synthesis from Alcohols and Amines by Phosphine-Free Ruthenium Catalyst Systems," Adv. Synth. Catal., 351(16):2643-2649 (2009).
Gibson et al., "Synthesis and Characterization of Ruthenium(II) Hydrido and Hydroxo Complexes Bearing the 2,6-Bis (di-tert-butylphosphinomethyl)pyridine Ligand," Organometallics, 23(10):2510-2513 (2004).
Gnanaprakasam et al., "Synthesis of Peptides and Pyrazines from P-Amino Alcohols through Extrusion of H2 Catalyzed by Ruthenium Pincer Complexes: Ligand-Controlled Selectivity," Angew. Chem., Int. Ed., 50{51 ):12240-12244 (2011), and supporting information S12240/1-S12240/9.
Gnanaprakasam et al., "Direct Synthesis of Imines from Alcohols and Amines with Liberation of H2," Angew. Chem. Int. Ed., 49(8):1468-1471 (2010).
Gnanaprakasam et al., "Ruthenium Pincer-Catalyzed Acylation of Alcohols Using Esters with Liberation of Hydrogen under Neutral Conditions," Advanced Synthesis and Catalysis, 352(18):3169-3173 (2010).
Gnanaprakasam et al. "Synthesis of amides from esters and amines with liberation of H2 under neutral conditions" Journal of the American Chemical Society. Jan. 19, 2011;133(6):1682-5.
Gunanathan et al., "Direct Synthesis of Amides from Alcohols and Amines with Liberation of H2," Science, 317 (5839):790-792 (2007).
Gunanathan et al., "Selective Synthesis of Primary Amines Directly from Alcohols and Ammonia," Angew. Chem. Int. Ed., 47(45):8661-8664 (2008).
Gunanathan et al., "Direct Conversion of Alcohols to Acetals and H2 Catalyzed by an Acridine-Based Ruthenium Pincer Complex," J. Am. Chem. Soc., 131(9):3146-3147 (2009).
Gunanathan et al., "Bond Activation by Metal-Ligand Cooperation: Design of 'Green' Catalytic Reactions Based on Aromatization-Dearomatization of Pincer Complexes," Topics in Organometallic Chemistry, 37:55-84 (2011).
Gunanathan et al., "Metal-Ligand Cooperation by Aromatization-Dearomatization: A New Paradigm in Bond Activation and 'Green' Catalysis," Accounts of Chemical Research, 44{8):588-602 (2011).
Gunanathan et al., "Reduction of Nitriles to Amines with H2 Catalyzed by Nonclassical Ruthenium Hydrides—Water-Promoted Selectivity for Primary Amines and Mechanistic Investigations," European Journal of Inorganic Chemistry, 2011(22):3381-3386 (2011).
Guo et al., "Applications of Ruthenium Hydride Borohydride Complexes Containing Phosphinite and Diamine Ligands to Asymmetric Catalytic Reactions," Organic Letters, 7(9): 1757-1759 (2005).
Haniti et al., "Ruthenium catalysed N-alkylation of amines with alcohols," Chem., Commun., (7):725-727 (2007).
Hino et al., "Redox Behavior of New Ru-Dioxolene-Ammine Complexes and Catalytic Activity toward Electrochemical Oxidation of Alcohol under Mild Conditions," Chemistry Letters 33(12):1596-1597 (2004).
Hirosawa et al., "Hydrogenation of Amides by the Use of Bimetallic Catalysts Consisting of Group 8 to 10, and Group 6 or 7 Metals," Tetrahedron Letters, 37(37):6749-6752 (1996).

(56) References Cited

OTHER PUBLICATIONS

Ho et al., "Double-helical ruthenium complexes of 2,2': 6,,2''',2'''6'',2''''-quinquepyridine (qpy) for multi-electron oxidation reactions," Chemical Communications, (10):1197-1198 (1996).

Hu et al. "Rechargeable hydrogen storage system based on the dehydrogenative coupling of ethylenediamine with ethanol" Angewandte Chemie. Jan. 18, 2016;128(3):1073-6.

Hu et al. "Reusable Homogeneous Catalytic System for Hydrogen Production from Methanol and Waters" ACS Catal. 2014, 4, 2649-2652.

Huang et al., "A novel method to immobilize Ru nanoparticles on SBA-15 firmly by ionic liquid and hydrogenation of arene," Catalysis Letters, 103(1-2):59-62 (2005).

Huff et al., "Cascade Catalysis for the Homogeneous Hydrogenation of C02 to Methanol," Journal of the American Chemical Society, 133(45): 18122-18125 (2011).

International Search Report for PCT Application No. PCT/IL2015/050887 dated Feb. 23, 2016.

Ito et al., "Selective Dimerization of Aldehydes to Esters Catalyzed by Hydridoruthenium Complexes," Bull. Chem. Soc. Jpn., 55(2):504-512 (1982).

Ito et al., "Hydrogenation of N-Acylcarbamates and N-Acylsulfonamides Catalyzed by a Bifunctional [Cp*Ru(PN)] Complex," Angew. Chem. Int. Ed., 48(7): 1324-1327 (2009).

Jansen et al., "Synthesis of Hemilabile P,N Ligands: w-2-Pyridyl-n-alkylphosphines," Monatshefte fur Chemie, 130(6):783-794 (1999).

Jensen et al., "Transition Metal Tetrahydridoborates as Models of Methane Activation: Synthesis and Structure of Ti(BH4)3(PMe3)2," J. Chem. Soc., Chem. Commun., 15:1160-1162 (1986).

Jensen et al., "Titanium(III) Tetrahydroborates. Preparation and Crystal Structure of Ti(BH4)3(PMe3)2 Containing an Unusual Ti—H—B Agostic Interaction," J. Am. Chem. Soc., 110(15):4977-4982 (1988).

Jia et al., "Synthesis, Characterization, and Acidity Properties of [MCI(H2)(L)(PMP)]BF4 (M=Ru, L=PPh3, CO; M=Os, L=PPh3; PMP=2,6-(Ph2PCH2)2C5H3N)," Organometallics, 16:3941-3949 (1997).

Jung et al., "Dehydrogenation of Alcohols and Hydrogenation of Aldehydes Using Homogeneous Ruthenium Catalysts," Organometallics, 1(4):658-666 (1982).

Kelson et al., "Synthesis and structure of a ruthenium(II) complex incorporating kN bound 2-pyridonato ligands; a new catalytic system for transfer hydrogenation of ketones," J. Chem. Soc., Dalton Trans., (22):4023-4024 (2000).

Khusnutdinova et al. "Oxidant-Free Conversion of Cyclic Amines to Lactams and H2 Using Water As the Oxygen Atom Source" Journal of the American Chemical Society. Feb. 18, 2014;136(8):2998-3001.

Kohl et al., "Consecutive Thermal H2 and Light-Induced 02 Evolution from Water Promoted by a Metal Complex," Science, 324(5923):74-77 (2009).

Langer et al., "Stepwise Metal-Ligand Cooperation by a Reversible Aromatization/Deconjugation Sequence in Ruthenium Complexes with a Tetradentate Phenanthroline-Based Ligand," Chem. Eur. J., 19{10):3407-3414 (2013).

Langer et al, "Low-Pressure Hydrogenation of Carbon Dioxide Catalyzed by an Iron Pincer Complex Exhibiting Noble Metal Activity" Angewandte Chemie International Edition. Oct. 10, 2011;50(42):9948-52.

Langer et al. "Efficient hydrogenation of ketones catalyzed by an iron pincer complex" Angewandte Chemie. Feb. 25, 2011;123(9)2168-72.

Lee et at, "Hydroboration of Alkenes and Alkynes with Sodium Borohydride Catalyzed by Titanium Complex," Chemistry Letters, 13{3):363-366 (1984).

Lee et al., "Regio- and Stereo-Selectivities in the Titanium Complex Catalyzed Hydroboration of Carbon-Carbon Double Bonds in Various Unsaturated Compounds," Chemistry Letters, 13(5):673-676 (1984).

Letts et al., "The Synthesis, Characterization, and Reactivity of an Unusual, Amphoteric (Tetrahydroborato)ruthenium Hydride Complex of a Chelating Triphosphine, Ru(H){n2-BH4)(ttp)," J. Am. Chem. Soc., 104(14):3898-3905 (1982).

Leung et al. "Transitioning enantioselective indicator displacement assays for α-amino acids to protocols amenable to high-throughput screening" Journal of the American Chemical Society. Aug. 21, 2008;130(37):12328-33.

Liao et al., "Hydrophilicity Modification of MCM-41 with Zirconia and Supported Ruthenium-Lanthanum for Benzene Hydrogenation to Cyclohexene," Synthesis and Reactivity in Inorganic, Metal-Organic and Nano-Metal Chemistry, 43(9):1206-1211 (2013).

Liao et al., "Benzene hydrogenation over oxide-modified MCM-41 supported ruthenium-lanthanum catalyst: The influence of zirconia crystal form and surface hydrophilicity," Chemical Engineering Journal, 243:207-216 (2014).

Ligthart et al., "Highly sustainable catalytic dehydrogenation of alcohols with evolution of hydrogen gas," Tetrahedron Letters, 44(7): 1507-1509 (2003).

Lin et al., "A convenient lactonization of diols to γ- and δ-lactones catalysed by transition metal polyhydrides," Journal of Organometallic Chemistry, 429(2):269-274 (1992).

Liu et al., "Synthesis of PVP-stabilized Pt/Ru colloidal nanoparticles by ethanol reduction and their catalytic properties for selective hydrogenation of ortho-chloronitrobenzene," Journal of Catalysis, 278(1 )1-7 (2011).

Liu et al. "Enhanced reduction of C—N multiple bonds using sodium borohydride and an amorphous nickel catalyst" Organic & biomolecular chemistry. 2012;10(3):663-70.

Livanov et al. "Photocatalytic Splitting of CS2 to S8 and a Carbon-Sulfur Polymer Catalyzed by a Bimetallic Ruthenium (II) Compound with a Tertiary Amine Binding Site: Toward Photocatalytic Splitting of C02?," Inorganic Chemistry, 50(22): 11273-11275 (2011).

Lowe et al. "Amino acids bearing nucleobases for the synthesis of novel peptidenucleic acids" Journal of the Chemical Society, Perkin Transactions 1. Jan. 1, 1997(4):539-46.

Maegawa et al. "Efficient and practical arene hydrogenation by heterogeneous catalysts Under mild conditions" Chemistry—A European Journal. Jul. 13, 2009;15(28):6953-63.

Masaoka et al., "Clear Evidence Showing the Robustness of a Highly Active Oxygen-evolving Mononuclear Ruthenium Complex with an Aqua Ligand," Chemistry Letters 38(2):182-183 (2009).

Masotti et al. "Novel Tween® 20 derivatives enable the formation of efficient pH-sensitive drug delivery vehicles for human hepatoblastoma" Bioorganic & medicinal chemistry letters. May 15, 2010;20(10):3021-5.

Menashe et al., "Catalytic Disproportionation of Aldehydes with Ruthenium Complexes," Organometallics, 10(11 ):3885-3891 (1991).

Miao et al., "Ru Nanoparticles Immobilized on Montmorillonite by Ionic Liquids: A Highly Efficient Heterogeneous Catalyst for the Hydrogenation of Benzene," Angew. Chem. Int. Ed., 45(2):266-269 (2005).

Milstein "Catalysis—The Key to Green Chemistry and Alternative Energy" The Israel Academy of Sciences and Humanities. 2013; pp. 32-38. Abstract.

Milstein, "Discovery of Environmentally Benign Catalytic Reactions of Alcohols Catalyzed by Pyridine-Based Pincer Ru Complexes, Based on Metal-Ligand Cooperation," Top Catal 53(13-14):915-923 (2010).

Mola et al., "Ru-Hbpp-Based Water-Oxidation Catalysts Anchored on Conducting Solid Supports," Angew, Chem. Int. Ed., 47(31):5830-5832 (2008).

Monney et al. "Base-free hydrogen generation from methanol using a bi-catalytic system" Chemical Communications. 2014;50(6):707-9.

Montag et al. "Exclusive C—C Oxidative Addition in a Rhodium Thiophosphoryl Pincer Complex and Computational Evidence for an η3-C—C—H Agostic" Intermediate. Organometallics. Dec. 28, 2011;31(1):505-12.

Mulfort et al., "Supramolecular Cobaloxime Assemblies for H2 Photocatalysis: An Initial Solution State Structure—Function Analysis," Journal of Physical Chemistry B, 114(45):14572-14581 (2010).

(56) References Cited

OTHER PUBLICATIONS

Murahashi et al., "Ruthenium-Catalyzed Amidation of Nitriles with Amines. A Novel, Facile Route to Amides and Polyamides," J. Am. Chem. Soc., 108(24):7846-7847 (1986).
Murahashi et al., "Ruthenium-Catalyzed Hydration of Nitriles and Transformation of 6-Keto Nitriles to Ene-Lactams," J. Org. Chem., 57(9)2521-2523 (1992).
Muthusamy et al., "New Approach to the Synthesis of Macrocyclic Tetralactones via Ring-Closing Metathesis Using Grubbs' First-Generation Catalyst," Journal of Organic Chemistry, 72(4):1495-1498 (2007).
Naota et al., "Ruthenium-Catalyzed Transformations of Amino Alcohols to Lactams," Synlett, (10):693-694 (1991).
Navarro et al., "Redox and spectral properties of [Ru(trpy)L(H20)](Cl04)2 [trpy=2,2"2-6:'- terpyridine; L=4,4'-(OMe) 2bpy; 4,4'-(N02)2bpy]: A comparative computational study," Polyhedron, 15(9):1531-1537 (1996).
Nejman et al. "New access to racemic β 3-amino acids" Tetrahedron. Aug. 29, 2005;61(35):8536-41.
Nielsen et al. "Low-temperature aqueous-phase methanol dehydrogenation to hydrogen and carbon dioxide" Nature. Mar. 7, 2013;495(7439):85-9.
Nilsson et al. "High-resolution NMR and diffusion-ordered spectroscopy of port wine" Journal of agricultural and food chemistry. Jun. 16, 2004;52(12):3736-43.
Nordstrom et al., "Amide Synthesis from Alcohols and Amines by the Extrusion of Dihydrogen," J. Am. Chem. Soc., 130(52): 17672-17673 (2008).
Nunez Magro et al., "The synthesis of amines by the homogeneous hydrogenation of secondary and primary amides," Chem. Commun., 3154-3156 (2007).
Ohkuma et al. "Trans-RuH (η 1-BH4)(binap)(1, 2-diamine): A Catalyst for asymmetric hydrogenation of simple ketones under base-Free conditions" Journal of the American Chemical Society. Jun. 12, 2002;124(23):6508-9.
Owston et al., "Iridium-Catalyzed Conversion of Alcohols into Amides via Oximes," Organic Letters, 9(1 ):73-75 (2007).
Pefkianakis et al., "End-Functionalization of Semiconducting Species with Dendronized Terpyridine-Ru(II)-Terpyridine Complexes," Journal of Polymer Science, Part A: Polymer Chemistry, 47(7): 1939-1952 (2009).
Perez-Picaso et al., "Efficient Microwave Assisted Syntheses of 2,5-Diketopiperazines in Aqueous Media," Molecules, 14(8):2836-2849 (2009).
Pitet, "Sequential ROMP of cyclooctenes as a route to linear polyethylene block copolymers," Dalton Transactions, 42(25):9079-9088 (2013).
Pramanik et al., "Chemical oxidation of water to dioxygen. Homogeneous catalysis by a ruthenium aquo-complex," Transition Metal Chemistry, 22(5):524-526 (1997).
Pramanik et al., "Chemistry of [Ru(tpy){pap)(L'+ (tpy=2,22,'6,'"-terpyridine; pap=2-(phenylazo)pyridine; L'=Cl−, H20, CH3CN, 4-picoline, N3−; n=1,2). X-ray crystal structure of [Ru(tpy)(pap)(CH3CN)](Cl04)2 and catalytic oxidation of water to dioxygen by [Ru(tpy)(pap)(H20)]2+," Polyhedron, 17(9): 1525-1534 (1998).
Prechtl et al., "Direct coupling of alcohols to form esters and amides with evolution of H2 using in situ formed reuthenium catalysts," Catalysis Science and Technology, 2(10):2039-2042 (2012).
Ramos-Sende et al., "Electrocatalysis of C02 Reduction in Aqueous Media at Electrodes Modified with Electropolymerized Films of Vinylterpyridine Complexes of Transition Metals," Inorganic Chemistry, 34(12):3339-3348 (1995).
Rannard et al., "The Selective Reaction of Primary Amines with Carbonyl Imidazole Containing Compounds: Selective Amide and Carbamate Synthesis," Organic Letters, 2(14):2117-2120 (2000).
Rodríguez-Lugo et al. "A homogeneous transition metal complex for clean hydrogen production from methanol-water mixtures" Nature chemistry. Apr. 1, 2013;5(4):342-7.
Sala et al., "The Spectroscopic, Electrochemical and Structural Characterization of a Family of Ru Complexes Containing the C2-Symmetric Didentate Chiral 1,3-Oxazoline Ligand and Their Catalytic Activity," European Journal of Inorganic Chemistry, (33):5207-5214 (2007).
Samsonowicz et al. "Experimental and theoretical IR, Raman, NMR spectra of 2-, 3- and 4-aminobenzoic acids" Journal of molecular structure. Jun. 3, 2005:744:345-52.
Sandoval et al., "Mechanism of Asymmetric Hydrogenation of Ketones Catalyzed by BINAP/1,2-Diamine-Ruthenium(II) Complexes," J. Am. Chem. Soc., 125(44): 13490-13503 (2003).
Schwalbe et al., "Ruthenium polypyridine complexes of tris-(2-pyridyl)-1,3,5-triazine—unusual building blocks for the synthesis of photochemical molecular devices," Dalton Transactions, (20):4012-4022 (2009).
Seckin et al., "Preparation and Catalytic Properties of a Ru(II) Coordinated Polyimide Supported by a Ligand Containing Terpyridine Units," Journal of Inorganic and Organometallic Polymers and Materials, 19(2):143-151 (2009).
Sens et al., "Synthesis, Structure, and Acid-Base and Redox Properties of a Family of New Ru(II) Isomeric Complexes Containing the Trpy and the Dinucleating Hbpp Ligands," Inorganic Chemistry, 42(25):8385-8394 (2003).
Sens et al., "A new Ru Complex Capable of Catalytically Oxidizing Water to Molecular Dioxygen," Journal of the American Chemical Society, 126(25):7798-7799 (2004).
Seok et al., "The Comparative Study in the Oxygen Atom Transfer Reaction by Ruthenium Mono-Oxo Complexes," Bulletin of the Korean Chemical Society, 19(10):1084-1090 (1998).
Serrano et al., "Synthesis, Structure, Redox Properties, and Catalytic Activity of New Ruthenium Domplexes Containing Neutral or Anionic and Facial or Meridional Ligands: An Evaluation of Electronic and Geometrical Effects," Inorganic Chemistry, 46(13):5381-5389 (2007).
Shimizu et al., "Direct Dehydrogenative Amide Synthesis from Alcohols and Amines Catalyzed by y-Alumina Supported Silver Cluster," Chem. Eur. J., 15:9977-9980 (2009).
Smith et al., "Efficient Synthesis of Halomethyl-2,2'-Bipyridines: 4,4'-Bis(Chloromethyl)-2,2'-Bipyridine," Organic Syntheses, 78;82-90 (2002).
Spasyuk et al. "From esters to alcohols and back with ruthenium and osmium catalysts", Angew Chem Int Ed Engl. Mar. 12, 2012;51(11):2772-5.
Srimani et al. "Ruthenium Pincer-Catalyzed Cross-Dehydrogenative Coupling of Primary Alcohols with Secondary Alcohols under Neutral Conditions" Advanced Synthesis & Catalysis. Sep. 17, 2012;354(13):2403-6.
Srimani et al. "Catalytic coupling of nitriles with amines to selectively form imines under mild hydrogen pressure" Chemical Communications. 2012;48(97):11853-5.
Srimani et al. "Formation of Tertiary Amides and Dihydrogen by Dehydrogenative Coupling of Primary Alcohols with Secondary Amines Catalyzed by Ruthenium Bipyridine-Based Pincer Complexes" Advanced Synthesis & Catalysis. Sep. 16, 2013;355(13):2525-30.
Statler et al., "Alkyl, hydrido-, and Related Compounds of Ruthenium(II) with Trimethylphosphine. X-Ray Crystal Structures of Hydrido(tetrahydroborato-HH')tris{trimethylphosphine)ruthenium(II), tri-p-chloro-bis[tris (trimethylphosphine)ruthenium(II)] Tetrafluoroborate, and Bis[cis-methyltetrakis(trimethylphosphine)ruthenio]mercury (II)-Tetrahydrofuran(1/1)," J. Chem. Soc., Dalton Trans., 1731-1738 (1984).
Sussuchi et al., "Effect of the cis- and trans-[1,2-bis(diphenylphosphino)ethylene] ligands in the properties of diphosphine-polypyridyl complexes of ruthenium(II): Application to electrocatalytic oxidations of organic compounds," Journal of Molecular Catalysis A: Chemical, 259(1-2):302-308 (2006).
Sussuchi et al., "Synthesis and electrochemical, spectral and catalytic properties of diphosphine-polypyridyl ruthenium complexes," Polyhedron, 25(6): 1457-1463 (2006).
Swamy et al., "Mitsunobu and Related Reactions: Advances and Applications," Chem. Rev., 109{6):2551-2651 (2009).

(56) References Cited

OTHER PUBLICATIONS

Taher et al., "Acid-, Water- and High-Temperature-Stable Ruthenium Complexes for the Total Catalytic Deoxygenation of Glycerol to Propane," Chem. Eur. J., 15(39):10132-10143 (2009), and supporting information S10132/1-S10132/26.
Talwar et al. "Primary amines by transfer hydrogenative reductive amination of ketones by using cyclometalated IrIll catalysts" Chemistry—A European Journal. Jan. 3, 2014;20(1):245-52.
Tamaru et al., "Direct Oxidative Transformation of Aldehydes to Amides by Palladium Catalysis," Synthesis, 1983(6):474-476 (1983).
Tan et al. "Highly efficient tetradentate ruthenium catalyst for ester reduction: especially for hydrogenation of fatty acid esters", Org Lett. Feb. 6, 2015;17(3):454-7.
Tanaka et al., "Reversible Conversion Between Chemical and Electrical Energies Catalyzed by Ru Complexes Aimed to Construct Sustainable Society," Preprints of Symposia—American Chemical Society, Division of Fuel Chemistry, 53(1 ):236-237 (2008).
Thompson et al. "Nuclear magnetic resonance spectra of amines III. Identification of N-substituted amino acids" Journal of pharmaceutical sciences. Aug. 1, 1966;55(8):857-8.
Tillack et al., "Catalytic Amination of Aldehydes to Amides," Eur. J. Org. Chem., 2001:523-528 (2001).
Tillack et al., "A novel ruthenium-catalyzed amination of primary and secondary alcohols," Tetrahedron Letters, 47(50):8881-8885 (2006).
Tse et al., "Synthetic, spectral and catalytic activity studies of ruthenium bipyridine and terpyridine complexes: Implications in the mechanism of the ruthenium(pyridine-2,6-bisoxazoline)(pyrkline-2,6-dicarboxylate)-catalyzed asymmetric epoxidation of olefins utilizing H2O2," Journal of Organometallic Chemistry, 691 (21 ):4419-4433 (2006).
Tseng et al., "Mononuclear Ruthenium(II) Complexes that Catalyze Water Oxidation," Inorganic Chemistry, 47(24): 11763-11773 (2008).
Van Der Boom et at. "Cyclometalated phosphine-based pincer complexes: mechanistic insight in catalysis, coordination, and bond activation" Chemical reviews. May 14, 2003:103(5):1759-92.
Vogt et al. "A New Mode of Activation of CO2 by Metal-Ligand Cooperation with Reversible C_C and M_O Bond Formation at Ambient Temperature" Chemistry—A European Journal. Jul. 23, 2012;18(30):9194-7.
Wada et al., "Electrochemical Oxidation of Water to Dioxygen Catalyzed by the Oxidized Form of the Bis(ruthenium-hydroxo) Complex in H2O," Angew. Chem. Int. Ed., 39(8): 1479-1482 (2000).
Wada et al., "Syntheses and Redox Properties of Bis(hydroxoruthenium) Complexes with Quinone and Bipyridine Ligands. Water-Oxidation Catalysis," Inorganic Chemistry, 40(2):329-337 (2001).
Wasylenko et al., "Examination of Water Oxidation by Catalysts Containing Cofacial Metal Sites." European Journal of Inorganic Chemistry, 2010(20):3135-3142 (2010).
Wasylenko et al., "Insight into Water Oxidation by Mononuclear Polypyridyl Ru Catalysts." Inorganic Chemistry, 49(5):2202-2209 (2010).
Watanabe et al., "Ruthenium-Catalyzed N-Alkylation and N-Benzylation of Aminoarenes with Alcohols," J. Org. Chem., 49:3359-3363(1984).
Watson et al., "Ruthenium-Catalyzed Oxidation of Alcohols into Amides," Organic Letters, 11(12):2667-2670 (2009).
Wei et al. "Bimetallic catalysts for hydrogen generation". Chemical Society Reviews. 2012;41(24):7994-8008.
Williams et al., "Variable NMR Spin-Lattice Relaxation Times in Secondary Amides: Effect of Ramachandran Angles on Librational Dynamics," J. Phys. Chem. B, 102:6248-6259 (1998).
Yamaguchi et al., "Syntheses of mixed-ligand ruthenium(II) complexes with a terpyridine or a tris (pyrazolyl) methane and a bidentate ligand: their application for catalytic hydroxylation of alkanes," Inorganic Chemistry Communications, 1{8):299-301 (1998).
Yamakawa et al. "The Metal-Ligand Bifunctional Catalysis: A Theoretical Study on the Ruthenium (II)-Catalyzed Hydrogen Transfer between Alcohols and Carbonyl Compounds" Journal of the American Chemical Society. Feb. 23, 2000;122(7):1466-78.

Yeung et al.., "Chiral C1-symmetric 2,2"2,'6:'-terpyridine ligands: Synthesis, characterization, complexation with copper (II), rhodium(III) and ruthenium(II) ions and use of the complexes in catalytic cyclopropanation of styrene," Polyhedron, 29(5):1497-1507 (2010).
Yu et al., "Synthesis, redox properties and reactivities of ruthenium(II) complexes of 1,1'-biisoquinoline (BIQN) and X-ray crystal structure of [RuII(terpy)(BIQN)(Cl)]ClO4 (terpy=2,2"2,'6:'-terpyridine)," Polyhedron, 13(21): 2963-2969 (1994).
Zeng et al., "Direct Synthesis of Polyamides via Catalytic Dehydrogenation of Diols and Diamines," J. Am. Chem. Soc., 133(5)11159-1161 (2011).
Zhang et al., "Electron-Rich, Bulky Ruthenium PNP-Type Complexes, Acceptorless Catalytic Alcohol Dehydrogenation," Organometallics, 23(17):4026-4033 (2004).
Zhang et al., "Facile Conversion of Alcohols into Esters and Dihydrogen Catalyzed by New Ruthenium Complexes," J. Am. Chem. Soc., 127(31 ):10840-10841 (2005).
Zhang et al., "Efficient Homogeneous Catalytic Hydrogenation of Esters to Alcohols," Angew. Chem. Int. Ed., 45(7)1113-1115(2006).
Zhang et al., "Electron-rich, bulky PNN-type ruthenium complexes: synthesis, characterization and catalysis of alcohol dehydrogenation," Dalton Trans., 1:107-113 (2007).
Zhang et al., "Ru-TsDPEN with Formic Acid/Hunig's Base for Asymmetric Transfer Hydrogenation, a Practical Synthesis of Optically Enriched N-Propyl Pantolactam," The Journal of Organic Chemistry, 74(3):1411-1414 (2009).
Zhang et al., "Electron-Rich PNP- and PNN-Type Ruthenium(II) Hydrido Borohydride Pincer Complexes. Synthesis, Structure, and Catalytic Dehydrogenation of Alcohols and Hydrogenation of Esters," Organometallics, 30(21):5716-5724 (2011).
Zhang et al., "Efficient conversion of d-glucose into D-sorbitol over MCM-41 supported Ru catalyst prepared by a formaldehyde reduction process," Carbohydrate Research, 346(11):1327-1332 (2011).
Zhang et al., "Homogeneous catalytic synthesis of formic acid (salts) by hydrogenation of CO2 with H2 in the presence of ruthenium species," Journal of Molecular Catalysis A: Chem, 112(1 ):9-14 (1996).
Zhang et al., "Theoretical studies on the electronic structures and spectroscopic properties for a series of Osmium (II)-2,2"2,'6,'-terpyridine complexes," Theoretical Chemistry Account, 121(3-4):123-134 (2008).
Zhang et al., "Structures and spectroscopic properties of (Ru(iph)(L)2)2+ (L=cpy, mpy, npy) complexes containing tetradentate ligands," Wuli Huaxue Xuebao, 27(5):1089-1094 (2011). Translated abstract.
Zhao et al., "Selective hydrogenation of benzene to cyclohexene by a circulating method on monolithic catalyst Ru/ Al2O3/C0rdierite," Ranliao Huaxue Xuebao/Journal of Fuel Chemistry and Technology, 36{4}:499-502 (2008). Translated abstract.
Zhao et al., "Liquid-phase selective hydrogenation of benzene to cyclohexene on Ru/Al2O3-ZrO2/cordierite monolithic catalysts," Journal of Molecular Catalysis A: Chemical, 309(1/2):35-39 (2009).
Zhao et al., "Preparation and Characterization of Ru/Al2O3/ Cordierite Monolithic Catalysts for Selective Hydrogenation of Benzene to Cyclohexene," Catalysis Letters, 131(3-4):597-605 (2009).
Zhao et al., "Acceptorless, Neat, Ruthenium-Catalyzed Dehydrogenative Cyclization of Diols to Lactones," Organometallics, 24(10):2441-2446 (2005).
Zhao et al., "Monolithic Ru-based catalyst for selective hydrogenation of benzene to cyclohexene," Catalysis Communications, 9(3):459-464 (2008).
Zhao et al., "Selective Hydrogenation of Benzene to Cyclohexene on a Ru/Al2O3/Cordierite Monolithic Catalyst: Effect of Mass Transfer on the Catalytic Performance," Industrial and Engineering Chemistry Research, 47(14):4641-4647 (2008).
Zhou et al., "Ruthenium(II) Terpyridyl Complexes Exhibiting DNA Photocleavage: The Role of the Substituent on Monodentate Ligand," Journal of Physical Chemistry B, 113(33):11521-11526 (2009).
Zhou et al., "Synthesis of an Ionic Paramagnetic Ruthenium(III) Complex and its Application as an Efficient and Recyclable Catalyst for the Transfer Hydrogenation of Ketones," European Journal of Inorganic Chemistry, 2012(21 ):3435-3440 (2012).

(56) References Cited

OTHER PUBLICATIONS

Ziessel et al., "Co-ordinative properties of a hybrid phosphine-bipyridine ligand," J. Chem. Soc., Dalton Trans., 20:3777-3784(1997).

Zweifel et al., "Catalyzed Dehydrogenative Coupling of Primary Alcohols with Water, Methanol, or Amines," Angew. Chem., 121(3):567-571 (2009).

Taube, M., Rippin, D. W. N. T., Cresswell, D. L., & Knecht, W. (1983). A system of hydrogen-powered vehicles with liquid organc hydrides, *International Journal of Hydrogen Energy*, 8(3), 213-225.

RUTHENIUM COMPLEXES AND THEIR USES AS CATALYSTS IN PROCESSES FOR FORMATION AND/OR HYDROGENATION OF ESTERS, AMIDES AND RELATED REACTIONS

CROSS-REFERENCE TO RELATED APPLICATIONS

This application is a National Phase Application of PCT International Application No. PCT/IL2015/050887, International Filing Date Sep. 3, 2015, claiming priority of U.S. Provisional Patent Application No. 62/200,138, filed Aug. 3, 2015 and of Israel Patent Application No. 234478, filed Sep. 4, 2014, which are incorporated in their entirety herein by reference.

FIELD OF THE INVENTION

The present invention relates to novel Ruthenium complexes and their use, inter alia, for (1) dehydrogenative coupling of alcohols to esters; (2) hydrogenation of esters to alcohols (including hydrogenation of cyclic esters (lactones) or cyclic di-esters (di-lactones), or polyesters); (3) preparing amides from alcohols and amines (including the preparation of polyamides (e.g., polypeptides) by reacting dialcohols and diamines and/or polymerization of amino alcohols and/or forming cyclic dipeptides from β-amino alcohols and/or forming diamide by reacting diaminoalkane and alcohol; (4) hydrogenation of amides (including cyclic dipeptides, diamide, polypeptides and polyamides) to alcohols and amines (or diamine); (5) hydrogenation of organic carbonates (including polycarbonates) to alcohols or hydrogenation of carbamates (including polycarbamates) or urea derivatives to alcohols and amines; (6) dehydrogenation of secondary alcohols to ketones; (7) amidation of esters (i.e., synthesis of amides from esters and amines); (8) acylation of alcohols using esters; (9) coupling of alcohols with water and a base to form carboxylic acids; and (10) preparation of amino acids or their salts by coupling of amino alcohols with water and a base. The present invention further relates to the use of certain known Ruthenium complexes for the preparation of amino acids or their salts from amino alcohols.

BACKGROUND OF THE INVENTION

Metal-ligand cooperation (MLC), in which both the metal and the ligand undergo bond-making and breaking with incoming substrates, plays an important role in chemical and biological catalysis. A prevailing mode of MLC, is based on metal cooperation with ligands bearing N—H groups, mostly of the form H-M-NHR (Scheme 1a). Among several systems that operate in this fashion, pincer-type ligands have recently shown exceptional catalytic activity in hydrogenation and dehydrogenation reactions involving carbonyl groups. There are examples for catalytic hydrogenation of aldehydes, esters, imines, ketones, nitriles, and even amides and cyclic carbonates based on such MLC. Dehydrogenative coupling of alcohols to esters, alcohols with amines to form amides, as well as other catalytic reactions have also been reported.

Scheme 1.

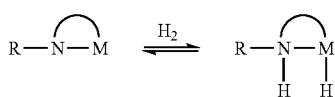

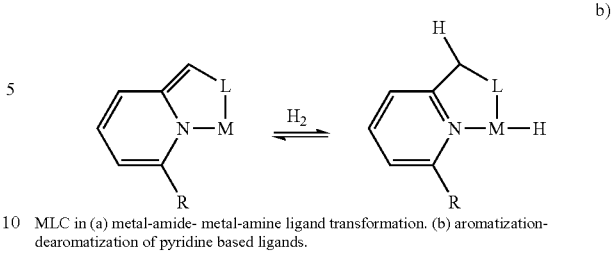

MLC in (a) metal-amide- metal-amine ligand transformation. (b) aromatization-dearomatization of pyridine based ligands.

The inventors of the present invention previously developed a new mode of MLC, involving aromatization/dearomatization of pyridine and bipyridine based ligands (Scheme 1b, FIG. 1). For example, deprotonation of the benzylic proton α to the pyridine group in a pyridine-based pincer complex can lead to its de-aromatization. The de-aromatized moiety can regain its aromaticity by cooperation between the metal and the ligand, resulting in the activation of chemical bonds, such as H—X (X=$NR_2$, H, OR or C), without formal change in the metal oxidation state (Scheme 1b). Several new, environmentally benign reactions catalyzed by PNP— or PNN—Ru and Fe pincer complexes, based on aromatization/de-aromatization strategy have been developed. They include dehydrogenative coupling of alcohols to esters, hydrogenation of esters to alcohols, coupling of alcohols with primary amines to form amides with liberation of $H_2$, direct synthesis of imines from alcohols and amines with liberation of $H_2$, catalytic coupling of nitriles with amines to selectively form imines and several other catalytic transformations.

Zeng et al. [Zeng, H.; Guan, Z. J. Am. Chem. Soc. 2011, 133, 1159] describes a process for preparation of polyamides via catalytic dehydrogenation of diols and diamines using PNN pincer ruthenium complexes.

U.S. Pat. No. 8,178,723, to some of the inventors of the present invention, describes methods for preparing amides, by reacting a primary amine and a primary alcohol in the presence of Ruthenium complexes, to generate the amide compound and molecular hydrogen.

U.S. Pat. No. 8,586,742, to some of the inventors of the present invention, describes methods for preparing primary amines from alcohols and ammonia in the presence of Ruthenium complexes, to generate the amine and water.

PCT patent publication no. WO 2012/052996 (U.S. Pat. No. 9,045,381) to some of the inventors of the present application, describes methods of using Ruthenium complexes for (1) hydrogenation of amides to alcohols and amines; (2) preparing amides from alcohols and amines; (3) hydrogenation of esters to alcohols; (4) hydrogenation of organic carbonates to alcohols and hydrogenation of carbamates or urea derivatives to alcohols and amines; (5) dehydrogenative coupling of alcohols to esters; (6) dehydrogenation of secondary alcohols to ketones; (7) amidation of esters (i.e., synthesis of amides from esters and amines); (8) acylation of alcohols using esters; (9) coupling of alcohols with water to form carboxylic acids; and (10) dehydrogenation of beta-amino alcohols to form pyrazines.

Given the widespread importance of amines, alcohols, amides and esters and their derivatives in biochemical and chemical systems, efficient syntheses that avoid the shortcomings of prior art processes are highly desirable.

SUMMARY OF THE INVENTION

The present invention relates to novel Ruthenium complexes and their use, inter alia, for (1) dehydrogenative coupling of alcohols to esters; (2) hydrogenation of esters to alcohols (including hydrogenation of cyclic esters (lactones) or cyclic di-esters (di-lactones), or polyesters); (3) preparing amides from alcohols and amines (including the preparation of polyamides (e.g., polypeptides) by reacting dialcohols and diamines and/or polymerization of amino alcohols and/or forming cyclic dipeptides from β-amino alcohols and/or forming diamide by reacting diaminoalkane and alcohol; (4) hydrogenation of amides (including cyclic dipeptides, diamides, polypeptides and polyamides) to alcohols and amines or diamine; (5) hydrogenation of organic carbonates (including polycarbonates) to alcohols or hydrogenation of carbamates (including polycarbamates) or urea derivatives to alcohols and amines; (6) dehydrogenation of secondary alcohols to ketones; (7) amidation of esters (i.e., synthesis of amides from esters and amines); (8) acylation of alcohols using esters; (9) coupling of alcohols with water and a base to form carboxylic acids; and (10) preparation of amino acids or their salts by coupling of amino alcohols with water and a base. The Ruthenium complexes described herein function as catalysts in the aforementioned processes. The present invention further relates to the use of certain Ruthenium complexes previously described in U.S. Pat. Nos. 8,178,723 and 9,045,381 for the preparation of amino acids or their salts from amino alcohols.

The inventors have unexpectedly discovered that pyridine-based pincer complexes of general formulae A1, A2, A3 and A4 have superior activity at catalyzing a variety of reactions as described herein. The new complexes are a new class of pyridyl ruthenium pincer complexes with sec-amine coordination to the metal (i.e., a Ru—N—H group). The new pincer complexes, optionally in the presence of a base, act as effective catalysts under exceedingly mild conditions for acceptorless dehydrogenative coupling of alcohols to esters and hydrogenation of esters, among other reactions. The simplicity, generality and excellent atom-economy of these processes make them attractive for use both in small and large scale applications.

Examples of such complexes include, but are not limited to, compounds of general formulae A1, B1 and B2, and individual complexes represented by the structure of formulae 1, 2, 3 or 4. In one embodiment, a crystallographically characterized novel monoanionic enamido Ru(II) complex (4) is obtained from the hydridochloride complex (1) upon addition of 2.5 equiv. of base (relative to the metal complex) by deprotonation of the amine proton as well as the methylene proton of the N-arm of the pincer ligand. The double deprotonated anionic enamido Ru(II) complex, formed in situ in the catalytic reactions, is presumed to be the actual active catalyst in these reactions. These reactions are further described in the experimental section herein below.

In one embodiment, the Ruthenium complex is represented by any one of formulae A1, A2, A3 or A4:

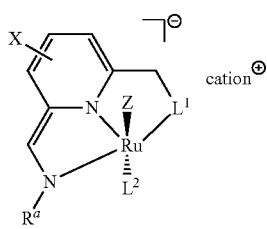

A1

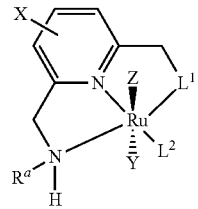

A2

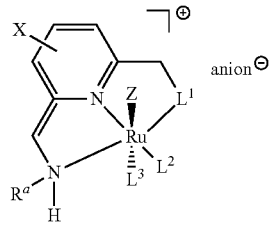

A3

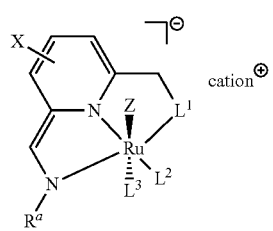

A4 wherein $L^1$ is selected from the group consisting of phosphine ($PR^bR^c$), phosphite $P(OR^b)(OR^c)$, phosphinite $P(OR^b)(R^c)$, amine ($NR^bR^c$), imine, oxazoline, sulfide ($SR^b$), sulfoxide ($S(=O)R^b$), heteroaryl containing at least one heteroatom selected from nitrogen and sulfur; arsine ($AsR^bR^c$), stibine ($SbR^bR^c$) and a N-heterocyclic carbene represented by the structures:

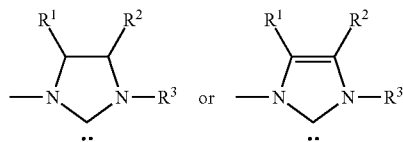

$L^2$ is a mono-dentate two-electron donor selected from the group consisting of CO, $PR^bR^cR^d$, $P(OR^b)(OR^c)(OR^d)$, $NO^+$, $AsR^bR^cR^d$, $SbR^bR^cR^d$, $SR^bR^c$, nitrile (RCN), isonitrile (RNC), $N_2$, $PF_3$, CS, heteroaryl, tetrahydrothiophene, alkene and alkyne;

$L^3$ is absent or is $L^2$;

Y and Z are each independently H or an anionic ligand selected from the group consisting of H, halogen, OCOR, OCOCF$_3$, OSO$_2$R, OSO$_2$CF$_3$, CN, OR, N(R)$_2$ and RS;

$R^a$ is H, alkyl, cycloalkyl, aryl, heterocyclyl, heteroaryl, alkylcycloalkyl, alkylaryl, alkylheterocyclyl or alkylheteroaryl;

$R^b$, $R^c$ and $R^d$ are each independently alkyl, cycloalkyl, aryl, heterocyclyl, heteroaryl, alkylcycloalkyl, alkylaryl, alkylheterocyclyl or alkylheteroaryl;

R, $R^1$, $R^2$ and $R^3$ are each independently H, alkyl, cycloalkyl, aryl, heterocyclyl, heteroaryl, alkylcycloalkyl, alkylaryl, alkylheterocyclyl or alkylheteroaryl;

X represents zero, one, two or three substituents independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety;

anion ⊖ represents a group bearing a single negative charge; and cation ⊕ represents a group bearing a single positive charge.

In one embodiment, X is absent (i.e., the pyridine moiety is unsubstituted). In another embodiment, $L^1$ is phosphine ($PR^bR^c$). In another embodiment, $L^2$ is CO. In another embodiment, Z and Y are independently H or halogen. The cation ⊕ may be selected from the group consisting of $Li^+$, $Cs^+$, $K^+$, $Na^+$, and, $N(R)_4^+$ (R=H or alkyl). The anion ⊕ may be selected from the group consisting of $BF_4^-$, $PF_6^-$, $B(C_6F_5)_4^-$, $B(C_6H_5)_4^-$, $^-OCOCF_3$, $^-OSO_2R$, $F^-$, $Cl^-$, $Br^-$, and $I^-$. Each possibility represents a separate embodiment of the present invention.

In some embodiments, the Ruthenium complex acts as a catalyst (and is thus designated "Ruthenium catalyst").

In one embodiment, the Ruthenium complex is represented by the structure of formula A1. In a particular embodiment of formula A1, Z is H, and the complex is represented by the structure A1'.

In another particular embodiment of formula A1, the Ruthenium complex is represented by the structure of formula B1. In one embodiment of formula B1, $L^2$ is CO. In another embodiment of formula B1, $R^a$ is selected from the group consisting of H, alkyl, cycloalkyl, aryl, alkylaryl, heterocyclyl and heteroaryl; and $R^b$ and $R^c$ are each independently selected from the group consisting of alkyl, cycloalkyl, aryl, alkylaryl, heterocyclyl and heteroaryl. In a currently preferred embodiment of formula B1, $R^a$ is selected from the group consisting of H, methyl, ethyl, propyl, isopropyl, n-butyl, sec-butyl, isobutyl, t-butyl and benzyl; and $R^b$ and $R^c$ are each independently selected from the group consisting of methyl, ethyl, propyl, isopropyl, n-butyl, sec-butyl, isobutyl, t-butyl and benzyl. In another embodiment of formula B1, the Ruthenium complex is represented by the structure of formula 4.

In another embodiment of the present invention, the Ruthenium complex is represented by the structure of formula A2. In one embodiment of formula A2, the Ruthenium complex is represented by the structure of formula B2. Examples of formula B2 include complexes 1, 2 or 3.

In another embodiment of the present invention, the Ruthenium complex is represented by the structure of formula A3. In another embodiment of the present invention, the Ruthenium complex is represented by the structure of formula A4.

The structures of Ruthenium complexes of Formulae A1, A1', B1, A2, B2, A3, A4, 1, 2, 3 and 4 are described in detail hereinbelow.

The present invention further provides various processes which utilize the Ruthenium complexes of the present invention as catalysts.

Thus, in some embodiments, the present invention provides a process for preparing an ester by dehydrogenative coupling of alcohols, by reacting an alcohol or a combination of alcohols in the presence of a Ruthenium complex as described herein as a reaction catalyst, to thereby generate the ester and molecular hydrogen.

In other embodiments, the present invention provides a process for hydrogenating an ester, comprising the step of reacting the ester with molecular hydrogen ($H_2$) in the presence of the Ruthenium complex as described herein as a reaction catalyst, thereby hydrogenating the ester.

In other embodiments, the present invention provides a process for preparing amides (including polyamides and polypeptides), by reacting a primary or secondary amine with a primary alcohol in the presence of a Ruthenium complex as described herein as a reaction catalyst, to generate the amide compound and molecular hydrogen ($H_2$). Use of diamines or dialcohols leads to diamides, whereas when diamines and dialcohols are used together, the process results in a polyamide. In another embodiment, this invention provides a process for preparing diamides, by reacting diaminoalkane and alcohol. Similarly, beta-amino alcohols can be dehydrogenated in the presence of the Ruthenium complexes of the present invention to form cyclic peptides and/or polypeptides. The process of the invention covers intermolecular coupling of amino alcohols to generate olio/polypeptides, or intramolecular coupling of amino alcohols to form lactams, including cyclic dipeptides (in the case of coupling of beta-amino alcohols). Mixtures of oligo/polypeptides and cyclic dipeptides are also contemplated.

In other embodiments, the present invention relates to a process for hydrogenating amides (including polyamides and polypeptides) by reacting the amide with molecular hydrogen ($H_2$) in the presence of the Ruthenium complexes of the present invention as a reaction catalyst, to generate the corresponding alcohol and amine. In another embodiment, the present invention relates to a process for hydrogenating diamides by reacting the diamide with molecular hydrogen ($H_2$) in the presence of the Ruthenium complexes of the present invention as a reaction catalyst, to generate the corresponding alcohol and diaminoalkane. In a similar manner, lactams (cyclic amides) can be hydrogenated to the corresponding amino alcohols. For example, glycine anhydride (GA) may be hydrogenated to ethanolamine. In addition, polyamides and/or polypeptides can be hydrogenated to the corresponding alcohols and amines.

Similar to the hydrogenation of esters and amides, the novel Ruthenium complexes of the present invention can also catalyze the hydrogenation of organic carbonates to alcohols, or the hydrogenation of carbamates to the corresponding amines and alcohols, or the hydrogenation of urea derivatives to the corresponding amines and methanol. Thus, in other embodiments, the present invention further provides a process for hydrogenating an organic carbonate, carbamate or urea derivative, with molecular hydrogen ($H_2$) in the presence of the Ruthenium complex, as described herein. Polyesters, polycarbonates, polycarbamates and/or polyureas can be hydrogenated in a similar manner. In a similar manner, lactones (e.g., cyclic esters) can be hydrogenated to alcohols. For example, cyclic di-esters (di-lactones) can be hydrogenated to the corresponding (vicinal) diols. In one particular embodiment, the present invention is directed to a process comprising hydrogenation of cyclic di-esters (di-lactones), which may be biomass-derived. e.g., glycolide and lactide to the corresponding 1,2-diols (vicinal diols). Each possibility represents a separate embodiment of the present invention.

The present invention further relates to a process for preparing a ketone by dehydrogenation of a secondary alcohol, by reacting the secondary alcohol in the presence of the Ruthenium complex of the present invention as a reaction catalyst, thereby generating the ester and molecular hydrogen.

The present invention further provides a process for preparing amides, by reacting an amine and an ester in the presence of the Ruthenium complex of the present invention as a reaction catalyst, to generate the amide compound and molecular hydrogen (H$_2$). Reactions of esters with diamines lead to diamides.

The present invention further provides a process for preparing esters by acylation of alcohols using esters in the presence of the Ruthenium complex of the present invention as a reaction catalyst, to generate the ester compound and molecular hydrogen. In one embodiment, the process involves reaction of primary alcohols and esters. In another embodiment, the process involves reaction of a secondary alcohols and esters.

The present invention further relates to a process for the coupling of alcohols with water and a base to form carboxylic acid salts, by contacting the alcohol and a base with water in the presence of the Ruthenium complex of the present invention as a reaction catalyst, thereby generating the carboxylic acid salt and molecular hydrogen. Optionally, the salt can be converted to the carboxylic acid upon reaction with an acid.

The present invention further relates to a process for preparing an amino acid by contacting an amino alcohol with the Ruthenium complex of the present invention as a reaction catalyst, in the presence of water and a base, under conditions sufficient to generate the amino acid. Preferably, the amino alcohol is a β- or γ-amino alcohol, resulting in an α- or β-amino acid, respectively, or their salts. In addition to the Ruthenium complexes of the present invention, i.e., complexes A1, A2, A3 or A4, this reaction can further be catalyzed by Ruthenium complexes described in U.S. Pat. Nos. 8,178,723, and 9,045,381, as further described herein.

Depending on the complex being used, the reaction permits the optional use of one or more equivalents of a base relative to the metal complex. For example, in one embodiment, when the Ruthenium complex is represented by the structure of formula A1, the reaction is conducted in the absence or the presence of a base. In particular, for complexes of formula A1 or A4 wherein Z is other than H, the process is conducted in the presence of at least one equivalent of base relative to the metal complex. In another embodiment, for complexes of formula A1 or A4 wherein Z is H, the process can be conducted in the absence of a base, although a base may be present. In another embodiment, when the Ruthenium complex is represented by the structure of formula A2 or A3 wherein Z is H and Y is an anionic ligand, the reaction is conducted in the presence of at least one equivalent of a base, preferably in the preference of at least 2 equivalents of a base, more preferably in the presence of at about 2.5 equivalents of a base relative to the metal complex. In another embodiment, when the Ruthenium complex is represented by the structure of formula A2 or A3 wherein Z and Y are each an anionic ligand, the reaction is conducted in the presence of at least two equivalents of a base, preferably in the preference of at least 3 equivalents of a base, more preferably in the presence of at least 3.5 equivalents of a base relative to the metal complex. Each possibility represents a separate embodiment of the present invention.

Preferred bases for use in the processes of the reaction include amide salts, hydrides, hydroxides and alkoxides. Non-limiting examples of bases include sodium hydroxide, potassium hydroxide, sodium methoxide, potassium methoxide, sodium ethoxide, potassium ethoxide, sodium propoxide, potassium propoxide, sodium butoxide, potassium butoxide, sodium t-butoxide, potassium t-butoxide, a metal bis(trimethylsilyl)amide salt (e.g., potassium bis(trimethylsilyl)amide (KHMDS)), sodium hydride, lithium diisopropylamide (LDA) and potassium hydride. Each possibility represents a separate embodiment of the present invention.

In some embodiments, the process of any of the embodiments of the present invention as described herein is conducted under neat conditions in the absence of a solvent. In other embodiments, however, the process is conducted in the presence of an organic solvent such as, but not limited to benzene, toluene, o-, m- or p-xylene, mesitylene (1,3,5-trimethyl benzene), dioxane, THF, DME, DMSO, anisole and cyclohexane.

In some embodiments the process is conducted under heat. In other embodiments, the process is conducted under inert gas. In other embodiments, the process is conducted under heat and under inert gas. However, the reactions of the invention can, when appropriate, also be conducted in the open air.

The mol % of the Ru complex relative to the substrate can range between about 0.0001-10 mol %, preferably between about 0.1-1%.

In some embodiments, the Ruthenium complex is attached through any available positions to a solid support, or embedded in a solid support, or is located on the surface of a solid support, which may be based on an inorganic or organic material. In some embodiments, the solid support comprises an inorganic material selected from the group consisting of silica, alumina, magnesia, titania, zirconia, montmorillonite, phyllosilicate, zeolites, talc, clays, layered double hydroxides, apatites, and any combination thereof. In other embodiments, the solid support comprises an organic polymer selected from polystyrene, polyethylene, polypropylene, polyvinylchloride, polytetrafluoro ethylene, polyethylene glycol, and poly(organo)siloxanes, and combinations thereof. Each possibility represents a separate embodiment of the present invention.

It is understood that any of the complexes described hereinabove may be used as is, or they may be formed during the catalytic reaction by combining Ru with the appropriate ligands so as to form the catalyst in situ. Thus, for example, the Ruthenium complexes described herein may be formed by combining Ruthenium precursors, such as Ruthenium salts and the appropriate ligands so as to form the catalytic complex in situ. Also, some of the complexes described below are "pre-catalyst", wherein the active catalytic species is formed in situ by combining the pre-catalyst with a base as described herein.

Also encompassed by the present invention are processes for preparing the Ruthenium complexes of the present invention, and intermediates used in these processes. In one embodiment, the present invention relates to a process for preparing a Ruthenium complex represented by the structure of formula A1 by reacting a Ruthenium complex of formula A2 in the presence of at least two equivalents of a base relative to the metal complex:

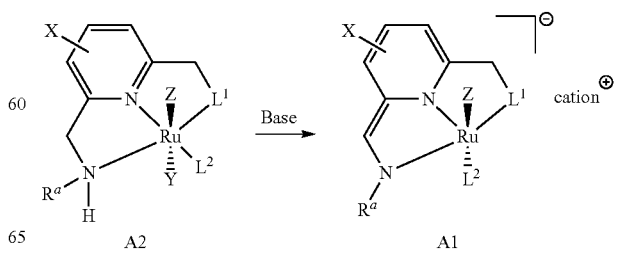

wherein L¹, L², X, Y and R^a are defined as described above. One particular embodiment of said process comprises preparing a Ruthenium complex represented by the structure of formula 4 from a precursor of formula 1.

In another embodiment, the present invention relates to a process for preparing a Ruthenium complex represented by the structure of formula A2 by reacting a precursor of formula B with a Ruthenium reagent represented by the structure Ru(Z)(Y)(L²)(P(Ar)₃)

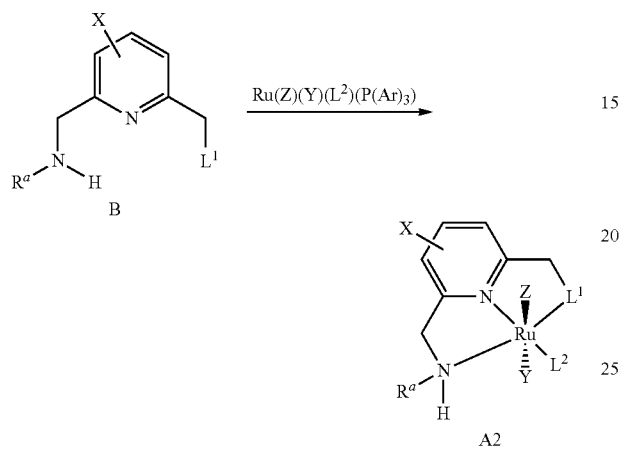

wherein Ar is phenyl or an alkyl-substituted phenyl.

Also encompassed by the present invention are certain intermediate compounds and their use in the preparation of the Ruthenium complexes of the present invention. For example, compounds of formula B are novel intermediates that represent a separate embodiment of the present invention.

The present invention will be understood and appreciated more fully from the following detailed description taken in conjunction with the appended figures:

DETAILED DESCRIPTION OF THE PRESENT INVENTION

Ruthenium Complexes

Figure 1:
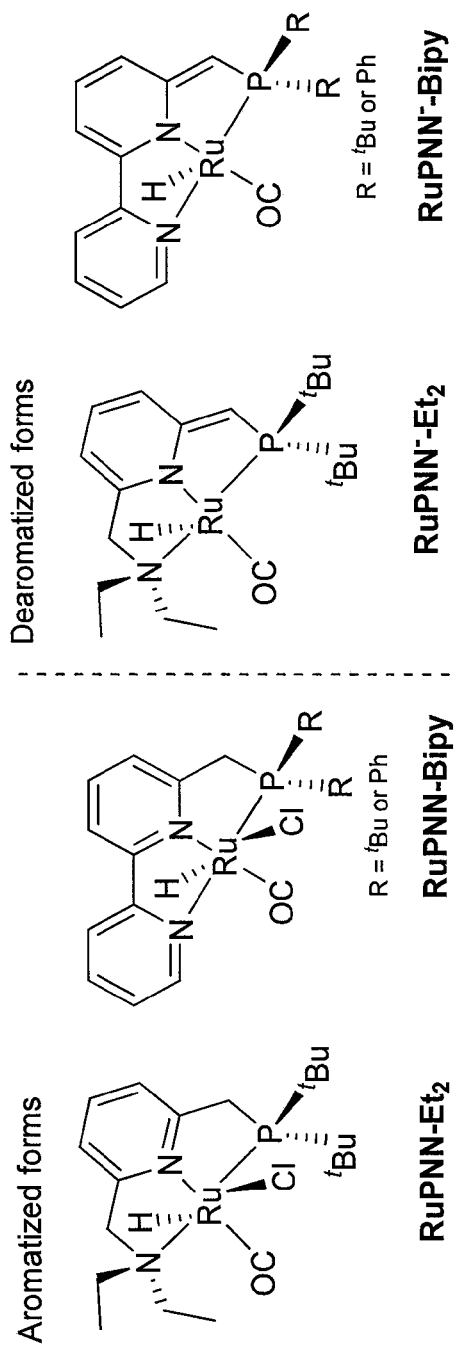
FIG. 1: Examples of Ru(II) pincer complexes used in aromatization/de-aromatization based MLC.

The Ruthenium complexes described herein function as catalysts in the processes described hereinbelow.

In one embodiment, the Ruthenium complex is represented by any one of formulae A1, A2, A3 or A4:

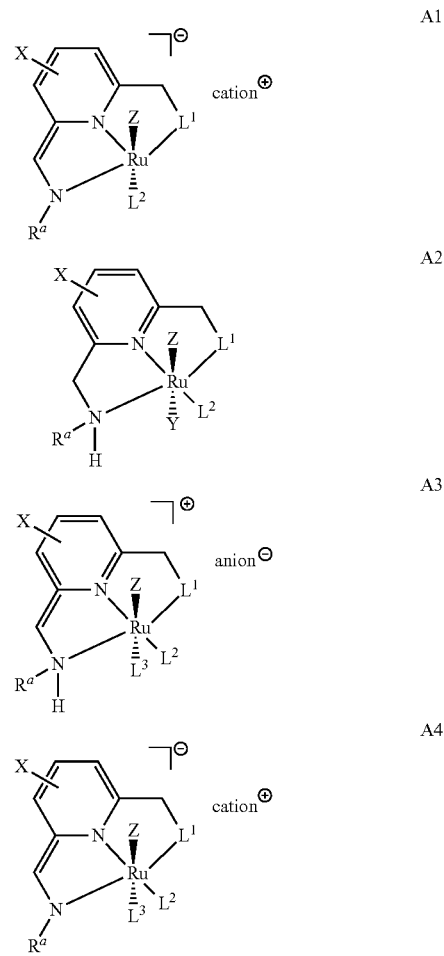

wherein
L¹ is selected from the group consisting of phosphine (PR^b R^c), phosphite P(OR^b)(OR^c), phosphinite P(OR^b) (R^c), amine (NR^b R^c), imine, oxazoline, sulfide (SR^b), sulfoxide (S(=O)R^b), heteroaryl containing at least one heteroatom selected from nitrogen and sulfur; arsine (AsR^b R^c), stibine (SbR^b R^c) and a N-heterocyclic carbene represented by the structures:

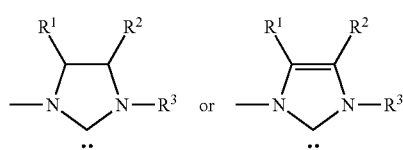

$L^2$ is a mono-dentate two-electron donor selected from the group consisting of CO, $PR^bR^cR^d$, $P(OR^b)(OR^c)(OR^d)$, $NO^+$, $AsR^bR^cR^d$, $SbR^bR^cR^d$, $SR^bR^c$, nitrile (RCN), isonitrile (RNC), $N_2$, $PF_3$, CS, heteroaryl, tetrahydrothiophene, alkene and alkyne;

$L^3$ is absent or is $L^2$;

Y and Z are each independently H or an anionic ligand selected from the group consisting of H, halogen, OCOR, $OCOCF_3$, $OSO_2R$, $OSO_2CF_3$, CN, OR, $N(R)_2$ and RS;

$R^a$ is H, alkyl, cycloalkyl, aryl, heterocyclyl, heteroaryl, alkylcycloalkyl, alkylaryl, alkylheterocyclyl or alkylheteroaryl;

$R^b$, $R^c$ and $R^d$ are each independently alkyl, cycloalkyl, aryl, heterocyclyl, heteroaryl, alkylcycloalkyl, alkylaryl, alkylheterocyclyl or alkylheteroaryl;

R, $R^1$, $R^2$ and $R^3$ are each independently H, alkyl, cycloalkyl, aryl, heterocyclyl, heteroaryl, alkylcycloalkyl, alkylaryl, alkylheterocyclyl or alkylheteroaryl;

X represents zero, one, two or three substituents independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety;

anion ⊖ represents a group bearing a single negative charge; and cation ⊕ represents a group bearing a single positive charge.

In one embodiment, X is absent (i.e., the pyridine moiety is unsubstituted). In another embodiment, $L^1$ is phosphine ($PR^bR^c$). In another embodiment, $L^2$ is CO. In another embodiment, Z and Y are independently H or halogen. The cation ⊕ may be selected from the group consisting of $Li^+$, $Cs^+$, $K^+$, $Na^+$, and $N(R)_4^+$ (R=H or alkyl). The anion ⊖ may be selected from the group consisting of $BF_4^-$, $PF_6^-$, $B(C_6F_5)_4^-$, $B(C_6H_5)_4^-$, $^-OCOCF_3$, $^-OSO_2R$, $F^-$, $Cl^-$, $Br^-$, $I^-$. Each possibility represents a separate embodiment of the present invention.

In some embodiments, the Ruthenium complex acts as a catalyst (and is thus designated "Ruthenium catalyst").

In one embodiment, the Ruthenium complex is represented by the structure of formula A1. In a particular embodiment of formula A1, Z is H, and the complex is represented by the structure A1':

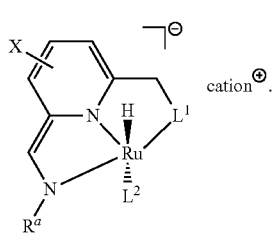

In another particular embodiment of formula A1, the Ruthenium complex is represented by the structure of formula B1:

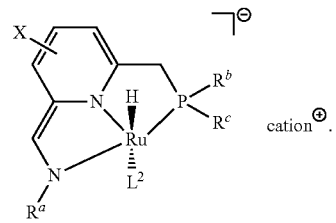

In one embodiment of formula B1, $L^2$ is CO. In another embodiment of formula B1, $R^a$ is selected from the group consisting of H, alkyl, cycloalkyl, aryl, alkylaryl, heterocyclyl and heteroaryl; and $R^b$ and $R^c$ are each independently selected from the group consisting of alkyl, cycloalkyl, aryl, alkylaryl, heterocyclyl and heteroaryl. In a currently preferred embodiment of formula B1, $R^a$ is selected from the group consisting of H, methyl, ethyl, propyl, isopropyl, n-butyl, sec-butyl, isobutyl, t-butyl and benzyl; and $R^b$ and $R^c$ are each independently selected from the group consisting of methyl, ethyl, propyl, isopropyl, n-butyl, sec-butyl, isobutyl, t-butyl and benzyl.

In one embodiment of formula B1, the Ruthenium complex is represented by the structure of formula 4

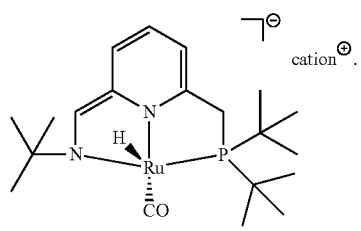

In one particular embodiment, the cation in complex 4 is $K^+$.

In another embodiment of the present invention, the Ruthenium complex is represented by the structure of formula A2. In one embodiment of formula A2, the Ruthenium complex is represented by the structure of formula B2.

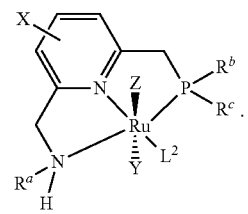

Examples of formula B2 include complexes 1, 2 or 3. Each possibility represents a separate embodiment of the present invention.

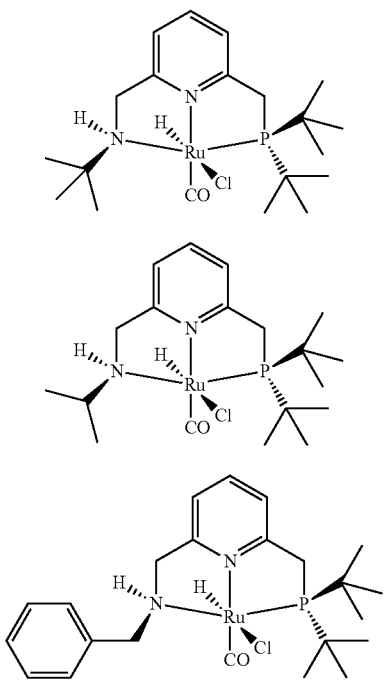

In another embodiment of the present invention, the Ruthenium complex is represented by the structure of formula A3. In another embodiment of the present invention, the Ruthenium complex is represented by the structure of formula A4.

Chemical Definitions

As used herein, the term "glycine anhydride" or "GA" denotes the cyclic compound 1,4-dimethylpiperazine-2,5-dione (structure hereinbelow wherein R=H). As used herein, the term "N,N-dimethyl glycine anhydride" or "N,N-dimethyl GA" denotes the cyclic compound 1,4-dimethylpiperazine-2,5-dione (structure hereinbelow wherein R=CH$_3$).

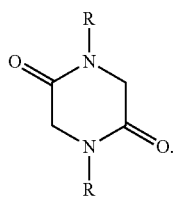

As used herein, the term alkyl, used alone or as part of another group, refers, in one embodiment, to a "C$_1$ to C$_{12}$ alkyl" and denotes linear and branched, saturated or unsaturated (e.g., alkenyl, alkynyl) groups, the latter only when the number of carbon atoms in the alkyl chain is greater than or equal to two, and can contain mixed structures. Non-limiting examples are alkyl groups containing from 1 to 6 carbon atoms (C$_1$ to C$_6$ alkyls), or alkyl groups containing from 1 to 4 carbon atoms (C$_1$ to C$_4$ alkyls). Examples of saturated alkyl groups include, but are not limited to, methyl, ethyl, n-propyl, isopropyl, n-butyl, iso-butyl, sec-butyl, tert-butyl, amyl, tert-amyl and hexyl. Examples of alkenyl groups include, but are not limited to, vinyl, allyl, butenyl and the like. Examples of alkynyl groups include, but are not limited to, ethynyl, propynyl and the like. Similarly, the term "C$_1$ to C$_{12}$ alkylene" denotes a bivalent radical of 1 to 12 carbons.

The alkyl group can be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryls, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, alkylthio, arylthio, or alkylsulfonyl groups. Any substituents can be unsubstituted or further substituted with any one of these aforementioned substituents. By way of illustration, an "alkoxyalkyl" is an alkyl that is substituted with an alkoxy group.

The term "cycloalkyl" used herein alone or as part of another group, refers to a "C$_3$ to C8 cycloalkyl" and denotes any unsaturated or unsaturated (e.g., cycloalkenyl, cycloalkynyl) monocyclic or polycyclic group. Nonlimiting examples of cycloalkyl groups are cyclopropyl, cyclobutyl, cyclopentyl, cyclohexyl or cycloheptyl. Examples or cycloalkenyl groups include cyclopentenyl, cyclohexenyl and the like. The cycloalkyl group can be unsubstituted or substituted with any one or more of the substituents defined above for alkyl. Similarly, the term "cycloalkylene" means a bivalent cycloalkyl, as defined above, where the cycloalkyl radical is bonded at two positions connecting together two separate additional groups.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl. An alkylaryl group denotes an alkyl group bonded to an aryl group (e.g., benzyl).

The term "heteroaryl" used herein alone or as part of another group denotes a heteroaromatic system containing at least one heteroatom ring atom selected from nitrogen, sulfur and oxygen. The heteroaryl contains 5 or more ring atoms. The heteroaryl group can be monocyclic, bicyclic, tricyclic and the like. Also included in this expression are the benzoheterocyclic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

The term "heterocyclic ring" or "heterocyclyl" used herein alone or as part of another group denotes a five-membered to eight-membered rings that have 1 to 4 heteroatoms, such as oxygen, sulfur and/or nitrogen. These five-membered to eight-membered rings can be saturated, fully unsaturated or partially unsaturated. Non-limiting examples of heterocyclic rings include piperidinyl, piperidinyl, pyrrolidinyl pyrrolinyl, pyrazolinyl, pyrazolidinyl, piperidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. The heterocyclyl group can be unsubstituted or substituted through available atoms with one or more groups defined hereinabove for alkyl.

The inorganic support which is attached to the Ruthenium complex can be, for example, silica, silica gel, glass, glass fibers, titania, zirconia, alumina and nickel oxide.

The polymeric moiety which is attached to the Ruthenium complex can be, for example, selected from polyolefins, polyamides, polyethylene terephthalate, polyvinylchloride, polyvinylidenechloride, polystyrene, polymethacrylate, natural rubber, polyisoprene, butadiene-styrene random copolymers, butadiene acrylonitrile copolymers, polycarbonate, polyacetal, polyphenylenesulfide, cyclo-olefin copolymers, styrene-acrylonitrile copolymers, ABS, styrene-maleic anhydride copolymers, chloroprene polymers, isobutylene copolymers, polystyrene, polyethylene, polypropylene, and the like.

The term "anion" as used herein refers to any moiety or group bearing a negative charge. Examples of anionic moieties include, but are not limited to halogen (e.g., F, Cl, Br, I), OCOR', OCOCF$_3$, OSO$_2$R', OSO$_2$CF$_3$, BF$_4$, PF$_6$, SbF$_6$, BR$_4$, ClO$_4$, AlCl$_4$, CN, OH or OR' wherein R' is selected from alkyl, cycloalkyl, aryl, alkylaryl, heterocyclyl and heteroaryl, wherein each of the alkyl, cycloalkyl, aryl, alkylaryl, heterocyclyl and heteroaryl is as defined above.

Novel Processes

The present invention further provides various processes which utilize the Ruthenium complexes of the present invention as catalysts.

In general, the processes of the present invention can be conducted in the absence or in the presence of a solvent. When a solvent is present, it can be an organic solvent, including but not limited to benzene, toluene, o-, m- or p-xylene, mesitylene (1,3,5-trimethyl benzene), dioxane, THF, DME, DMSO, anisole and cyclohexane.

The stoichiometric ratios of reagents can vary, and depend on the particular alcohol, amine, amide, ester etc., being used, as well as solvent used for the reaction. The reactions of the present invention can be performed for as long as needed so as to effect desired transformation, for example 1 hr to 24 hr or longer than 24 hr. The temperature range can vary from room temperature to heated conditions, for example up to 200° C.

In general, in all of the processes describe herein below, depending on the complex being used, the reaction permits the optional use of one or more equivalents of a base relative to the metal complex. For example, in one embodiment, when the Ruthenium complex is represented by the structure of formula A1 or A4 wherein Z is H, the reaction is conducted in the absence or the optional presence of a base. In another embodiment, for complexes of formula A1 or A4 wherein Z is other than H, the process is conducted in the presence of at least one equivalent of base relative to the metal complex. In another embodiment, when the Ruthenium complex is represented by the structure of formula A2 or A3 wherein Z is H and Y is an anionic ligand, the reaction is conducted in the presence of at least one equivalent of a base, preferably in the presence of at least 2 equivalents of a base, more preferably in the presence of about 2.5 equivalents of a base relative to the metal complex. In another embodiment, when the Ruthenium complex is represented by the structure of formula A2 or A3 wherein Z and Y are each an anionic ligand, the reaction is conducted in the presence of at least two equivalents of a base, preferably in the presence of at least 3 equivalents of a base, more preferably in the presence of at least 3.5 equivalents of a base relative to the metal complex. Each possibility represents a separate embodiment of the present invention.

Unless indicated otherwise, reference to "equivalent of a base" as used herein means the number of equivalents of a base used relative to the metal complex.

Preferred bases for use in the processes of the reaction include amide salts, hydrides, hydroxides and alkoxides. Non-limiting examples of bases include sodium hydroxide, potassium hydroxide, sodium methoxide, potassium methoxide, sodium ethoxide, potassium ethoxide, sodium propoxide, potassium propoxide, sodium butoxide, potassium butoxide, sodium t-butoxide, potassium t-butoxide, a metal bis(trimethylsilyl)amide salt (e.g., potassium bis(trimethylsilyl)amide (KHMDS)), lithium diisopropylamide (LDA), sodium hydride and potassium hydride. Each possibility represents a separate embodiment of the present invention.

1. Dehydrogenative Coupling of Alcohols:

In one aspect, the present invention provides a process for preparing esters by coupling of alcohols in the presence of the Ruthenium complexes of the present invention, to generate the ester compound and molecular hydrogen. The new complexes are unexpectedly better catalysts in this reaction than those described in U.S. Pat. No. 8,178,723, as manifested by the fact that reactions can be conducted under milder conditions and provides higher yields. For example, as shown in Table 1, dehydrogenative coupling of esters to alcohols can be conducted under reflux in ether, i.e., at temperatures about ~45° C. Under these conditions, dehydrogenation of alcohols to esters can proceed at up to 57% in the presence of the complex 3 of the present invention, whereas the corresponding complex RuPNN-Et$_2$ (FIG. 1) that is described in U.S. Pat. No. 8,178,723, was completely inactive under the same reaction conditions. In fact, reactions with RuPNN-Et$_2$ require much harsher reactions conditions (e.g., heating to 130° C. under reflux). Hence, the complexes of the present invention are unexpectedly and substantially better catalysts than those previously described.

In one embodiment, the process involves coupling of primary alcohols. In another embodiment, the process involves coupling of a primary and secondary alcohol. Use of dialcohols in the reaction leads to polyesters or to lactones.

Depending on the complex being used, the reaction permits the optional use of one or more equivalents of a base relative to the metal complex. When complexes A2 or A3 are used, the process is conducted in the presence of a base. When complex A1 is used (Z=H), a base is optional. When complex A2 is used (Z is other than H), at least one equivalent of a base relative to the metal complex is used.

In one embodiment, the process of the invention, i.e., the direct catalytic coupling of primary alcohols into esters and dihydrogen is illustrated in Scheme 2. In accordance with this process, two equivalents of a primary alcohol represented by formula R$^4$CH$_2$OH are converted to an ester by the structure R$^4$—C(=O)—OCH$_2$R$^4$. This novel, environmentally benign reaction, can be used to produce various esters from very simple substrates, with high atom economy and in some embodiments no stoichiometric activating agents, thus generating no waste.

Scheme 2

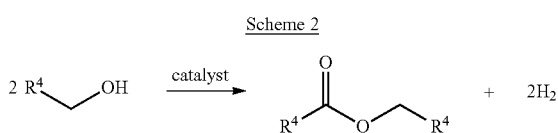

In another embodiment, the process of the invention involves the catalytic coupling of a primary alcohol and a secondary alcohol, as illustrated in Scheme 3.

Scheme 3

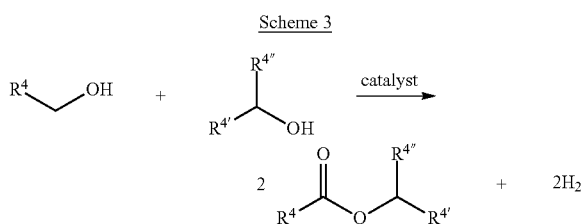

In Schemes 2 and 3, each of $R^4$ and $R^{4'}$ is independently selected from the group consisting of H, an unsubstituted or substituted alkyl, alkoxyalkyl, cycloalkyl, aryl, alkylaryl, heterocyclyl and heteroaryl.

When primary alcohols are used, the process of the invention contemplates symmetric coupling of alcohols to yield symmetric esters (i.e., 2 equivalents of the same alcohol are coupled). However, the present invention further contemplates the generation of asymmetric esters by coupling of different alcohols. In accordance with this embodiment, a first primary alcohol represented by formula $R^4CH_2OH$ is reacted with a second alcohol represented by formula $R^{4'}CH_2OH$ so as to generate an ester by the structure $R^4$—C(=O)—$OCH_2R^{4'}$ or an ester of formula $R^{4'}$—C(=O)—$OCH_2R^4$, as illustrated in Scheme 4:

Scheme 4

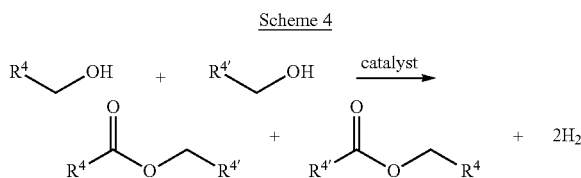

wherein $R^4$ and $R^{4'}$ are the same or different from each other and are each independently selected is from the group consisting of H, an unsubstituted or substituted alkyl, alkoxyalkyl, cycloalkyl, aryl, alkylaryl, heterocyclyl and heteroaryl.

A variety of alcohols can be used in the process of the invention. In some embodiments, the alcohol is selected from the group consisting of methanol, ethanol, n-propanol, iso-propanol, n-butanol, isobutanol, t-butanol, n-pentanol, 2-pentanol, 3-pentanol, 1-hexanol, 2-hexanol, 3-hexanol, 2-methoxyethanol, 2,2,2-trifluoroethanol, 2-methyl-1-butanol, 3-methyl-1-butanol, benzyl alcohol, 2-methoxy benzyl alcohol, 3-methoxy benzyl alcohol, 4-methoxy benzyl alcohol, 1-phenylethanol, and cyclohexane methanol. Each possibility represents a separate embodiment of the present invention.

In another embodiment, the process of the invention can also be applied to bis-acylation reactions with dialcohols to yield polyesters.

The reaction between the alcohols can be inter-molecular (i.e., the two alcohols are separate molecules). Alternatively, the reaction between the alcohols can be intra-molecular, i.e., the alcohol functionalities can be present in the same molecule, resulting in intra-molecular cyclization to generate a lactone. Each possibility represents a separate embodiment of the present invention.

2. Hydrogenation of Esters to Alcohols

The novel Ruthenium complexes of the present invention can also catalyze the hydrogenation of esters to the corresponding alcohols. Thus, in some embodiments, the present invention further provides a process for hydrogenating an ester with molecular hydrogen ($H_2$) in the presence of the Ruthenium complexes of the present invention.

Depending on the complex being used, the reaction permits the optional use of one or more equivalents of a base relative to the metal complex. When complexes A2 or A3 are used, the process is conducted in the presence of a base. When complex A1 is used (Z=H), a base is optional. When complex A2 is used (Z is other than H), at least one equivalent of a base relative to the metal complex is used.

One embodiment of the process of the invention, i.e., the direct catalytic conversion of esters to alcohols, is illustrated in Scheme 5, whereby an ester represented by the formula $R^5C(=O)$—$OR^6$ is hydrogenated to the corresponding alcohol or alcohols:

Scheme 5

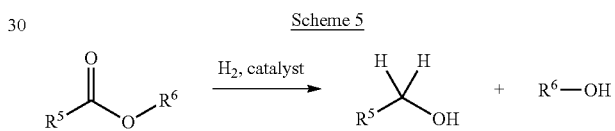

wherein $R^5$ is selected from the group consisting of H, an unsubstituted or substituted alkyl, alkoxyalkyl, cycloalkyl, aryl, alkylaryl, heterocyclyl and heteroaryl; and $R^6$ is selected from the group consisting of an unsubstituted or substituted alkyl, alkoxyalkyl, cycloalkyl, aryl, alkylaryl, heterocyclyl and heteroaryl It is apparent to a person of skill in the art that when the ester is symmetric (i.e., $R^5=R^6$), the reaction yields two equivalents of the same alcohol. However, when the ester is asymmetric (i.e., $R^5$ is different from $R^6$), the reaction yields a mixture of two alcohols.

In one embodiment, $R^5$ is H and the process comprises hydrogenating a formate ester of formula H—C(=O)—$OR^6$ to methanol and an alcohol of formula $R^6$—OH.

A variety of esters can be used in the process of the invention. In some embodiments, the ester is selected from the group consisting of hexyl hexanoate, methyl hexanoate, cyclohexyl hexanoate, tert-butyl acetate, cyclohexyl acetate, 2,2,2-trifluoroethyl 2,2,2-trifluoroacetate, benzyl benzoate, ethyl 3-phenylpropanoate, ethyl benzoate, butyl butyrate, methyl formate, ethyl formate, propyl formate butyl formate, methyl trifluoroacetate, methyl difluoroacetate and methyl monofluoroacetate. In other embodiments, the ester is a cyclic ester (a lactone). In yet other embodiments, the ester is a cyclic ester (lactone) or a di-ester (di-lactone), and the process results in a diol. In another embodiment, the cyclic ester is oxepan-2-one and the diol formed is hexane 1,6-diol. In yet other embodiments, the ester is a biomass-derived cyclic di-ester (di-lactone) such as, but not limited to glycolide or lactide. In yet another embodiment, the ester is polyester. Each possibility represents a separate embodiment of the present invention.

Catalytic homogeneous hydrogenation of cyclic di-esters (di-lactone), specifically glycolide and lactide to the corresponding 1,2-diols (vicinal diols) is of significant interest conceptually and practically, since these compounds are produced from biomass sources such as glycolic acid and lactic acid respectively via self-esterification, and their efficient hydrogenation can provide an alternative, mild approach to the indirect transformation of biomass resources to important synthetic building blocks. As contemplated herein, the unprecedented, environmentally benign, atom-economical route for the synthesis of propylene glycol and ethylene glycol are efficiently catalyzed by the Ruthenium complexes as described herein. These catalytic reactions proceed under neutral, homogeneous conditions, at mild temperatures and mild hydrogen pressures. The optical purity of a chiral diol is unaffected during the hydrogenation reactions.

The process of lactone or di-lactone hydrogenation can be catalyzed by any of the complexes of the present invention, as described herein (Scheme 6).

Scheme 6

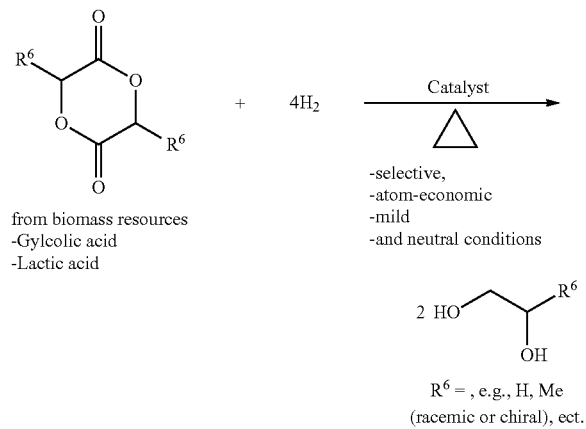

wherein $R^6$ is as described above.

A variety of cyclic di-esters (di-lactones) can be used in the process of the invention. In some embodiments, the ester is a biomass-derived cyclic di-ester (di-lactone) such as, but not limited to glycolide or lactide. Each possibility represents a separate embodiment of the present invention.

3. Dehydrogenative Coupling of Alcohols and Amines with Liberation of $H_2$ to Form Amides:

The present invention further provides a process for preparing amides, by reacting a primary or secondary amine with a primary alcohol in the presence of the Ruthenium complexes of the present invention, to generate the amide compound and molecular hydrogen ($H_2$). Depending on the complex being used, the reaction permits the optional use of one or more equivalents of a base relative to the metal complex. When complexes A2 or A3 are used, the process is conducted in the presence of a base. When complex A1 is used (Z=H), a base is optional. When complex A2 is used (Z is other than H), at least one equivalent of a base relative to the metal complex is used.

The process of the invention, i.e., the direct catalytic conversion of alcohols and amines into amides and dihydrogen is illustrated in Scheme 7. In accordance with this process, an amine represented by formula $R^7R^{7'}NH$ is reacted with an alcohol represented by the formula $R^8CH_2OH$ to generate an amide represented by the structure $R^8$—C(=O)—$NR^7R^{7'}$. This novel, environmentally benign reaction can be used to produce various amides from very simple substrates, with high atom economy and in some embodiments no stoichiometric activating agents, thus generating no waste.

Scheme 7

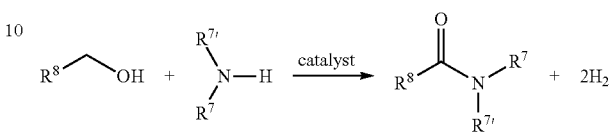

wherein $R^7$, $R^{7'}$ and $R^8$ are each independently selected from the group consisting of H an unsubstituted or substituted alkyl, alkoxyalkyl, cycloalkyl, aryl, alkylaryl, heterocyclyl and heteroaryl, or $R^7$ and $R^{7'}$ form together with the nitrogen a ring, wherein $R^7$, $R^{7'}$ and $R^8$ can be the same or different from each other.

In another embodiment, $R^7$ and $R^{7'}$ form together a ring, wherein said ring is a 5 to 8 membered ring. In another embodiment, the ring is saturated or unsaturated.

A variety of alcohols can be used in the process of the invention. In some embodiments, the alcohol is selected from the group consisting of methanol, ethanol, propanol, butanol, pentanol, hexanol (including 1-hexanol, 2-hexanol and 3-hexanol), 2-methoxyethanol, and 2-methyl-1-butanol. Each possibility represents a separate embodiment of the present invention.

A variety of primary and secondary amines (as well as ammonia) may be used in the process of the invention. In some embodiments, the amine is selected from the group consisting of benzylamine, 1-hexylamine, 1-pentylamine, benzylamine, 1-hexylamine, 1-pentylamine, 1-(2-furyl) methylamine, aniline, morpholine, pyrrolidine, piperidine, 2-methylhexylamine, cyclohexylamine, ethylenediamine, diethylenetriamine and 1,6-diaminohexane. Each possibility represents a separate embodiment of the present invention.

Use of diamines or dialcohols in the reaction leads to diamides, whereas when diamines and dialcohols are used together, the process results in a polyamide or polypeptide.

In one embodiment, the present invention relates to a process for the preparation of N,N'-diacetylethylenediamine (DAE) by catalytic dehyhdrogenative coupling of ethylenediamine (ED) and ethanol, the process comprises the step of reacting ethylenediamine (ED) with ethanol in the presence of a catalyst, thereby generating DAE and molecular hydrogen ($H_2$). The process is described in Scheme 8 hereinbelow.

Scheme 8

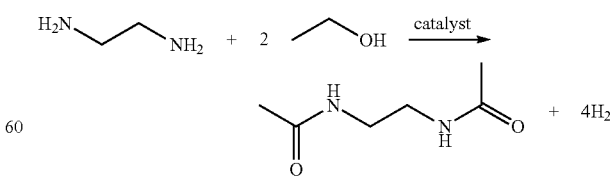

In one embodiment, the catalyst is a Ruthenium complex as described herein.

The monoamide, N-(2-aminoethyl)-acetamide (AEA), and N-ethylidenethane-1,2-diamine (EED) side products, are also formed in the process of ethylenediamine (ED) and ethanol, in addition to N,N'-diacetylethylenediamine (DAE) (Scheme 9).

Scheme 9

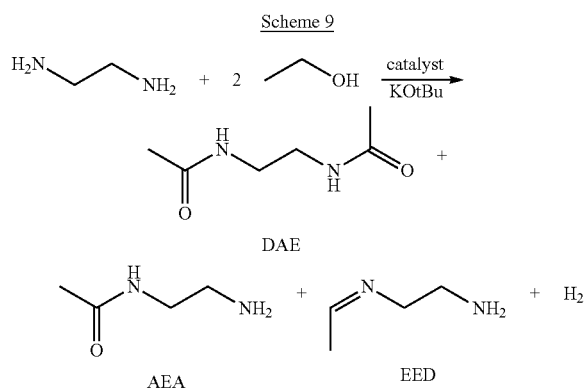

The stoichiometric ratios of reagents can vary, and depend on the particular catalyst being used, as well as solvent used for the reaction. In another embodiment, the reaction is conducted in the presence of at least one equivalent of a base with respect to the Ruthenium catalyst. In one embodiment, the base is 1 eq, 1.2 eq, 1.4 eq, 1.6 eq, 1.8 eq, 2 eq, 2.2 eq, 2.4 eq, 2.6 eq, 2.8 eq, 3 eq, 4 eq, 5, eq or 6 eq with respect to the catalyst. Each possibility represents a separate embodiment of the present invention. In one embodiment, the base is 1.2 eq with respect to the catalyst. In one embodiment, the base is 2.4 eq with respect to the catalyst.

Furthermore, the amine and alcohol may be present in the same molecule (i.e., amino-alcohol or their N-alkyl (e.g., N-methyl) derivatives). In this case, depending on the nature of the amino-alcohol, the process may be an intra-molecular process which results in a lactam; or an inter-molecular process which results in a polyamide, or the process results in a mixture of a lactam and a polyamide. Each possibility represents a separate embodiment of the present invention. For example, reaction of amino alcohols of formula RHN (CR$^1$R$^2$)$_n$CH$_2$OH (R, R$^1$ and R$^2$=H, alkyl) results in lactams for n=4, 5 or 6, such as caprolactam for n=6 and R$^1$=R$^2$=H. For n>6, the reaction typically results in polymers.

In one particular embodiment of amino-alcohols, the amine and alcohol together represent a beta-amino alcohol (e.g., H$_2$N—CH(R$^9$)CH$_2$OH wherein R$^9$ is defined below), as well as their N-alkyl derivatives (e.g., RHN—CH(R$^9$) CH$_2$OH wherein R is alkyl such as methyl). In one embodiment, the process is an intra-molecular process which results in a cyclic dipeptide (Scheme 10a). In another embodiment, the process is an inter-molecular process which results in a polypeptide (Scheme 10b). Combinations of polypeptides and cyclic dipeptides are also contemplated. These reactions are set forth in Schemes 10, 10a and 10b:

Scheme 10

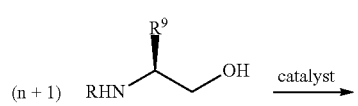

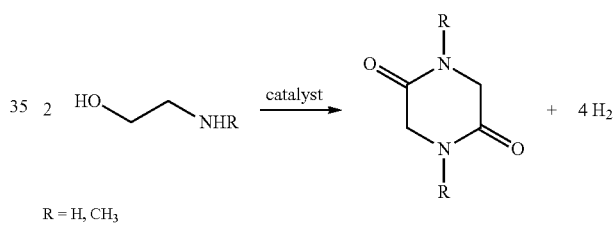

wherein R$^9$ is selected from the group consisting of H, an unsubstituted or substituted alkyl, cycloalkyl, aryl, alkylaryl, heterocyclyl and heteroaryl;
R is H or alkyl (e.g., methyl); and n is 1 to 20.

In one embodiment, R$^9$ is H or methyl, and the process is conducted in the presence of a solvent. In another embodiment, R and R$^9$ are each H, and the beta-amino alcohol is ethanolamine, resulting in a cyclic peptide (glycine anhydride or GA). In another embodiment, R is methyl and R$^9$ is H, and the beta-amino alcohol is 2-(methylamino) ethanol, resulting in a cyclic peptide (N,N-dimethyl GA), as illustrated in Scheme 10a:

Scheme 10a

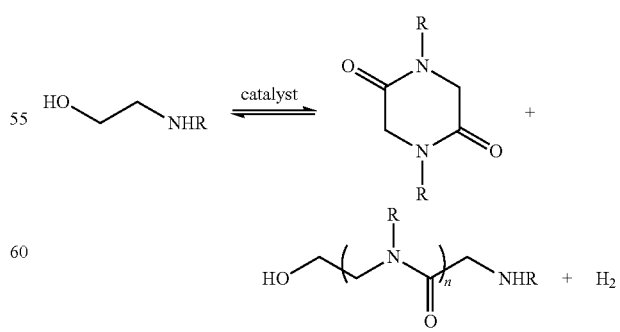

Some linear peptides can also be formed in the process of 2-aminoethanol or 2-(methylamino)ethanol dehydrogenation, in addition to GA and N,N-dimethyl GA. The mixture of linear peptides and GA/N,N-dimethyl-GA are capable of being hydrogenated back to AE or its N-methyl derivative, as illustrated in Scheme 10b:

Scheme 10b wherein R=H, CH$_3$ and n is 1-20.
In another embodiment, the process of the invention can also be applied to bis-acylation reactions with diamines.

Upon reacting alcohols and diamines, the corresponding bis-amides are produced in high yields. In some embodiments, the diamine is ethylenediamine, diethylenetriamine or 1,6-diaminohexane.

In some embodiments, when diamines and dialcohols are used, polyamides or peptides are obtained. This polyamidation reaction is general, environmentally benign and atom economical, and proceeds under neutral reaction conditions without the use of activators, condensing agents or other additives. Moreover, these methods produce $H_2$ as the only byproduct (Scheme 11):

Scheme 11

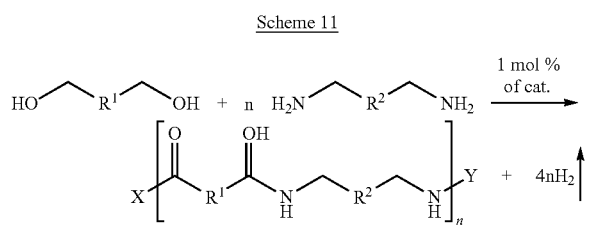

wherein $R^1$ and $R^2$ are each independently selected from a bond, O, NH, S, substituted or unsubstituted alkylene, alkenylene, alkynylene, cycloalkyl, aryl, heterocyclyl or heteroaryl.

A variety of dialcohols can be used for this reaction, non-limiting examples of which include hexane-1,2-diol, octane-1,8-diol, 1,3-phenylenedimethanol, (5-methoxy-1,3-phenylene)dimethanol, 1,4-phenylenedimethanol, pyridine-2,6-diyldimethanol, pentane-1,5-diol, cyclohexane-1,4-diyldimethanol, and (5-(hexyloxy)-1,3-phenylene)dimethanol.

A variety of diamines can be used for this reaction, non-limiting examples of which include hexane-1,6-diamine, ethane-1,2-diamine, 1,3-phenylenedimethanamine, and 1,4-phenylenedimethanamine.

4. Hydrogenation of Amides to Alcohols and Amines

The present invention provides a process for hydrogenating amides (including polyamides and polypeptides) by reacting the amide with molecular hydrogen ($H_2$) in the presence of the Ruthenium complexes of the present invention to generate the corresponding alcohol and amine. Depending on the complex being used, the reaction permits the optional use of one or more equivalents of a base relative to the metal complex. When complexes A2 or A3 are used, the process is conducted in the presence of a base. When complex A1 is used (Z=H), a base is optional. When complex A2 is used (Z is other than H), at least one equivalent of a base relative to the metal complex is used.

The process of the invention, i.e., the direct catalytic conversion of amides to alcohols and amides is illustrated in Scheme 12. This novel, environmentally benign reaction can be used to prepare alcohols and amines from any type of amide, with high atom economy and in some embodiments no stoichiometric activating agents, thus generating no waste. Thus, in one embodiment, the present invention provides a process for hydrogenating an amide represented by the formula $R^{10}C(=O)-N-R^{11}R^{11'}$ to an alcohol of formula $R^{10}CH_2OH$ and amine of formula $R^{11}R^{11'}NH$:

Scheme 12

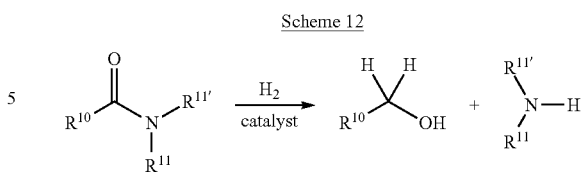

wherein $R^{10}$, $R^{11}$ and $R^{11'}$ are each independently selected from the group consisting of H, an unsubstituted or substituted alkyl, alkoxyalkyl, cycloalkyl, aryl, alkylaryl, heterocyclyl and heteroaryl.

A variety of amides can be used in the process of the invention. In some embodiments, the amide is selected from the group consisting of N-benzyl-2-methoxyacetamide, N-hexyl-2-methoxyacetamide, N-hexyl-3-methyloxetane-3-carboxamide, N-hexyl-2-furanylcarboxamide, N-benzylbenzamide, N-ethylacetamide, N-methylpropionamide, N-cyclohexyl-2-methoxyacetamide, N-phenylacetamide, N-phenylhexylamide, 2-methoxy-N-phenylacetamide, N-phenylbenzamide, Ethylenediamine-N,N'-(2-methoxyacetamide), N-hexanoylmorpholine, N-butanoylmorpholine, N-2-metoxyacetylpyrrolidine, N-formylmorpholine, N,N-dimethylformamide, N,N-diethylbenzamide, benzamide, 4-methylbenzamide, cyclohexanecarboxamide, hexanamide, acetamide, acrylamide and pivalamide. Each possibility represents a separate embodiment of the present invention.

In a similar manner, cyclic amides (lactams) can be hydrogenated to the corresponding amino alcohols. In one embodiment, the lactam is a cyclic peptide, which can be hydrogenated with the Ruthenium complex of the present invention to the respective amino alcohol (Scheme 13). In a similar manner, polyamides can be hydrogenated to amines and alcohols, and polypeptides or polyamides can be hydrogenated to amino alcohols.

In one particular embodiment, the cyclic amide is glycine anhydride (GA) or N,N-dimethyl GA, and the process results in ethanolamine or 2-(methylamino)ethanol.

Scheme 13

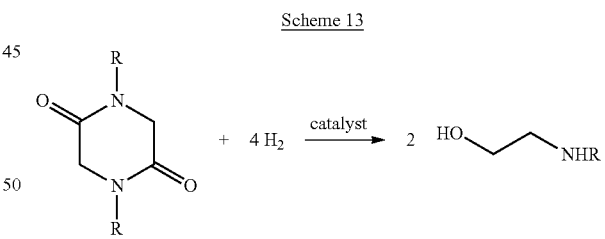

wherein R is H or $CH_3$.

As mentioned above, in another embodiment, mixtures of linear peptides and GA/N,N-dimethyl-GA are capable of being hydrogenated back to AE or its N-methyl derivative, as illustrated in Scheme 10b hereinabove.

In another embodiment, the diamide can is hydrogenated to diamine and alcohol. Specifically, the present invention relates to a catalytic process for the preparation of ethylenediamine (ED) and ethanol, the process comprises the steps of reacting N,N-diacetylethylenediamine (DAE) with molecular hydrogen ($H_2$) in the presence of a catalyst, thereby generating ethylenediamine (ED) and ethanol. This reaction is described in Scheme 14. In one embodiment, the catalyst is a Ruthenium complex as described herein.

25

Scheme 14

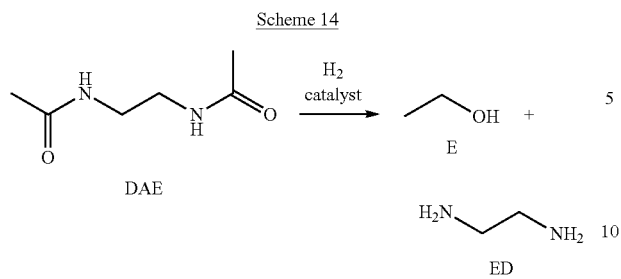

5. Hydrogenation of Organic Carbonates, Carbamates and Urea Derivatives

Similar to the hydrogenation of amides and esters, the novel Ruthenium complexes of the present invention can also catalyze the hydrogenation of organic carbonates, hydrogenation of carbamates, or hydrogenation of urea derivatives to the corresponding amines and/or alcohols. Thus, in some embodiments, the present invention further provides a process for hydrogenating an organic carbonate, carbamate or urea derivative with molecular hydrogen ($H_2$) in the presence of the Ruthenium complex of the present invention. Depending on the complex being used, the reaction permits the optional use of one or more equivalents of a base relative to the metal complex. When complexes A2 or A3 are used, the process is conducted in the presence of a base. When complex A1 is used (Z=H), a base is optional. When complex A2 is used (Z is other than H), at least one equivalent of a base relative to the metal complex is used.

One embodiment of the process of the invention, i.e., the direct catalytic hydrogenation of organic carbonates, is illustrated in Scheme 15, whereby a carbonate represented by the formula $R^{12}O$—$C(=O)$—$OR^{12'}$ is hydrogenated to the corresponding alcohols(s) and methanol:

Scheme 15

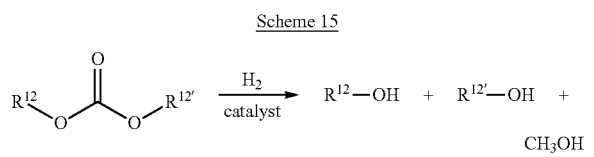

wherein $R^{12}$ and $R^{12'}$ are the same or different and are selected from the group consisting of an unsubstituted or substituted alkyl, alkoxyalkyl, cycloalkyl, aryl, alkylaryl, heterocyclyl and heteroaryl.

It is apparent to a person of skill in the art that when the organic carbonate is symmetric (i.e., $R^{12}=R^{12'}$) the reaction yields two equivalents of the same alcohol, and one equivalent of methanol. However, when the organic carbonate is asymmetric (i.e., $R^{12}$ is different from $R^{12'}$), the reaction yields a mixture of two alcohols, and methanol.

A variety of organic carbonates can be used in the process of the invention. In some embodiments, the carbonate is dimethyl carbonate, diethyl carbonate, dipropyl carbonate or dibutyl carbonate. In another embodiment, the carbonate is a polycarbonate, such as polyethylene carbonate or polypropylene carbonate. Each possibility represents a separate embodiment of the present invention.

Another embodiment of the process of the present invention, i.e., the direct catalytic hydrogenation of carbamates, is illustrated in Scheme 16, a carbamate represented by the formula $R^{13}O$—$C(=O)$—$NHR^{14}$ is hydrogenated to the corresponding amine, alcohol and methanol:

26

Scheme 16

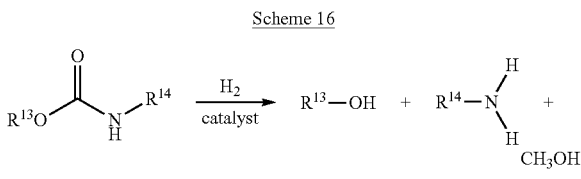

wherein $R^{13}$ is selected from the group consisting of an unsubstituted or substituted alkyl, alkoxyalkyl, cycloalkyl, aryl, alkylaryl, heterocyclyl and heteroaryl; and $R^{14}$ is selected from the group consisting of H or an unsubstituted or substituted alkyl, alkoxyalkyl, cycloalkyl, aryl, alkylaryl, heterocyclyl and heteroaryl.

A variety of organic carbamates can be used in the process of the invention. In some embodiments, the carbamate is methyl benzylcarbamate or methyl 4-methoxybenzylcarbamate. In another embodiment, the carbamate is a polycarbamate. Each possibility represents a separate embodiment of the present invention.

Another embodiment of the process of the present invention, i.e., the direct catalytic hydrogenation of urea derivatives, is illustrated in Scheme 17, whereby a urea derivative is hydrogenated to the corresponding amine(s) and methanol:

Scheme 17

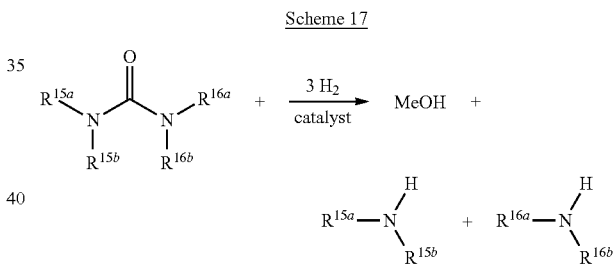

wherein each of $R^{15a}$ and $R^{16a}$, which may be the same or different, is selected from the group consisting of H, an unsubstituted or substituted alkyl, alkoxyalkyl, cycloalkyl, aryl, alkylaryl, and heterocyclyl, and each of $R^{15b}$ and $R^{16b}$, which may be the same or different, is selected from the group consisting of H, an unsubstituted or substituted alkyl, alkoxyalkyl, cycloalkyl, aryl, alkylaryl, and heterocyclyl. Alternatively, at least one of $R^{15a}$ and $R^{15b}$, and/or $R^{16a}$ and $R^{16b}$ together with the nitrogen to which they are attached form a heterocyclic ring A variety of symmetrical ($R^{15a}=R^{16a}$, $R^{15b}=R^{16b}$) and asymmetrical ($R^{15a}\neq R^{16a}$, $R^{15b}\neq R^{16b}$) urea derivatives can be used in the process of the invention, with each possibility representing a separate embodiment of the present invention. In some embodiments, the urea derivative is 1,3-dimethylurea, and the product of the reaction is methanol and two molecules of methylamine. In another embodiment, the urea derivative is selected from the group consisting of 1,3-dipropylurea, 1,3-dihexylurea, 1,3-bis(2-methoxyethyl)urea, 1,3-dicyclohexylurea, 1,3-dibenzylurea, 1,3-bis(4-methylbenzyl)urea, 1,3-bis(4-methylbenzyl)urea, 1,3-diphenylurea, 1,3-bis(4-(tert-butyl)phenyl)urea, 1,1,3,3-tetramethylurea, and di(piperidin-1-yl)methanone. Polyurea derivatives can also be hydrogenated in a similar manner. Each possibility represents a separate embodiment of the present invention.

6. Dehydrogenation of Secondary Alcohols:

In another aspect, the present invention further relates to a process for preparing a ketone by dehydrogenation of a secondary alcohol, comprising the step of reacting the secondary alcohol in the presence of the Ruthenium complex of the present invention, thereby generating the ketone and molecular hydrogen. Depending on the complex being used, the reaction permits the optional use of one or more equivalents of a base relative to the metal complex. When complexes A2 or A3 are used, the process is conducted in the presence of a base. When complex A1 is used (Z=H), a base is optional. When complex A2 is used (Z is other than H), at least one equivalent of a base relative to the metal complex is used.

The process of the invention, i.e., the direct catalytic conversion of secondary alcohols into ketones and dihydrogen is illustrated in Scheme 18. In accordance with this process, a secondary alcohol represented by formula $R^{17}CH(OH)R^{17'}$ is converted to a ketone represented by the structure $R^{17}$—C(=O)—$R^{17'}$:

Scheme 18

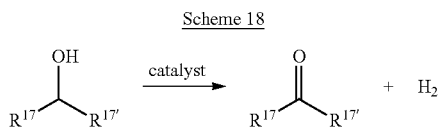

wherein $R^{17}$ and $R^{17'}$ are each independently selected from the group consisting of H or an unsubstituted or substituted alkyl, alkoxyalkyl, cycloalkyl, aryl, alkylaryl, heterocyclyl and heteroaryl A variety of alcohols can be used in the process of the invention. In some embodiments, the alcohol is selected from the group consisting of 1-phenyl-1-ethanol, 2-hexanol, cyclohexanol and 2-propanol. Each possibility represents a separate embodiment of the present invention.

7. Synthesis of Amides from Esters and Alcohols

The present invention further provides a process for preparing amides, by reacting an amine and an ester in the presence of the Ruthenium complex of the present invention, to generate the amide compound and molecular hydrogen ($H_2$). Reactions of esters with diamines lead to diamides. Depending on the complex being used, the reaction permits the optional use of one or more equivalents of a base relative to the metal complex. When complexes A2 or A3 are used, the process is conducted in the presence of a base. When complex A1 is used (Z=H), a base is optional. When complex A2 is used (Z is other than H), at least one equivalent of a base relative to the metal complex is used.

The process of the invention, i.e., the direct catalytic reaction of esters and amines into amides and dihydrogen is illustrated in Scheme 19. In accordance with this process, an amine represented by formula $R^{18}R^{18'}NH$ is reacted with an ester represented by the formula $R^{19}$—C(=O)—$OCH_2R^{19'}$ to generate an amide represented by the structure $R^{19}$—C(=O)—$NR^{18}R^{18'}$ or $R^{19'}$—C(=O)—$NR^{18}R^{18'}$. This novel, environmentally benign reaction can be used to produce various amides from very simple substrates, with high atom economy and in some embodiments no stoichiometric activating agents, thus generating no waste.

Scheme 19

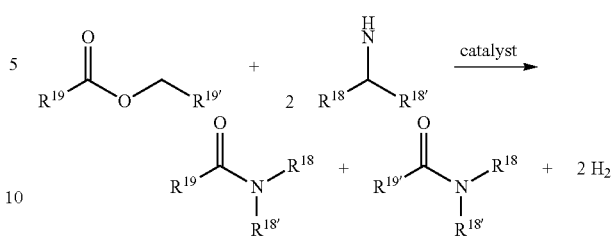

wherein $R^{18}$, $R^{18'}$, $R^{19}$ and $R^{19'}$ are each independently selected from the group consisting of H, an unsubstituted or substituted alkyl, alkoxyalkyl, cycloalkyl, aryl, alkylaryl, heterocyclyl and heteroaryl, wherein $R^{18}$, $R^{18'}$, $R^{19}$ and $R^{19'}$ can be the same or different from each other.

A variety of esters can be used in the process of the invention. In some embodiments, the ester is selected from the group consisting of ethyl acetate, butyl butyrate, pentyl pentanoate and hexyl hexanoate. Each possibility represents a separate embodiment of the present invention.

A variety of primary and secondary amines (as well as ammonia) may be used in the process of the invention. In some embodiments, the amine is selected from the group consisting of pyrrolidine, morpholine, 1-methyl piperazine, piperidine, piperazine, 1-hexylamine and p-tolylmethanamine.

In another embodiment, the process of the invention can also be applied to bis-acylation reactions with diamines. Upon reacting alcohols and diamines, the corresponding bis-amides are produced in high yields.

8. Acylation of Alcohols Using Esters with Liberation of $H_2$

The present invention further provides a process for preparing esters by acylation of alcohols using esters in the presence of the Ruthenium complex of the present invention, to generate the ester compound and molecular hydrogen. In one embodiment, the process involves reaction of primary alcohols and esters. In another embodiment, the process involves reaction of a secondary alcohols and esters. Depending on the complex being used, the reaction permits the optional use of one or more equivalents of a base relative to the metal complex. When complexes A2 or A3 are used, the process is conducted in the presence of a base. When complex A1 is used (Z=H), a base is optional. When complex A2 is used (Z is other than H), at least one equivalent of a base relative to the metal complex is used.

In one embodiment, the process of the invention, i.e., the direct catalytic acylation of alcohols using esters to yield an ester and dihydrogen is illustrated in Scheme 20. In accordance with this process, two equivalents of a primary or secondary alcohol represented by formula $R^{21}R^{21'}CHOH$ reacts with one equivalent an ester by the structure $R^{20}$—C(=O)—$OCH_2R^{20'}$ as shown in Scheme 20. This novel, environmentally benign reaction, can be used to produce various esters from very simple substrates, with high atom economy and in some embodiments no stoichiometric activating agents, thus generating no waste.

Scheme 20

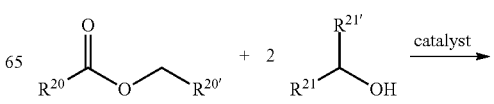

-continued

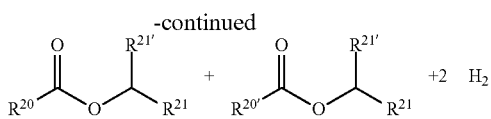

wherein $R^{20}$, $R^{20'}$, $R^{21}$ and $R^{21'}$ are each independently selected from the group consisting of H, an unsubstituted or substituted alkyl, alkoxyalkyl, cycloalkyl, aryl, alkylaryl, heterocyclyl and heteroaryl.

A variety of alcohols can be used in the process of the invention. In some embodiments, the alcohol is selected from the group consisting of cyclohexanol, cyclopentanol, 1-phenylethanol, isopropanol and 3-pentanol. Each possibility represents a separate embodiment of the present invention.

A variety of esters can be used as the starting materials. In some embodiments, the ester is selected from the group consisting of ethyl acetate, hexyl hexanoate, pentyl pentanoate, butyl butyrate, ethyl butyrate and methyl hexanoate.

9. Coupling of Alcohols with Water to Form Carboxylic Acid with Liberation of $H_2$ In another aspect, the present invention further provides a process for preparing carboxylic acids by contacting primary alcohols with water in the presence of the Ruthenium complex of the present invention and a base, to generate the carboxylic acid salt and molecular hydrogen and, if desired, followed by conversion of the carboxylic acid salt to the corresponding carboxylic acid.

In one embodiment, the process of the invention, i.e., the direct catalytic conversion of primary alcohols to carboxylic acids and dihydrogen is illustrated in Scheme 21. In accordance with this process, a primary alcohol represented by formula $R^{22}CH_2OH$ is contacted with water and a base (e.g., NaOH) as shown in Scheme 21. This novel, environmentally benign reaction, can be used to produce various carboxylic acids and their salts from very simple substrates, with high atom economy and in some embodiments no stoichiometric activating agents, thus generating no waste. If desired, the salt is neutralized with the appropriate acid to provide the corresponding carboxylic acid.

Scheme 21

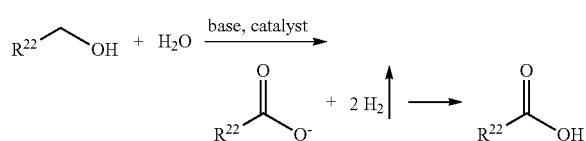

wherein $R^{22}$ is selected from the group consisting of H, an unsubstituted or substituted alkyl, alkoxyalkyl, aminoalkyl, cycloalkyl, aryl, alkylaryl, heterocyclyl and heteroaryl.

A variety of bases can be used for this reaction, non-limiting examples of which include an inorganic or organic base selected from sodium carbonate, potassium carbonate, sodium hydroxide, potassium hydroxide, sodium ethoxide, potassium tert-butoxide, sodium methoxide. The acid used to neutralize the salt can be, e.g. a mineral acid such as hydrochloric acid, hydrobromic acid, and the like. Each possibility represents a separate embodiment of the invention.

A variety of alcohols can be used in the process of the invention. In some embodiments, the alcohol is selected from the group consisting of butanol, pentanol, decanol, 2-methoxyethanol, 2-aminoethanol, 2-aminopropanol, 2-amino-2-phenylethanol, 2-phenylethanol, cyclohexylmethanol, 3-phenylbutan-1-ol, but-3-en-1-ol, (4-methoxyphenyl)methanol, and (2,4-dimethoxyphenyl)methanol. Use of amino alcohols leads to the formation of amino acids. In case of 2-aminoalcohols, natural amino acids are formed. Each possibility represents a separate embodiment of the present invention.

10. Preparing of Amino Acids or their Salts from Amino Alcohols

Because of their distinctive biological and chemical properties, amino acids and their derivatives fulfill key roles in biology, chemistry and medicinal research and many chemical and enzymatic methods have been developed for their preparation. Traditional chemical procedures for the synthesis of amino acids usually involve protection and deprotection steps, since unprotected amine groups undergo side reactions under the reaction conditions. Among these methods, transformation of amino alcohols to amino acids constitutes one of the most direct approaches. However, known methods mainly depend on stoichiometric use of strong and/or toxic oxidants, such as $KMnO_4$, pyridinium dichromate, Jones reagent and 1-hydroxy-1,2-benziodoxole-3 (1H)-one-1-oxide (IBX). In addition, some oxidative reactions promoted by catalysts and stoichiometric oxidants were developed for the synthesis of protected amino acids from protected amino alcohols, including systems based on $CrO_3/H_5IO_6$, $RuCl_3/NaIO_4$, $TEMPO/NaClO_2$, TEMPO/trichloroisocyanuric acid and others. However, besides the disadvantages of stoichiometric oxidants and the associated generation of copious waste, none of the methods mentioned above were used to transform non-protected amino alcohols to non-protected amino acids, hence step- and atom-economies in transforming amino alcohols to amino acids based on these processes are very low. A heterogeneous copper system was also reported in U.S. Pat. No. 6,646,160 to catalyze the transformation of amino alcohols to amino acids in water with very low turnover numbers (<6) under nitrogen pressure (4-20 atm) at relatively high temperature (160° C.). There remains a need in the art for highly desirable efficient and environmentally benign methods to transform amino alcohols to amino acids are unknown.

The inventors of the present invention have previously reported that pincer complex (iii) catalyzes the transformation of primary alcohols to the corresponding carboxylic acid salts in basic water, with no added oxidant. Both aliphatic alcohols and benzyl alcohols react smoothly, resulting in good to excellent yields of carboxylic acid salts, at low catalyst loading of 0.2 mol %, with $H_2$ as the only byproduct. However, in the case of 4-aminobutan-1-ol, the product was γ-butyrolactam, not 4-aminobutanoic acid (Scheme 22, eq 1) [E. Balaraman, E. Khaskin, G. Leitus, D. Milstein, Nat. Chem. (2013), 5, 122-125]. Apparently, the four-carbon amino alcohol undergoes intramolecular dehydrogenative amidation reaction in preference to reaction with water. It was further reported that employing precatalyst (i) and a catalytic amount of base, β-amino alcohols underwent bimolecular reactions to form cyclic dipeptides (diketopiperazines) (Scheme 22, eq 2), or oligopeptides (Scheme 22, eq 3). [Ganaprakasam, B., Balaraman, E., Ben-David, Y. & Milstein, D. Angew. Chem., Int. Ed. (20110), 50, 12240-12244].

Scheme 22. Acceptorless dehydrogenation reactions of amino alcohols.
Eq 4: targeted amino acid synthesis.

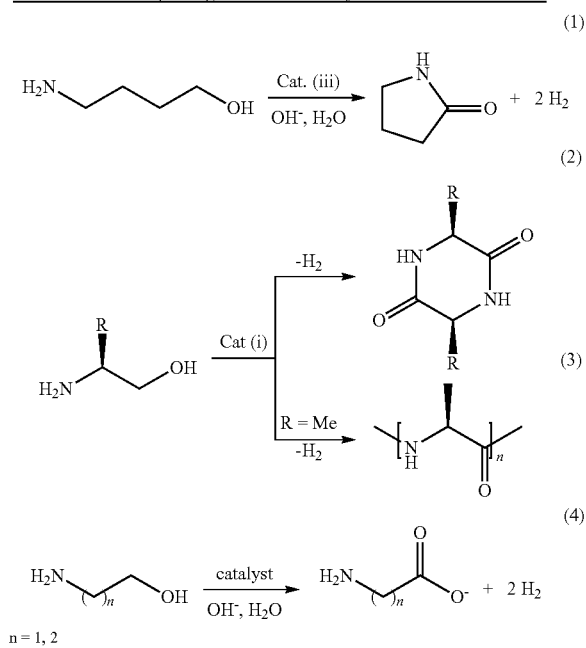

n = 1, 2

Surprisingly, it has now been discovered that it is possible to shift the direction of the reaction towards the production of α- and β-amino acids, which belong among the most important amino acids (Scheme 22, eq 4). Thus, reported herein is an efficient method for the direct, one step transformation of amino alcohols, preferably β- and γ-amino alcohols, to α-, and β-amino acid salts, respectively, using only basic water, without requirement of pre-protection or added oxidant, catalyzed by a the catalyst of this invention and catalysts. described in U.S. Pat. Nos. 8,178,723 and 9,045,38.

Thus, in another aspect, the present invention relates to a process for preparing an amino acid or a salt thereof, by contacting an amino alcohol with the Ruthenium complex of the present invention, in the presence of water and a base, under conditions sufficient to generate the amino acid or a salt thereof.

In one embodiment, the process of the invention involves the direct catalytic conversion of β- or γ-amino alcohols to amino acids or their salts, as illustrated by Scheme 23:

Scheme 23

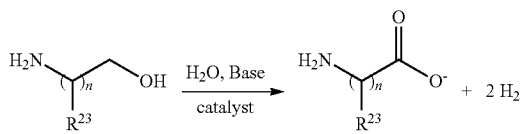

wherein $R^{23}$ is H or an unsubstituted or substituted alkyl; and
n is 1 or 2.

A variety of amino alcohols can be used in the process of preparing amino acids in accordance with the principles of the present invention. In some embodiments, the amino alcohol is selected from the group consisting of 2-aminoethanol (ethanolamine), 2-amino-1-butanol, diethanolamine, 2-aminopropanol, N-methylethanolamine, N,N-dimethylethanolamine, N-isopropylethanolamine, t-tert-butylethanolamine, 2-amino-3-methyl-1-butanol, prolinol, 2-amino-3-phenyl-1-propanol, 2-amino-2-phenyl-1-ethanol, 3-aminopropanol, N,N-dimethyl-3-aminopropanol, 3-amino-3-phenyl-1-propanol, and 2-aminobenzyl alcohol, or salts of any of the foregoing. Each possibility represents a separate embodiment of the present invention.

A variety of amino acids can be produced in accordance with the foregoing process. In some embodiments, the amino acid is selected from the group consisting of glycine, α-aminobutyric acid, 2-(2-hydroxyethylamino)acetic acid, alanine, sarcosine, dimethylglycine, N-isopropyl glycine, N-tert-butyl glycine, leucine, proline, phenylalanine, 2-phenylglycine, β-alanine, N,N-dimethyl-β-alanine, 3-amino-3-phenyl propanoic acid, and anthranilic acid, or salts of any of the foregoing. Each possibility represents a separate embodiment of the present invention.

In addition to the Ruthenium complexes of the present invention, i.e., complexes A1, A2, A3 or A4, this reaction can further be catalyzed by Ruthenium complexes described in U.S. Pat. No. 8,178,723, the contents of which are incorporated by reference herein. The compounds of U.S. Pat. No. 8,178,723 are pyridine based derivatives represented by the structure of formula A11', A22' and A33':

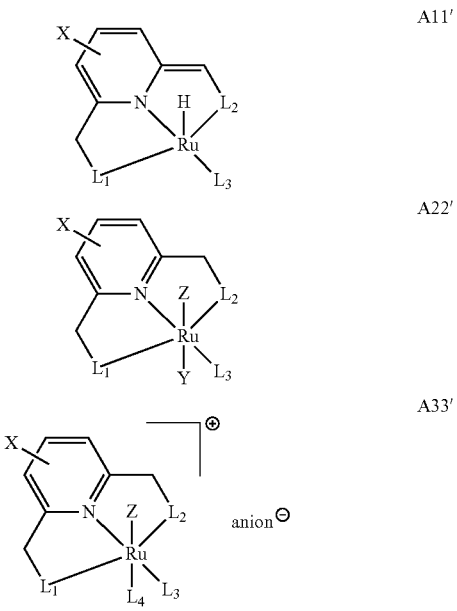

wherein
$L_1$ and $L_2$ are each independently selected from the group consisting of nucleophilic carbene (:C(R)$_2$), P(R)$_2$, P(OR)$_2$, N(R)$_2$, imine, SR, SH, S(=O)R, heteroaryl wherein the heteroatom is selected from nitrogen and sulfur, As(R)$_2$, Sb(R)$_2$ and an N-heretocyclic carbene represented by the structure:

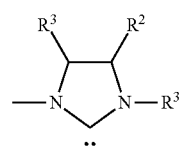

each of R, $R^2$ and $R^3$ are independently selected from the group consisting of alkyl, cycloalkyl, aryl, alkylaryl, heterocyclyl and heteroaryl;

$L_3$ is a mono-dentate two-electron donor selected from the group consisting of CO, $P(R)_3$, $P(OR)_3$, $NO^+$, $As(R)_3$, $Sb(R)_3$, $S(R)_2$, nitrile (RCN) and isonitrile (RNC) wherein R is as defined above;

$L_4$ is absent or is $L_3$;

Y and Z are each independently H or an anionic ligand selected from the group consisting of halogen, OCOR, $OCOCF_3$, $OSO_2R$, $OSO_2CF_3$, CN, OH, OR, $N(R)_2$, RS and SH; wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support and a polymeric moiety;

and anion represents a group bearing a single negative charge.

In one embodiment, the Ruthenium complex is represented by the structure of formula A11'. In a particular embodiment of formula A11', the Ruthenium complex is represented by the structure of formula B11':

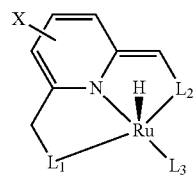

B11'

In another particular embodiment of formula A11', the Ruthenium complex is represented by the structure of formula C11':

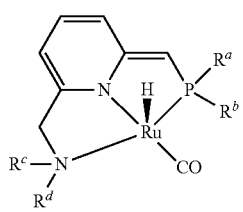

C11' wherein each of $R^a$, $R^b$, $R^c$ and $R^d$ is independently selected from the group consisting of alkyl, cycloalkyl, aryl, alkylaryl, heterocyclyl and heteroaryl.

In one currently preferred embodiment, each of $R^a$ and $R^b$ is tert-butyl. In another currently preferred embodiment, each of $R^c$ and $R^d$ are ethyl. In a particularly preferred embodiment, the Ruthenium complex is represented by the structure of formula (ii) (also designated "dearomatized RuPNN-$Et_2$").

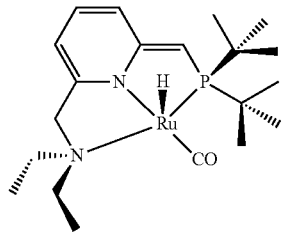

(ii)

In one embodiment of formula A22', the Ruthenium complex is represented by the structure of formula B22'.

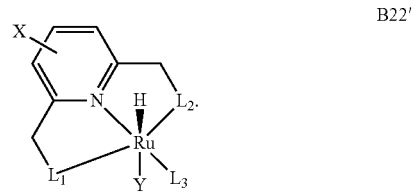

B22'

In another particular embodiment of formula A22', the Ruthenium complex is represented by the following structure of formula C22':

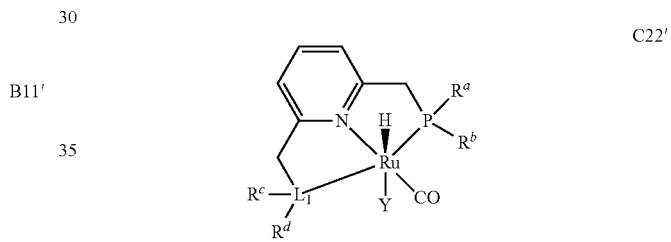

C22' wherein each of $R^a$, $R^b$, $R^c$ and $R^d$ is independently selected from the group consisting of alkyl, cycloalkyl, aryl, alkylaryl, heterocyclyl and heteroaryl.

In one currently preferred embodiment, Y is halogen, such as chloro. A currently preferred complex is a Ruthenium complex is represented by the structure of formula (i) also designated "aromatized RuPNN-$Et_2$"):

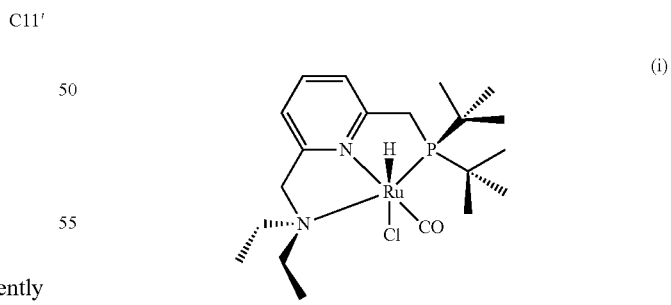

(i)

In another embodiment of the present invention, the Ruthenium complex is represented by the structure of formula A33'.

Compounds of formula A22' (of which Compound (i) is a representative) and formula A33' are precursors of compounds of formula A11'. It is understood that any one or more of the precursors can themselves function as catalysts in the process of the present invention.

The Ruthenium complexes of formulae A11', A22', A33', B11', C11', B22', C22', (i) and (ii) may be prepared in accordance with the methods described in U.S. Pat. No. 8,178,723, the contents of which are incorporated by reference herein in their entirety.

Furthermore, the preparation of amino acids from amino alcohols can further be catalyzed by pincer complex described in U.S. Pat. No. 9,045,381, the contents of which are incorporated by reference herein. Such complexes are represented by any one of formulae A1", A2" or A3":

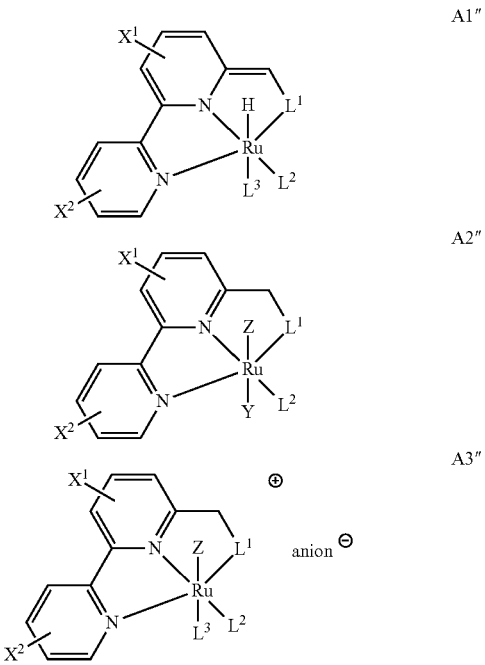

wherein
$L^1$ is selected from the group consisting of phosphine $(PR^aR^b)$, phosphite $P(OR^a)(OR^b)$, phosphinite $P(OR^a)(R^b)$, amine $(NR^aR^b)$, imine, oxazoline, sulfide $(SR^a)$, sulfoxide $(S(=O)R^a)$, heteroaryl containing at least one heteroatom selected from nitrogen and sulfur; arsine $(AsR^aR^b)$, stibine $(SbR^aR^b)$ and a N-heterocyclic carbene represented by the structures:

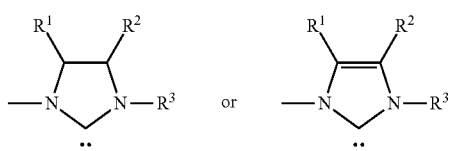

$L^2$ is a mono-dentate two-electron donor selected from the group consisting of CO, $PR^aR^bR^c$, $P(OR^a)(OR^b)(OR^c)$, $NO^+$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene and alkyne;
$L^3$ is absent or is $L^2$;
Y and Z are each independently H or an anionic ligand selected from the group consisting of H, halogen, OCOR, OCOCF$_3$, OSO$_2$R, OSO$_2$CF$_3$, CN, OR, N(R)$_2$ and RS;
$R^a$, $R^b$ and $R^c$ are each independently alkyl, cycloalkyl, aryl, heterocyclyl, heteroaryl, alkylcycloalkyl, alkylaryl, alkylheterocyclyl or alkylheteroaryl;

R, $R^1$, $R^2$ and $R^3$ are each independently H, alkyl, cycloalkyl, aryl, heterocyclyl, heteroaryl, alkylcycloalkyl, alkylaryl, alkylheterocyclyl or alkylheteroaryl;

$X^1$ represents zero, one, two or three substituents and $X^2$ represents zero, one, two, three or four substituents, wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety; and anion represents a group bearing a single negative charge.

In one embodiment, $X^1$ and $X^2$ are absent (i.e, the bipyridine moiety is unsubstituted). In another embodiment, $L^1$ is phosphine $(PR^aR^b)$. In another embodiment, $L^2$ is CO.

In one embodiment, the Ruthenium complex is represented by the structure of formula A1":

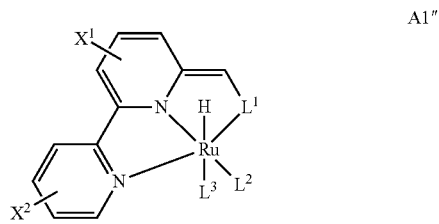

In a particular embodiment of formula A1", the Ruthenium complex is represented by the structure of formula B1". In another particular embodiment of formula A1", the Ruthenium complex is represented by the structure of formula C1".

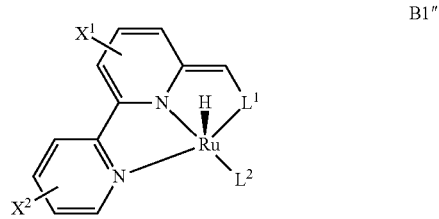

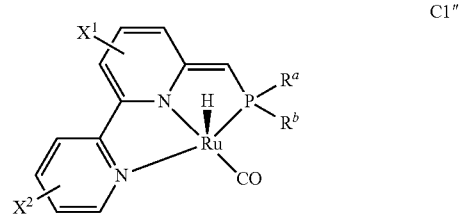

Each of $L^1$, $L^2$, $X^1$, $X^2$, $R^a$ and $R^b$ in Formulae B1" and C1" are as defined for formula A1". Each possibility represents a separate embodiment of the present invention.

In one embodiment, each of $R^a$ and $R^b$ is tert-butyl. In another currently, each of $R^c$ and $R^d$ are isopropyl. Each possibility represents a separate embodiment of the present invention.

In one embodiment, the Ruthenium complex is represented by the structure of formula (vi).

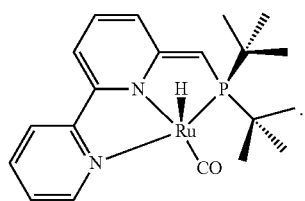

(vi)

In another embodiment of the present invention, the Ruthenium complex is represented by the structure of formula A2":

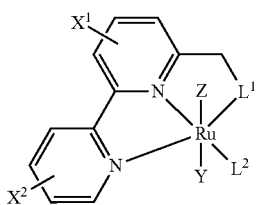

A2"

In one embodiment of Formula A2", Z and Y are either each H, each a halogen (e.g., F, Cl, Br, I) or one of Z and Y is H and the other a halogen. Each possibility represents a separate embodiment of the present invention.

In one embodiment of formula A2", the Ruthenium complex is represented by the structure of formula B2":

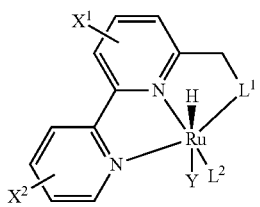

B2"

In another particular embodiment of formula A2", the Ruthenium complex is represented by the following structure of formula C2":

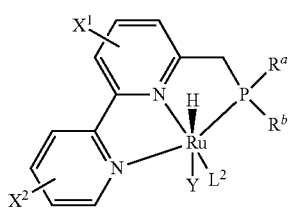

C2"

Each of $L^1$, $L^2$, $X^1$, $X^2$, Y, $R^a$ and $R^b$ in formulae B2" and C2" are as defined in formula A2". Each possibility represents a separate embodiment of the present invention.

In one embodiment, Y is halogen, such as chloro. For example, the Ruthenium complex may be represented by the structure of any of formulae (iii), (iv) or (v):

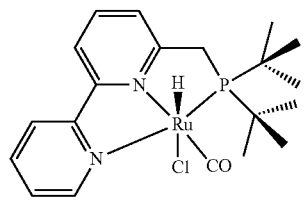

(iii)

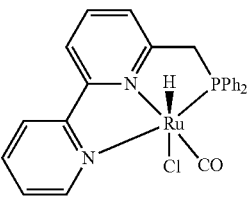

(iv)

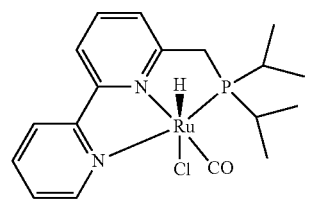

(v)

In another embodiment of the present invention, the Ruthenium complex is represented by the structure of formula A3":

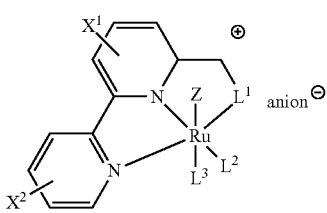

A3"

Compounds of formula A2" and formula A3" are precursors of compounds of formula A1". It is understood that any one or more of the precursors can themselves function as complexes in the process of the present invention.

The Ruthenium complexes of formulae A1", A2", A3", B1", B2", C1", C2", (iv), (v) and (vi), may be prepared in accordance with the methods described in WO 2012/052996 (U.S. Pat. No. 9,045,381), the contents of which are incorporated by reference herein in their entirety.

Processes for Preparing Ruthenium Complexes

Also encompassed by the present invention are processes for preparing the Ruthenium complexes of the present invention, and intermediates used in these processes.

It is understood that complexes of formula A2 are precursors of the complexes of formula A1, wherein complex A1 is obtained by treatment of complex A2 with a base. One equivalent of the base deprotonates the benzylic hydrogen from complex A2, while another base equivalent deprotonates the amine nitrogen, leading to a dearomatized structure of formula A1. Thus, in one embodiment, the present invention relates to a process for preparing a Ruthenium complex represented by the structure of formula A1 by reacting a Ruthenium complex of formula A2 in the presence of at least 2 equivalents of a base relative to the metal complex (Scheme 24):

Scheme 24

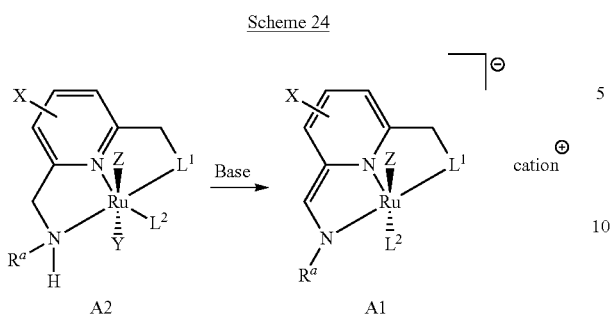

wherein $L^1$, $L^2$, X, Y and $R^a$ are defined as described above.

One particular embodiment of said process comprises preparing a Ruthenium complex represented by the structure of formula 4 from a precursor of formula 1 (Scheme 25):

Scheme 25

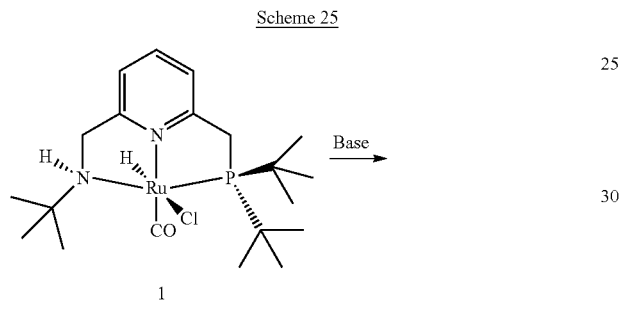

Alternatively, complex A3 can also be used as a catalyst in the processes of the present invention. In this case, treatment of compound A3 with a base yields a compound of formula A4:

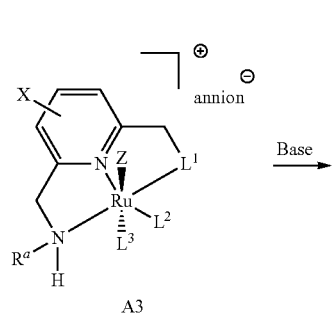

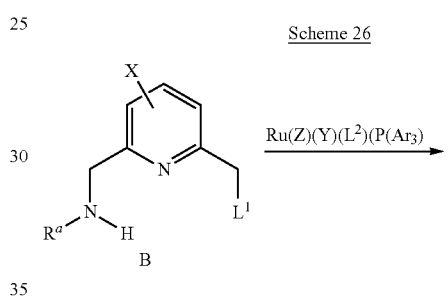

Compound A4 is also a novel catalyst that can be used in any of the processes of the present invention as described herein.

In another embodiment, the present invention relates to a process for preparing a Ruthenium complex represented by the structure of formula A2 by reacting a precursor of formula B with a Ruthenium reagent represented by the structure $Ru(Z)(Y)(L^2)(P(Ar)_3)$

Scheme 26

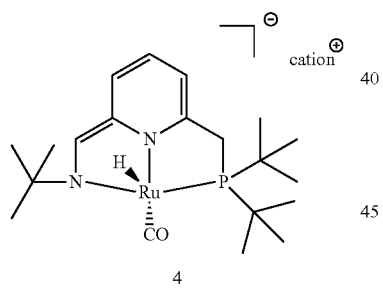

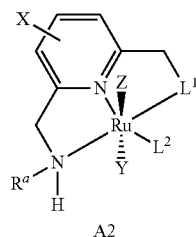

wherein Ar is phenyl or an alkyl-substituted phenyl.

In one particular embodiment, the process comprises the step of reacting a precursor of formula B' with $Ru(H)Cl(CO)(PPh_3)$ to generate a compound of formula 1, 2 or 3:

Scheme 27

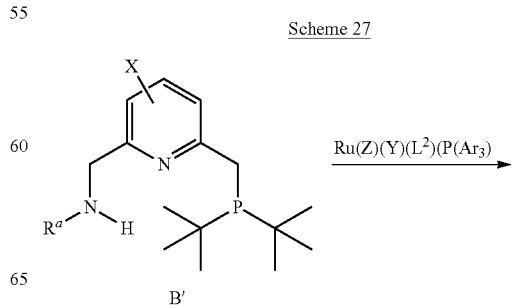

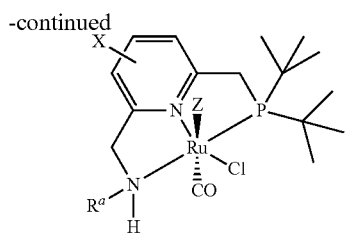

wherein $R^a$ is t-butyl (compound 1), isopropyl (compound 2) or benzyl (compound 3).

Also encompassed by the present invention are certain intermediate compounds and their use in the preparation of the Ruthenium complexes of the present invention. For example, compounds of formula B are novel intermediates that represent a separate embodiment of the present invention.

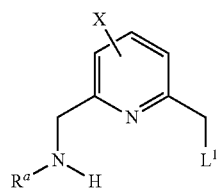

B wherein, $L^1$ is selected from the group consisting of phosphine ($PR^bR^c$), phosphite $P(OR^b)(OR^c)$, phosphinite $P(OR^b)(R^c)$, amine ($NR^bR^c$), imine, oxazoline, sulfide ($SR^b$), sulfoxide ($S(=O)R^b$), heteroaryl containing at least one heteroatom selected from nitrogen and sulfur; arsine ($AsR^bR^c$), stibine ($SbR^bR^c$) and a N-heterocyclic carbene represented by the structures:

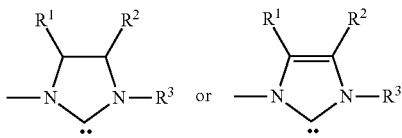

$R^a$ is H, alkyl, cycloalkyl, aryl, heterocyclyl, heteroaryl, alkylcycloalkyl, alkylaryl, alkylheterocyclyl or alkylheteroaryl; and X represents zero, one, two or three substituents independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety.

The disclosures of all cited references are incorporated by reference as if fully set forth herein.

The principles of the present invention are demonstrated by means of the following non-limiting processes.

EXAMPLES

Example 1: Preparation of Ruthenium Complexes

Three different PNN—H ligands bearing substituents R=tert-butyl (L1), isopropyl (L2) and benzyl (L3) were synthesized by reaction of 2-(ClCH$_2$)-6-($^t$Bu$_2$P(BH$_3$)CH$_2$) pyridine[3] with the corresponding amines viz. tert-BuNH$_2$, ipr-NH$_2$, and benzylamine respectively (Scheme 28). The amines were used as solvents in excess to prevent over-alkylation on the nitrogen. The corresponding ruthenium complexes were obtained in good yields (85-90%) by reacting the corresponding PNN—H ligands with Ru(H)Cl(CO)(PPh$_3$)$_3$ in THF at 65° C. (Scheme 28).

Scheme 28. Synthesis of PNN-H ligands and their corresponding Ru (II) complexes.

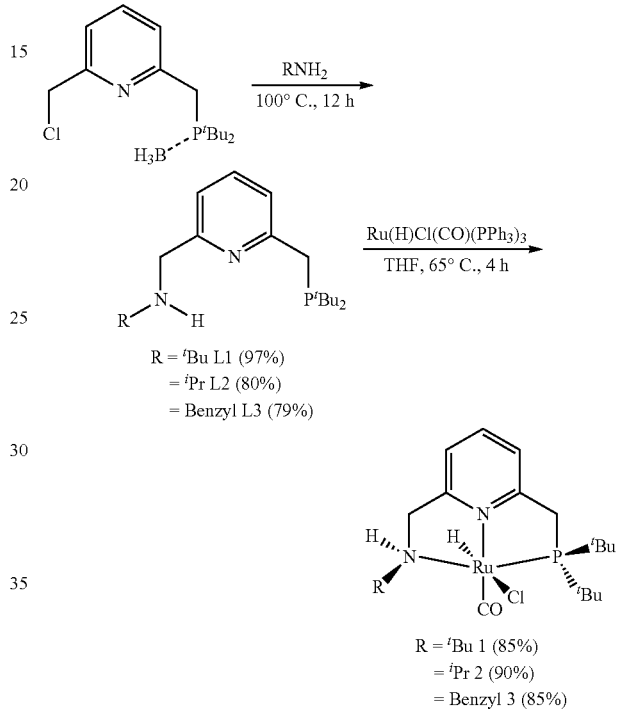

The fully characterized complexes 1-3 give rise to a singlet around 109.0 ppm in the $^{31}P\{^1H\}$ NMR spectrum. In $^1H$ NMR, the hydride bound to Ru appears as a doublet around −15.0 ppm (d, $J_{HP}$~13.0 Hz). The inequivalent geminal benzylic methylene protons attached to phosphorus appear in all cases as a doublet of doublets around 3.5 ppm and 3.42 ppm. The methylene protons attached to N resonate further downfield in the region 4.7-4.3 ppm. The carbonyl carbon in the $^{13}C\{^1H\}$ NMR spectrum exhibits the most downfield shift resonating around 208.0 ppm ($J_{CP}$~16.0 Hz) with a characteristic doublet. In the IR spectra, the carbonyl group absorbs in the range v(CO)=1898-1896 cm$^{-1}$, indicating a slightly higher back-bonding than in the analogous complex RuPNN-Et$_2$ (v(CO)=1901 cm$^{-1}$) previously disclosed (1c, U.S. Pat. No. 8,178,723).

Figure 2:
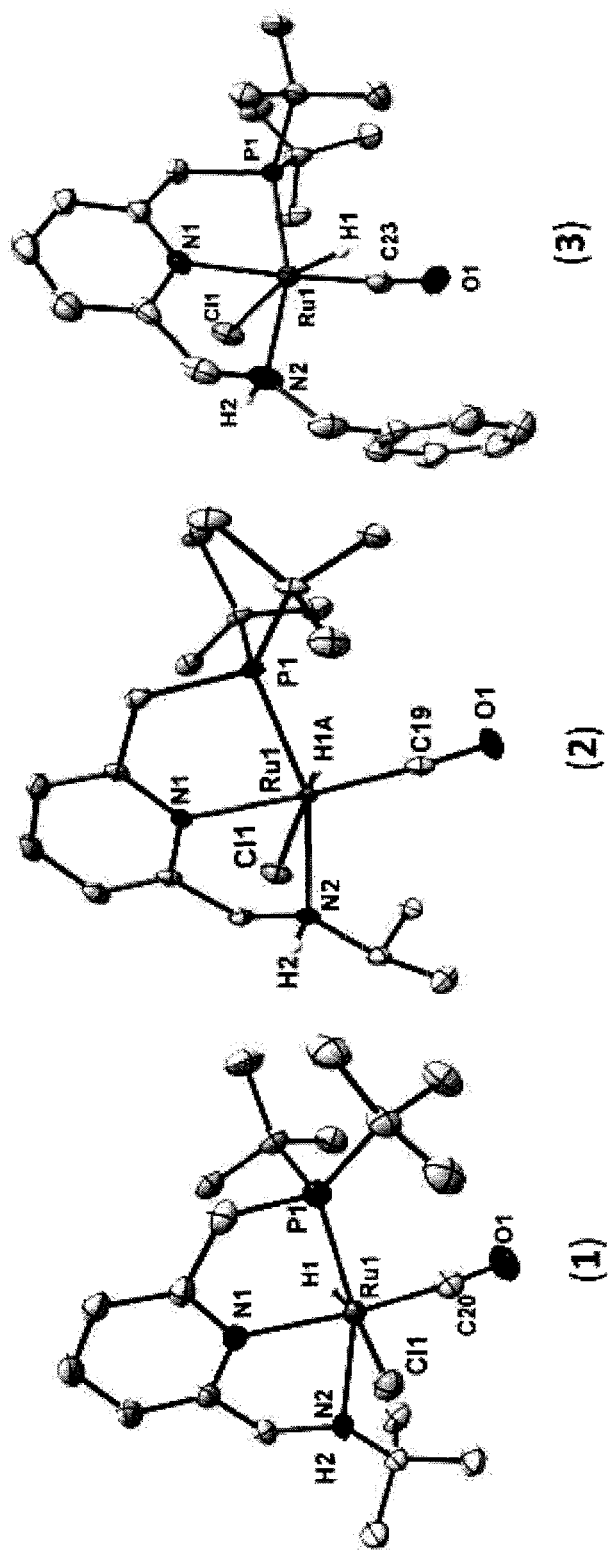
FIG. 2: shows the X-ray structure of Ruthenium complexes (1)-(3). Hydrogen atoms are omitted for clarity.

Single crystals suitable for X-ray diffraction of complexes 1, 2 and 3 were obtained by slow diffusion of pentane into concentrated solutions of the complexes in CH$_2$Cl$_2$, similar to the structure of RuPNN-Et$_2$ [hang, J.; Leitus, G.; Ben-David, Y.; Milstein, D. J. Am. Chem. Soc. (2005), 127, 10840]. These complexes also exhibit a distorted meridional octahedral structure with phosphorus, carbonyl and chloride atoms trans to the amine nitrogen, pyridine and hydride respectively. In all cases the substituents attached to nitrogen are equatorially disposed due to the steric hindrance on either side of the N1-Ru—N2 plane. The perspective views of the complexes are shown in FIG. 2. Compared to the RuPNN-Et$_2$, the distances of the chelating atoms to the metal were similar except for the distance of the amine nitrogen. Judging from their bond distances, the sec-amine coordinated ligands—of complexes 1-3 are bound significantly more strongly, with Ru—N bond distances shorter by approximately 0.5 Å. However these distances are in the expected range when compared to the reported sec-amine coordinated pincer complex Ru$^{(II)}$(2-(iPr$_2$PC$_2$H$_4$NHCH$_2$—) pyridine) [Spasyuk, D.; Smith, S.; Gusev, D. G. *Angew. Chem. Int. Ed.* (2012), 51, 2772-2775].

Next, the reactivity of 1 with a base was explored. It was formerly observed that with the analogous RuPNN-Et$_2$, addition of an equivalent of base leads to deprotonation of the benzylic phosphine arm, with concomitant de-aromatization of the pyridine based pincer group. In the case of the sec-amine coordinated complex 1, where the coordinated amine proton is of enhanced acidity (as compared with non-coordinated amine), a competition between the benzylic arm and the N—H group is expected.

Figure 3:
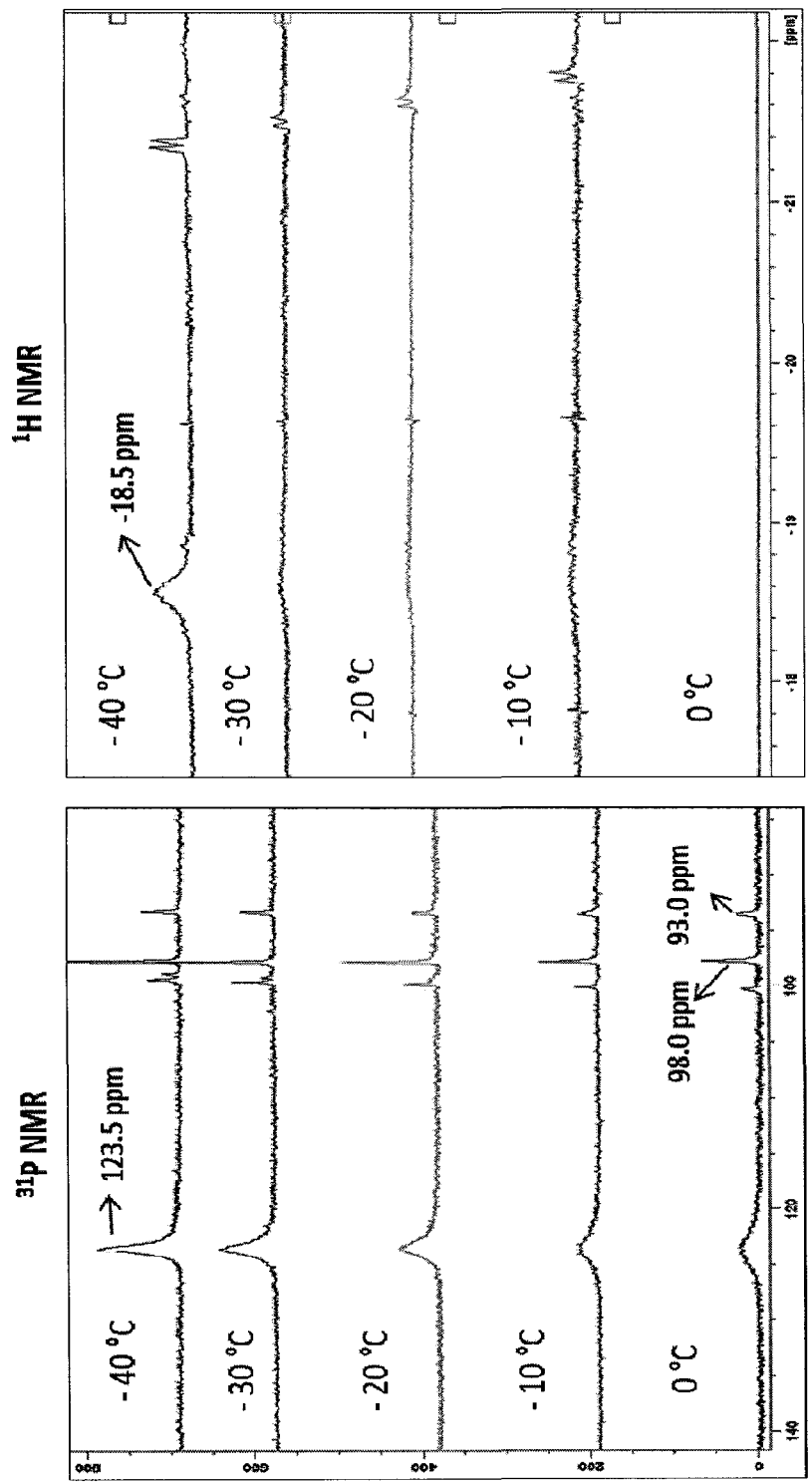
FIG. 3: Cooling a reaction mixture of 1 with 2.2 equiv. of KHMDS added at RT in THF, depicting the sharpening of the signal at 123.5 ppm in $^{31}P\{^1H\}$ NMR and −18.5 in $^1H$ NMR.
Figure 4:
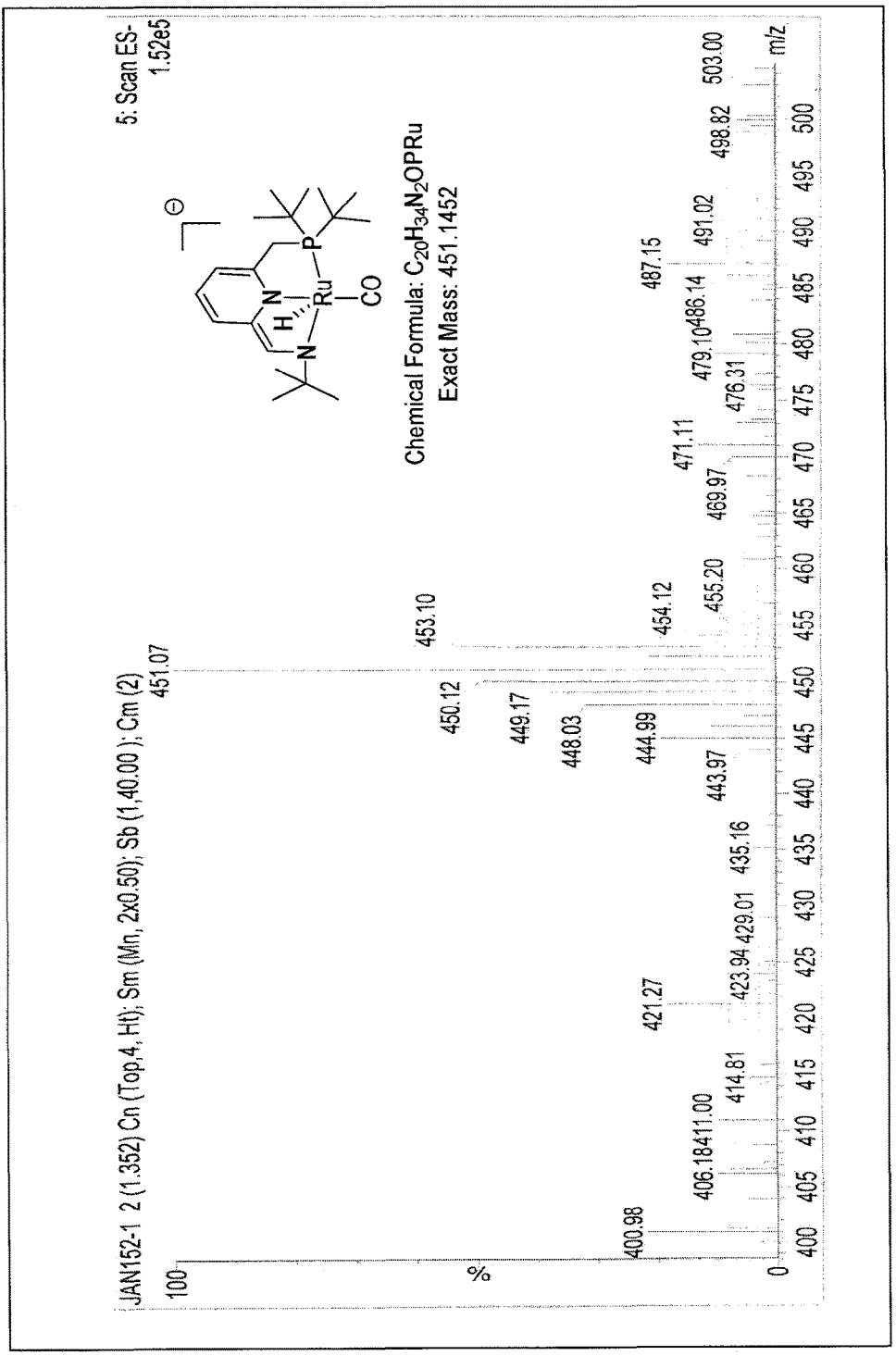
FIG. 4: ESI-MS of product obtained by reaction of complex 1 with 1.2 equiv. of KHMDS in THF at RT (i.e., complex 4 (cation=K⁺)).

Addition of 1.2 equiv. of either potassium bis(trimethylsilyl)amide (KHMDS) or potassium tert-butoxide (KO$^t$Bu) to 1 in THF at RT leads to two signals at 98.0 ppm and 93.0 ppm in the $^{31}$P{$^1$H} NMR spectrum with complete disappearance of the starting material. However, isolation of the products from the mixture was unsuccessful. It was observed that with time, upon standing, the intensity of both the signals in the reaction mixture decreased, leading to a violet precipitate from an initially brown solution. The same phenomenon was also seen with incremental addition of base from 0.5 equiv. to 2.2 equivalent of base. Surprisingly, the resultant violet product thus obtained with either 1.1 or 2.2 equiv. was silent in both $^{31}$P{$^1$H}NMR and $^1$H NMR at RT. However, when 1 was reacted with 2.2 equiv. of KHMDS in a NMR tube at RT and then cooled to −40° C. stepwise, it showed a new broad signal at 124.0 ppm in the $^{31}${$^1$H}NMR spectrum with a corresponding hydride signal at −18.5 ppm in $^1$H NMR (FIG. 3). This signal was tentatively assigned to the anionic complex resulting by deprotonation of both the amine and one of the methylene protons, even though the broadness of the signal precluded complete NMR characterization. Mass (ES$^-$) spectrum recorded for this air-sensitive violet product however matched with that of the expected anionic complex, supporting this assignment (FIG. 4). The structure assigned to this complex is represented below (i.e., complex 4 wherein cation=K$^+$).

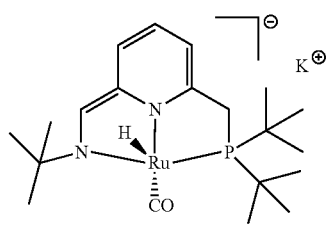

4'

Figure 5:
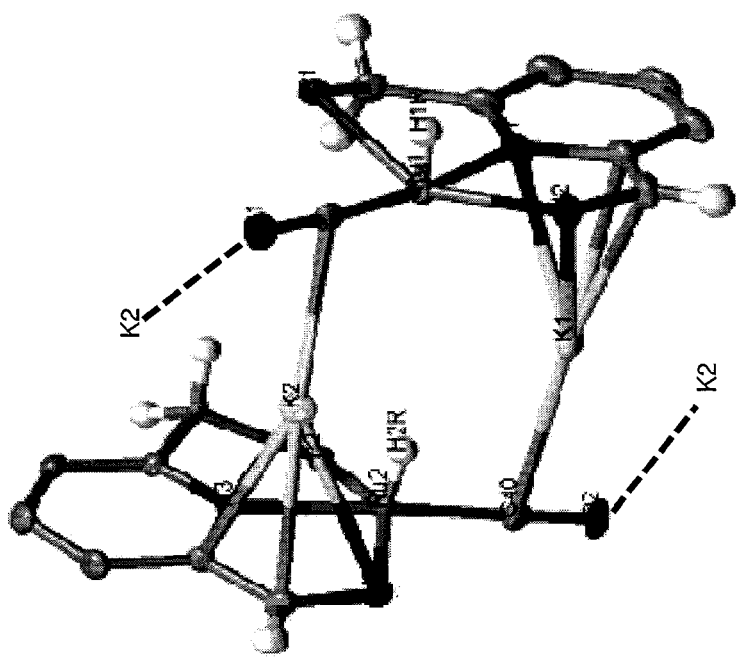
FIG. 5: shows the X-ray structure of Ruthenium complex 4 (cation=K⁺) Selected hydrogen atoms and K⁺ counter cation omitted for clarity. Right: Section of the unit cell showing the connection with K⁺. Substituents on phosphorus and nitrogen are omitted for clarity. Selected bond distances (Å) and angles (°): Ru1-H1R 0.95(5); Ru2-H2R 1.00(4), Ru1-C20 1.816(4); Ru2-C40 1.827(4), Ru1-N1 2.061(3); Ru2-N4 2.069(3), Rut-N2 2.063(3); Ru2-N3 2.059 (3), Ru1-P1 2.2581(10); Ru2-P2 2.2623(10). N1-Ru1-H1R 82(3); N3-Ru2-H2R 98(2), N2-Ru1-H1R 89(2); N4-Ru2-H2R 107(2), N2-Ru1-P1 145.71(10); N4-Ru2-P2 150.33(9), N1-Ru1-C20 173.26(15); N3-Ru2-C40 171.49(15).
Figure 5:
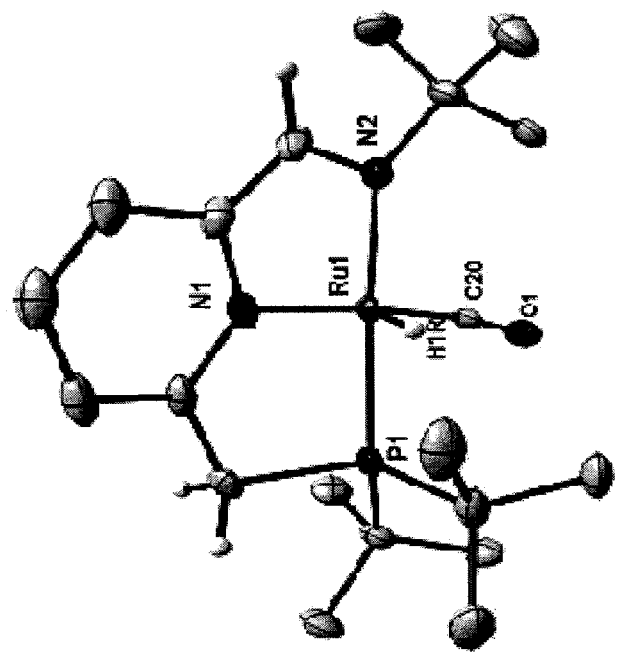

Violet crystals suitable for X-ray diffraction were obtained from a mixture of THF and ether. As expected, it revealed a double deprotonated enamido monoanionic complex with K$^+$ as counter cation, forming a distorted square-pyramidal geometry with the hydride located at the apical position (Ru1-H1R 0.95(5) Å). The perspective views of the complex are shown in FIG. 5. Contrary to the deprotonation of the P-arm methylene protons, as previously observed in the de-aromatized forms of RuPNN-Et$_2$, [Zhang, J.; Leitus, G.; Ben-David, Y.; Milstein, D. *J. Am. Chem. Soc.* (2005), 127, 10840]. C—H deprotonation took place on the N-arm, as clearly indicated by the short Csp$^2$-Csp$^3$ bond distance of 1.371 Å of the N-arm and the presence of only one C—H bond. In addition, the absence of proton attached to nitrogen unequivocally indicates that overall double deprotonation took place. The other bond distances fall in the normally expected ranges. From the molecular packing, it appears that two successively independent Ru pincer molecules are disposed roughly at 120° to each other and are connected to each other by potassium ions, which bridge between the deprotonated amine arm and the carbonyl carbon.

A change of base was attempted. Reaction of 1 with KH (2.5 equiv.) in THF at RT resulted in the formation of the violet enamido anionic complex 4' within 18 h (Scheme 29):

Scheme 29. Preparation of the monoanionic complex 4' by double deprotonation of 1.

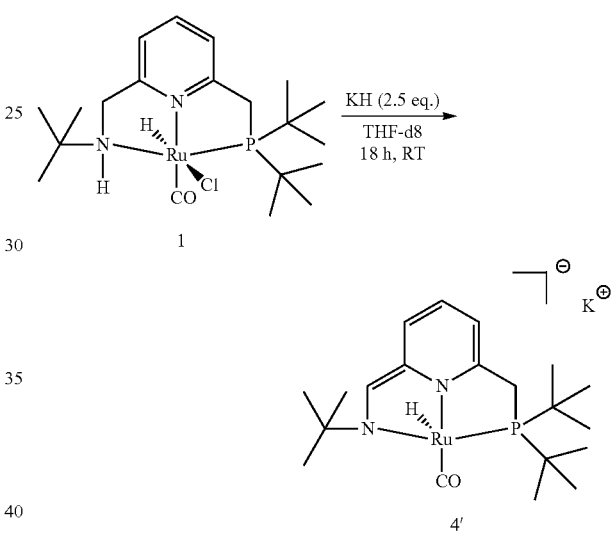

Figure 6:
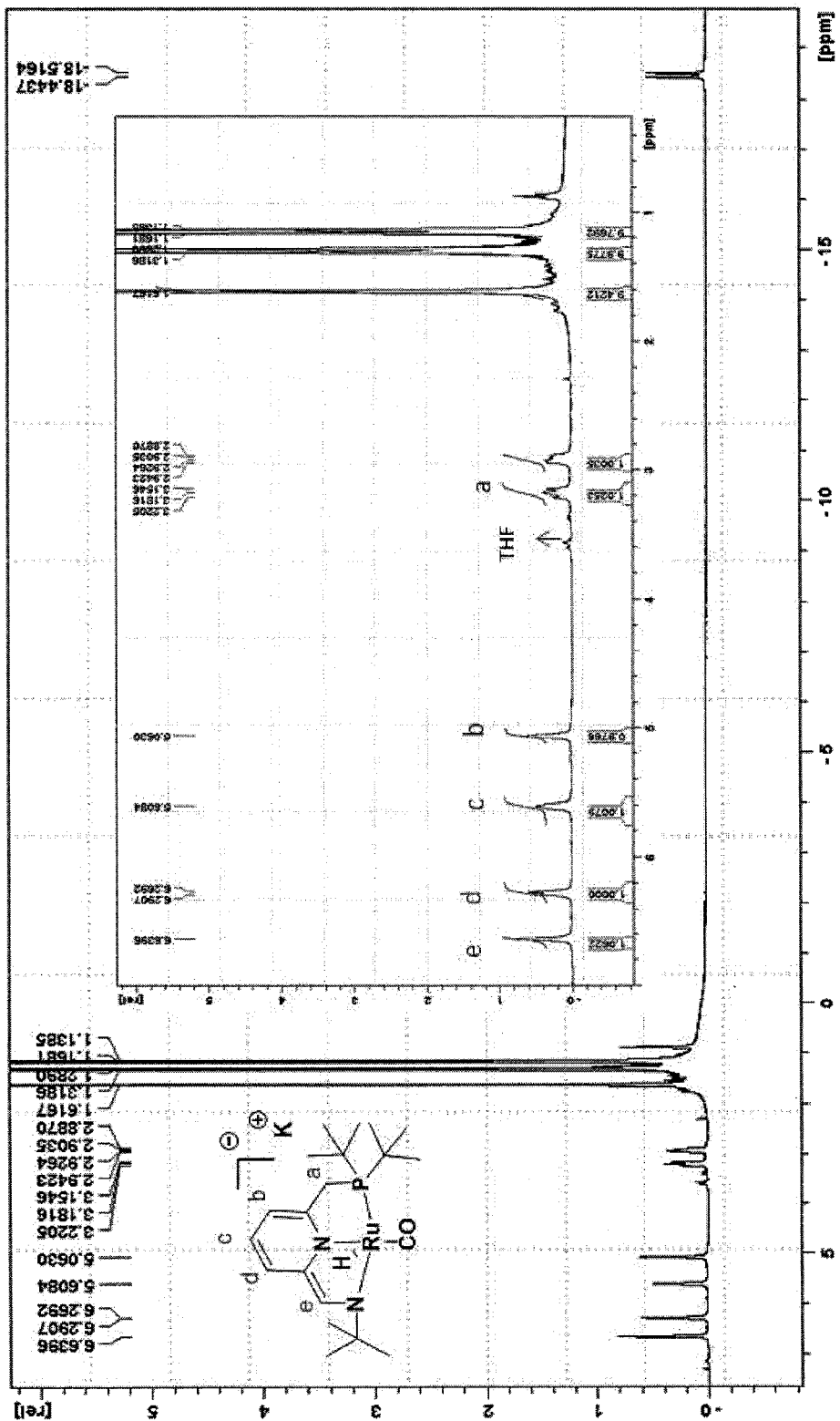
FIG. 6: $^1H$ NMR spectrum of Ruthenium complex 4 (cation=K⁺) in THF-d8 after 18 h at RT.
Figure 7:
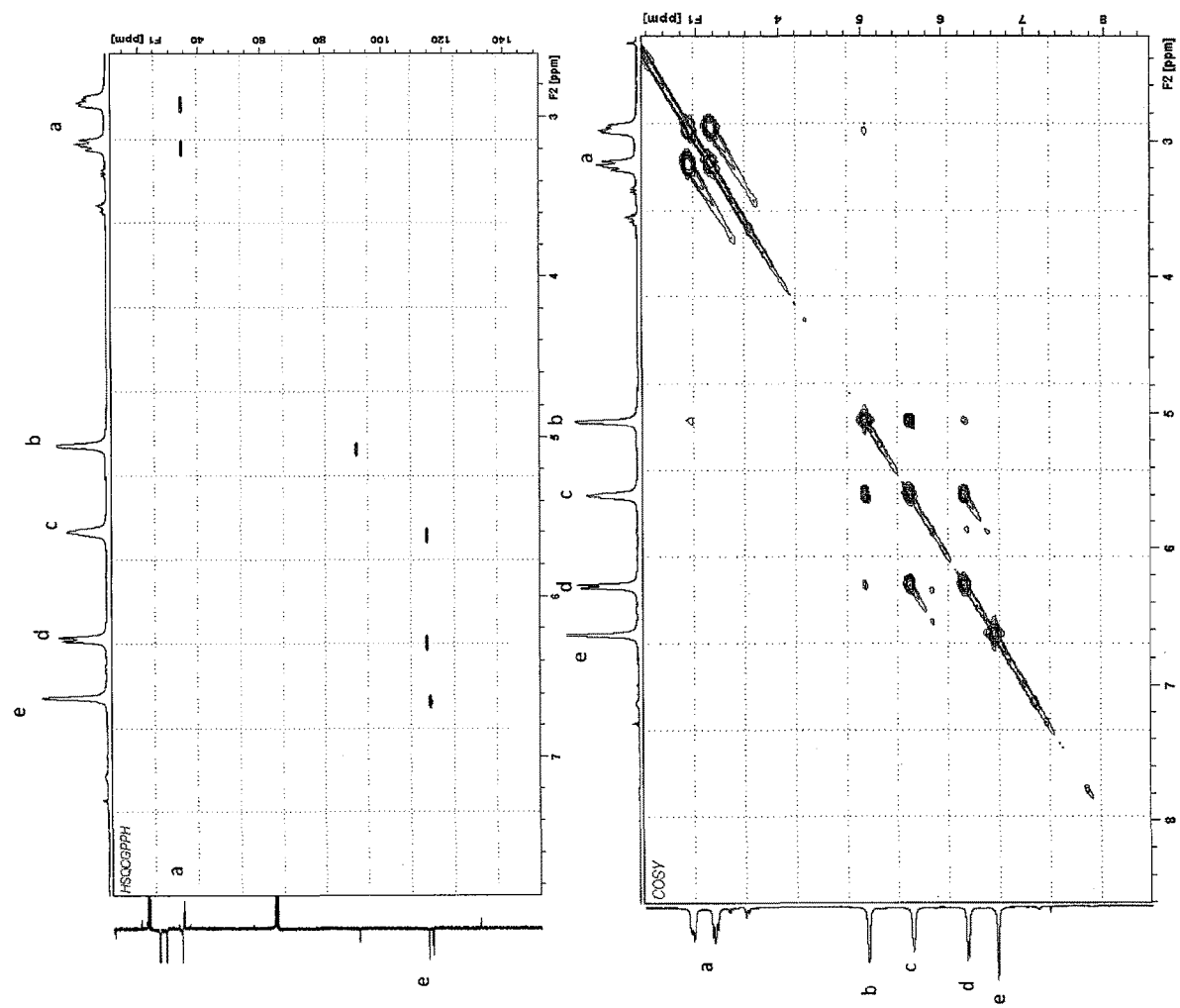
FIG. 7: Partial HSQC and COSY spectrum of 4 (cation=K⁺) in THF-d8 after 18 h.
Figure 7:
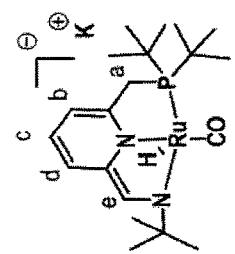

Monitoring the progress of the reaction at early intervals reveals the same set of intermediates namely the de-aromatized intermediate and the amido intermediate, finally leading to the violet precipitate, showing in the $^{31}$P NMR at 124.0 ppm and hydride at −18.5 ppm in the $^1$H NMR (FIG. 6). The $^1$H NMR reveals that the aromatic ring protons have shifted upheld (5.0-6.2 ppm) due to the de-aromatization. The enamino proton resonates most downfield at 6.6 ppm (FIG. 7).

Example 2: Dehydrogenative Coupling of Primary Alcohols to Esters

Examples of processes involving the dehydrogenative coupling of primary alcohols to the corresponding esters are shown in Scheme 30 and Tables 1 and 2. Initial catalytic experiments with hydridochloride complexes 1, 2 or 3 in the presence of varying equivalents of base suggested that they can be potentially superior to RuPNN-Et$_2$ or RuPNN-Bipy for dehydrogenative esterification of alcohols under mild conditions of benzene reflux. Typically, with RuPNN-Et$_2$ or RuPNN-Bipy, good conversions were achieved under the conditions of toluene reflux [Zhang, J.; Leitus, G.; Ben-David, Y.; Milstein, D. *J. Am. Chem. Soc.* (2005), 127, 10840]. Optimization experiments (Table 1) with 1, suggested that the best catalytic activity can be achieved by the use of about 2.0 to 2.5, preferably 2.2 equiv. of base with respect to the catalyst. This observation is in line with the hypothesis that the double-deprotonated anionic complex is fully generated with 2.2 equiv. of base and is primarily responsible for improved catalytic activity. All the three complexes 1-3 showed similar superior activity for dehydrogenative esterification reactions (Table 1). The isolated monoanionic enamido complex 4' was also an excellent catalyst for the dehydrogenative coupling of alcohols to esters. Thus, conversion of 1-hexanol to hexyl hexanoate reached completion in 1 h under toluene reflux without the need of base (Table 1, entry 8). Among the various pre-catalysts synthesized (1-3), the one with benzyl substituent on the amine nitrogen (3) was more active than 2 which in turn was better than 1 (Table 1, entries 4-6).

Employing 3 as the pre-catalyst under the optimized conditions (0.1 mol % complex and 2.2 equiv. of base, with respect to the catalyst), milder and near room-temperature conditions for esterification were attempted. Surprisingly, 3 was able to catalyze esterification of benzyl alcohol to benzyl benzoate in diethyl ether (b.p. 35° C.) as solvent. While RuPNN-Et$_2$ and RuPNN-Bipy showed less than 1% conversion, catalyst 3 yielded 37% of benzyl benzoate at the end of 40 h (Table 2). Hexyl hexanoate was quantitatively obtained after 96 h and 2-methoxyethanol required 6 days for near quantitative conversion in diethylether reflux. Conversion of the electron deficient trifluoroethanol proceeded smoothly giving 95% yield in 40 h. Linear branched alcohols such as 2-methylbutanol also furnished 72% yield of corresponding ester at the end of 40 h. Vigorous reflux under the flow of argon to drive out the H$_2$ generated was important for the success of the reaction.

TABLE 1

Esterification experiments with mainly benzene as solvent to compare the effectiveness of Ruthenium complexes 1, 2, 3 and 4'.

| Entry | Cat. | Solvent | Base equiv. (w.r.t cat.) | Bath temp (° C.) | Time (h) | Hexanol (%) | Ester (%) |
|---|---|---|---|---|---|---|---|
| 1 | 1 | C$_6$H$_6$ | 1.1 | 120 | 1.0 | 78 | 22 |
| 2 | 2 | C$_6$H$_6$ | 1.1 | 120 | 1.0 | 80 | 20 |
| 3 | 3 | C$_6$H$_6$ | 1.1 | 120 | 1.0 | 22 | 78 |
| 4 | 1 | C$_6$H$_6$ | 2.1 | 120 | 1.0 | 54 | 46 |
| 5 | 2 | C$_6$H$_6$ | 2.1 | 120 | 1.0 | 10 | 89 |
| 6 | 3 | C$_6$H$_6$ | 2.1 | 120 | 1.0 | 3 | 97 |
| 7 | 3 | neat | 2.1 | 45 | 72 | 58 | 42 |
| 8 | 4' | toluene | — | 130 | 1 | <1 | 97 |

Yields by GC, m-xylene as internal standard

Scheme 30

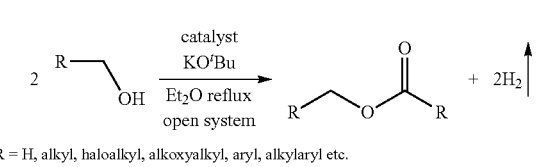

R = H, alkyl, haloalkyl, alkoxyalkyl, aryl, alkylaryl etc.

TABLE 2

Acceptorless dehydrogenative coupling of primary alcohols at 35° C. with diethylether as solvent.

| Entry | Alcohol | Ester | Catalyst | Time | Pdt. yield (%) |
|---|---|---|---|---|---|
| 1 | benzyl alcohol | benzyl benzoate | RuPNN—Et$_2$ | 40 h | <1 |
|   |   |   | RuPNN—Bipy | 40 h | <1 |
|   |   |   | 3 | 40 h | 37 |
|   |   |   |   | 6 d | 57 |
| 2 | 4-methoxybenzyl alcohol | 4-methoxybenzyl 4-methoxybenzoate | 3 | 40 h | 56 |
| 3 | 1-hexanol | hexyl hexanoate | 3 | 15 h | 41 |
|   |   |   |   | 4 d | 97 |
| 4 | 3-methyl-1-butanol | isoamyl isovalerate | 3 | 40 h | 60 |
| 5 | 2-methylbutanol | 2-methylbutyl 2-methylbutanoate | 3 | 40 h | 72 |

TABLE 2-continued

Acceptorless dehydrogenative coupling of primary alcohols at 35° C. with diethylether as solvent.

| Entry | Alcohol | Ester | Catalyst | Time | Pdt. yield (%) |
|---|---|---|---|---|---|
| 6 | MeO-CH₂CH₂-OH | MeO-CH₂-C(=O)-O-CH₂CH₂-OMe | 3 | 40 h<br>6 d | 41<br>97 |
| 7 | F₃C-CH₂-OH | F₃C-CH₂-O-C(=O)-CH₂-CF₃ | 3 | 40 h | 95 |

Reaction conditions: 5.0 mmol substrate, 0.1 mol % of catalyst, KO'Bu (0.22 mol %), 3.0 mL diethyl ether, bath temperature 45° C., open system under Ar flow with cold water circulation. Yields were determined by GC, m-xylene was used as internal standard.

Example 3: Hydrogenation of Esters to Alcohols

Examples of processes involving the hydrogenation of esters to the corresponding alcohols are shown in Scheme 31 and in Table 3. Hydrogenation of esters was carried out at relatively mild conditions (5.0 bar $H_2$ pressure) and at room temperature. The results show that 0.5 mol % of 3 was found to effectively catalyze the hydrogenation of hexyl hexanoate to 1-hexanol in quantitative yields at RT after 24 h (Table 3). Linear esters like methyl hexanoate and cyclohexyl hexanoate (Table 3, entries 2 and 3) were converted to their respective alcohols in quantitative yields. Here again, 2.2 equiv (1.1 mol %) of KO'Bu was found to be enough for achieving good conversions. However, in certain cases, better conversions were achieved with 1 as catalyst using 10.0 equiv. of base instead (Table 3, entries 6 and 10).

Cyclic ester like ε-caprolactone was also smoothly hydrogenated to the hexane-1,6 diol. These type of sec-amine coordinated catalysts also showed remarkable efficiency in loadings as low as 0.02 mol % and with 1.0 mol % of base at room temperature but with a higher $H_2$ pressure of 50 bar (Table 3, entries 1-3, 5, 6 and 10).

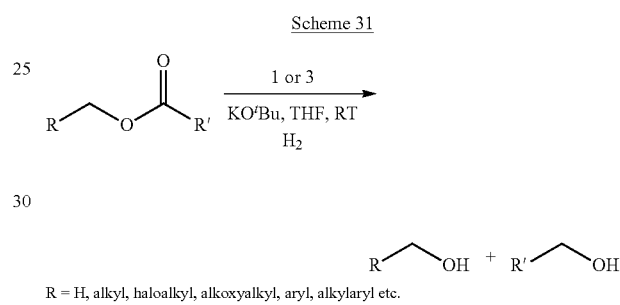

Scheme 31

R = H, alkyl, haloalkyl, alkoxyalkyl, aryl, alkylaryl etc.

TABLE 3

Hydrogenation of esters at room temperature.

| Entry | Reactant | Catalyst (mol %) | P(H₂) (bar) | Time (h) | Base mol % | Conv. (%) | Products and Yield (%) |
|---|---|---|---|---|---|---|---|
| 1 | hexyl hexanoate | 3 (0.5)<br>1 (0.02) | 5.0<br>50.0 | 24<br>72 | 1.1<br>1.0 | 99<br>96 | 1-hexanol, 99<br>1-hexanol, 96 |
| 2 | methyl hexanoate | 3 (0.5)<br>1 (0.02) | 5.0<br>50.0 | 24<br>24 | 1.1<br>1.0 | 99<br>97 | 1-hexanol, 99<br>1-hexanol, 93 |
| 3 | cyclohexyl hexanoate | 3 (0.5)<br>1 (0.02) | 5.0<br>50.0 | 24<br>24 | 1.1<br>1.0 | 99<br>94 | cyclohexanol, 98<br>1-hexanol, 98<br>cyclohexanol, 94<br>1-hexanol, 94 |
| 4 | tert-butyl acetate | 3 (0.5) | 5.0 | 24 | 1.1 | 99 | tert-butanol, 99 |
| 5 | ε-caprolactone | 3 (0.5)<br>1 (0.02) | 5.0<br>50.0 | 24<br>48 | 1.1<br>1.1 | 99<br>98 | hexane-1,6-diol, 98<br>hexane-1,6-diol, 98 |

TABLE 3-continued

Hydrogenation of esters at room temperature.

| Entry | Reactant | Catalyst (mol %) | P(H$_2$) (bar) | Time (h) | Base mol % | Conv. (%) | Products and Yield (%) |
|---|---|---|---|---|---|---|---|
| 6 | (cyclohexyl acetate) | 1 (0.5)<br>3 (0.5)<br>1 (0.02) | 5.0<br>5.0<br>50.0 | 24<br>24<br>24 | 5.0<br>1.1<br>1.0 | 93<br>70<br>93 | cyclohexanol, 93<br>cyclohexanol, 67<br>cyclohexanol, 93 |
| 7 | (bis(2,2,2-trifluoroethyl) carbonate) | 3 (0.5) | 5.0 | 32 | 1.1 | 80 | 2,2,2-trifluoro ethanol, 74 |
| 8 | (benzyl benzoate) | 3 (0.5) | 5.0 | 24 | 1.1 | 77 | Benzyl alcohol, 75 |
| 9 | (ethyl 3-phenylpropanoate) | 1 (0.5) | 5.0 | 24 | 5.0 | 96 | 3-phenylpropan-1-ol, 91 |
| 10 | (ethyl benzoate) | 1 (0.5)<br>1 (0.02) | 5.0<br>50.0 | 48<br>36 | 5.0<br>1.0 | 88<br>99 | Benzyl alcohol, 83<br>Benzyl alcohol, 99 |

Reaction conditions. 1.0 mmol substrate, 1.0 mL THF, room temperature 16-24° C. Yields were determined by GC, yields of methanol, ethanol and trifluoromethanol are not reported.

In summary, as demonstrated herein in Examples 2 and 3, this new class of PNNH complexes can further improve upon the catalytic activity of the already efficient pincer catalysts known in the art. A novel anionic double deprotonated enamido Ru(II) complex was isolated and crystallographically characterized, exhibiting outstanding catalytic activity.

Example 4: Preparation of (a) Cyclic Dipeptides from 2-Aminoethanol

The newly synthesized PNN—H complex 1, bearing an N—H group, was tested for its ability to catalyze conversion of 2-aminoethanol to glycine anhydride (GA). It was hypothesized that the presence on an NH ligand might allow for metal-ligand cooperation (MLC) via the well-known Ru-amino/Ru-amido sequence, in addition to MLC via aromatization-dearomatization of the known pincer ligand. When 1.2 equiv of base was used, 2-aminoethanol was converted to GA and linear peptide (LP), however, yields were moderate (35% GA formation and a total conversion of 71%) (Table 4, entry 1). Increasing the amount of solvent (dioxane) considerably improved reaction yields (Table 4, entry 2). Interestingly, the amount of base had a strong influence on the outcome of the reaction in this case (Table 4, entries 3-6). With 0.5 mol % of 1 and 1.2 mol % of KOtBu (2.4 equiv base relative to catalyst 1) as the catalyst system, 85% conversion of 2-aminoethanol and 60% yield of glycine anhydride were gained (Table 4, entry 4). 37 mL H$_2$ gas were collected under the optimized reaction conditions, corresponding to 83% yield of hydrogen based on the reaction of eq 2. Higher base loading (Table 4, entries 5, 6) and lower temperature (Table 4, entries 7, 8) decreased the performance of the reaction.

TABLE 4

Selected results of optimization studies for dehydrogenation of 2-aminoethanol

Scheme 32

| entry | catalyst | KO$^t$Bu (equiv to Cat.) | dioxane (mL) | conversion (%) | product$^a$ (yield %) |
|---|---|---|---|---|---|
| 1 | 1 | 1.2 | 4 | 71 | GA (35) + LP |
| 2$^b$ | 1 | 1.2 | 6 | 87 | GA (61) + LP |
| 3 | 1 | 1.8 | 4 | 72 | GA (47) + LP |
| 4 | 1 | 2.4 | 4 | 85 (83)$^c$ | GA (60) + LP |
| 5 | 1 | 4 | 4 | 85 | GA (37) + LP |
| 6 | 1 | 6 | 4 | 88 | GA (34) + LP |
| 7$^d$ | 1 | 2.4 | 4 | 78 | GA (41) + LP |

TABLE 4-continued

| | | | | | |
|---|---|---|---|---|---|
| 8[e] | 1 | 2.4 | 4 | 84 | GA (53) + LP |
| 9[f] | 1 | 2.4 | 80 | 89 (74) | GA (55) + LP |

Reaction conditions: 0.5 mol % catalyst, KOtBu (as specified in Table 4), 1 mmol 2-aminoethanol and solvent were refluxed (the actual reaction temperature was 105° C. when using dioxane as the solvent, oil bath temperature 135° C.) under a flow of argon for 12 h. Conversion determined by NMR using 1,3,5-trimethylbenzene as an internal standard. Yields determined by NMR using pyridine as an internal standard.
[a]GA, glycine anhydride; LP, linear peptides.
[b]0.75 mol % catalyst was used.
[c]$H_2$ was collected, values in parentheses are yields of hydrogen based on the reaction of Scheme S2 below.
[d]oil bath temperature 105° C.
[e]oil bath temperature 115° C.
[f]20 mmol of 2-aminoethanol was used.

The individual reactions leading to GA and LP are provided below:

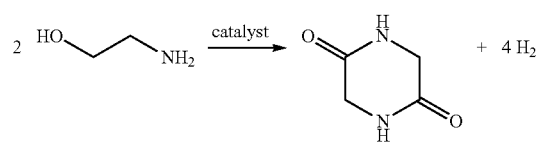

(S1)

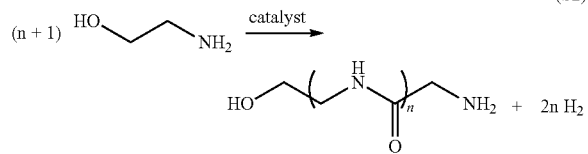

(S2)

Solvent mixtures of dioxane with other polar or non-polar solvents, including diglyme, DMF (dimethylformamide), valeronitrile, DMAC (dimethylacetamide), NMM (N-methylmorpholine) and toluene, were also tried, generally resulted in lower efficiency, although the reactions were still feasible using these conditions. Using no solvent or a very small amount of solvent resulted in lower efficiency of the dehydrogenative coupling reaction, although substantial dehydrogenation was still observed. For example, heating a mixture of 0.1 mL DMSO and 10 mmol 2-aminoethanol together with 0.5 mol % catalyst 1 and 1.2 mol % KOtBu at 150° C. for 12 in an oil bath, resulted in 60% conversion of 2-aminoethanol mostly to linear peptides and 33% yield of $H_2$ (Table 5).

TABLE 5

Dehydrogenation of 2-aminoethanol using a small amount of solvent.

| entry | solvent (mL) | conversion (%) | product (yield) |
|---|---|---|---|
| 1 | DMSO (0.1) | 60 (33)[a] | GA (trace) + LP |

Reaction conditions: 0.5 mol % catalyst 1, 1.2 equiv (to catalyst 4) of KOtBu, 10 mmol 2-aminoethanol and solvent were heated (oil bath temperature 135° C.) under a flow of argon for 12 h. Conversion and yields were determined by NMR using pyridine as an internal standard.
[a]$H_2$ was collected, values in parentheses were yields of hydrogen based on the reaction of eq S2 (assuming 100% conversion to glycine anhydride).
GA, glycine anhydride;
LP, linear peptides;
DMSO, dimethyl sulfoxide.

Example 5: Hydrogenation of Glycine Anhydride to 2-Aminoethanol

Complex 1 as well as the known complex Ru—PNN-Et$_2$ (in this Example "Complex A") were tested for the hydrogenation of glycine anhydride. At first, no product was obtained when the reaction was run under 10 bar of $H_2$ in THF using 1 mol % of either complex at 110° C. (oil bath temperature, Table 6, entries 1, 2). Applying 50 bar of $H_2$, 2 mol % complex A and 2.4 mol % KO$^t$Bu in dioxane at 110° C. resulted in quantitative yield of the linear amide 2-amino-N-(2-hydroxyethyl)acetamide (entry 3). Higher amount of base improved the reaction, with 61% yield of glycine anhydride and 34% yield of 2-amino-N-(2-hydroxyethyl) acetamide were produced when 4.8 mol % KO$^t$Bu was applied together with 2 mol % complex A (entry 4). Complex 1 showed much better catalytic activity than complex A and nearly 100% yield of 2-aminoethanol was obtained, even in a lower complex loading of 0.5 mol % and less amount of solvent (entries 5, 6). Using lower pressure of $H_2$ (20 bar) was less effective to afford 2-aminoethanol from glycine anhydride (entry 7). The mixed products of glycine anhydride and linear peptides produced by the dehydrogenative reaction (under conditions of Table 4, entry 4) could also be hydrogenated by complex 1 and 85 wt % yield was obtained under 50 bar of $H_2$ (entry 8). Higher pressure of $H_2$ failed to improve the yield (entry 9), probably because of the poor solubility of the long-chain linear peptides, which was detrimental to their hydrogenation.

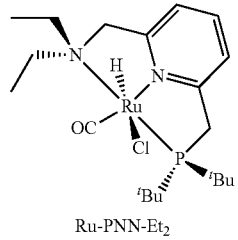

Ru-PNN-Et$_2$

TABLE 6

Selected results from the optimization studies for hydrogenation of glycine anhydride Scheme 33

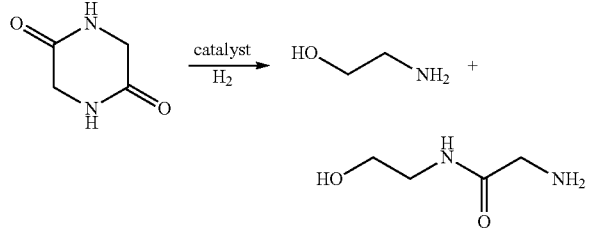

| entry | complex (mmol) | KO$^t$Bu (equiv to complex) | t (h) | substrate[a] (mmol) | $H_2$ pressure (bar) | solvent (mL) | Product[b] (yield %) |
|---|---|---|---|---|---|---|---|
| 1[c] | A (0.005) | 1.2 | 24 | GA (0.5) | 10 | THF (4) | — |
| 2[c] | 1 (0.005) | 2.4 | 24 | GA (0.5) | 10 | THF (4) | — |
| 3 | A (0.01) | 1.2 | 48 | GA (0.5) | 50 | dioxane (4) | AA (>99) |
| 4 | A (0.01) | 2.4 | 48 | GA (0.5) | 50 | dioxane (4) | AE (61), AA (34) |
| 5 | 1 (0.005) | 2.4 | 48 | GA (0.5) | 50 | dioxane (4) | AE (>99) |
| 6 | 1 (0.005) | 2.4 | 48 | GA (1) | 50 | THF (2) | AE (>99) |
| 7 | 1 (0.005) | 2.4 | 48 | GA (1) | 20 | THF (2) | AA (23) |

TABLE 6-continued

| 8 | 1 (0.0025) | 2.4 | 48 | mixture[d] | 50 | dioxane (1) | AE (85)[e] |
| 9 | 1 (0.0025) | 2.4 | 48 | mixture[d] | 70 | dioxane (1) | AE (86)[e] |
| 10 | 1 (0.05) | 2.4 | 12 | GA (5) | 70 | Dioxane (5) | AE (96), AA (4) |

Reaction conditions: complex, KO$^t$Bu, glycine anhydride, solvent and H$_2$ were heated in a 20 mL Parr apparatus at 110° C. (oil bath temperature). Yields determined by NMR using pyridine as an internal standard.

[a]GA, glycine anhydride.

[b]AA, 2-amino-N-(2-hydroxyethyl)acetamide; AE, 2-aminoethanol.

[c]100 mL Fischer-Porter tube was used.

[d]28.6 mg mixture of GA and linear peptides (produced from AE under the conditions of Table 4, entry 6) was used as substrate.

[e]wt %.

Example 6: Preparation of Amides from Alcohols and Amines

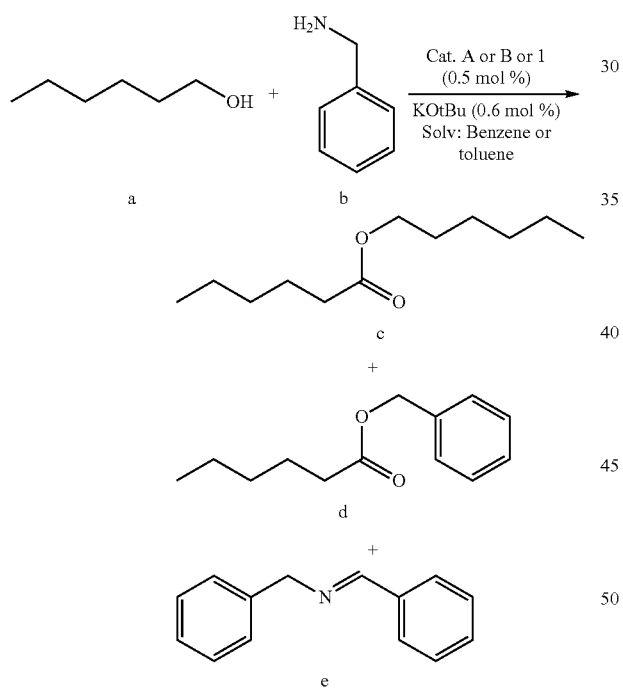

TABLE 7

Selected results from reactions of 1-hexanol and benzylamine (Scheme 34)

| Entry | Cat. | Solv. | Temp. (° C.) | Time (h) | a/% | c/% (ester) | d % (amide) | e % |
|---|---|---|---|---|---|---|---|---|
| 1 | A | Benzene | 90 | 45 | — | 38 | 67 | — |
| 2 | B | Benzene | 90 | 45 | — | 23 | 76 | 1 |
| 3 | 1 | Benzene | 90 | 45 | — | 7 | 92 | 1 |

Yields by GC with m-xylene as internal standard

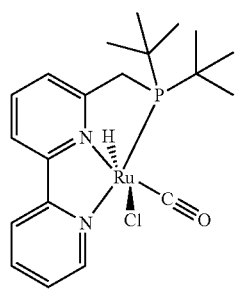

A

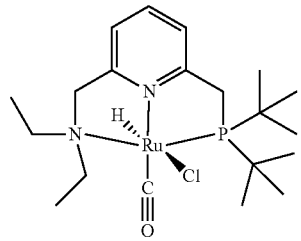

B

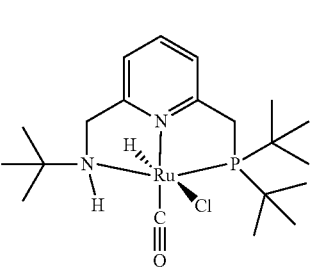

1

A = Ru-PNN-Bipy
B = Ru-PNN-Et$_2$
C = Complex 1 of the present invention

Complex 1 of the present invention as well as the known complexes Ru—PNN-Bipy (in this Example "Complex A") and Ru—PNN-Et$_2$ (in this Example "Complex B") were tested for their ability to catalyze conversion of amines and alcohols to amides in refluxing benzene. As seen in Table 7, complex 1 was superior to both complexes A and B in obtaining high yields of the desired amine product with minimal formation of the corresponding ester side product (c).

Example 7: Dehydrogenation of 2-(Methylamino)Ethanol 2-(methylamino)ethanol was reacted with Ruthenium complex 1 as detailed in Table 8:

Scheme 35. Dehydrogenation of 2-(methylamino)ethanol to N,N-dimethyl glycine anhydride (GA)

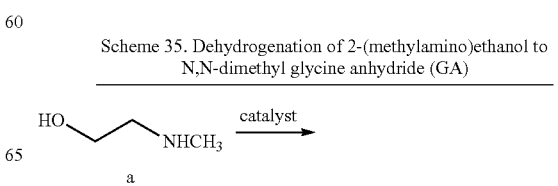

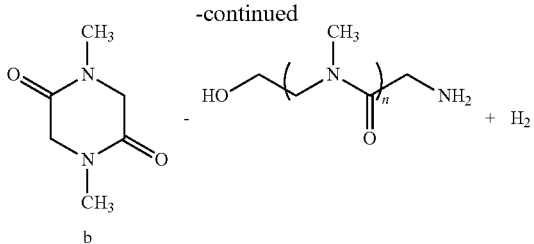

b

TABLE 8

| entry | catalyst (mol %) | a (mmol) | KO$^t$Bu (equiv to Cat.) | dioxane (mL) | conversion (%) | yield of b (%) |
|---|---|---|---|---|---|---|
| 1 | 1 (0.1) | 5 | 2.4 | 0.5 | 77 | 27 |
| 2 | 1 (0.25) | 2 | 2.4 | 0.5 | >99 | >99 |

Reaction conditions: catalyst, KO$^t$Bu (as specified in the Table), N-methylaminoethanol (as specified in the Table) and solvent were refluxed (oil bath temperature 135° C.) under argon for 24 h. Conversion and Yields determined by NMR using pyridine as an internal standard.

Cat. 1

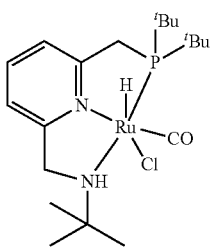

Typical Procedure for the Dehydrogenation of 2-(Methylamino)Ethanol:

In a glove box, a 25 mL Schlenk flask was charged with a stirring bar, catalyst (0.005 mmol), KO$^t$Bu (0.006-0.012 mmol), 2-(methylamino)ethanol (2 mmol) and dioxane (0.5 mL) under an atmosphere of nitrogen. The flask was taken out of the glove box, equipped with a condenser and the solution was refluxed with stirring in an open system under a flow of argon for 24 h. After cooling to room temperature, 1 mmol of pyridine was added to the crude reaction mixture as an internal standard. Then approximate 0.05 mL of the solution was dissolved in approximate 0.5 mL D$_2$O for determination of the conversion of N-methylaminoethanol and the yield of 1,4-dimethylpiperazine-2,5-dione by $^1$H NMR spectroscopy.

Example 8A: Dehydrogenative Coupling of Ethylenediamine and Ethanol

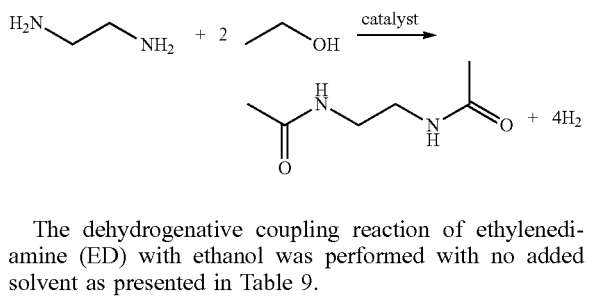

The dehydrogenative coupling reaction of ethylenediamine (ED) with ethanol was performed with no added solvent as presented in Table 9.

TABLE 9 dehydrogenative coupling conditions of ethylenediamine with ethanol.[a]

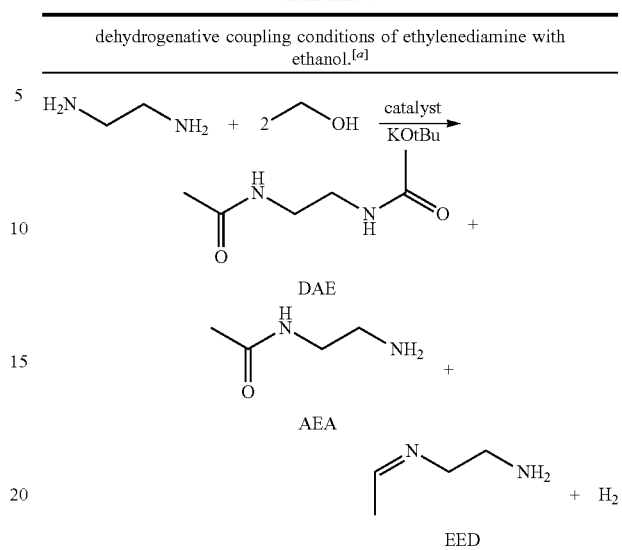

| Entry | Cat. [mmol] | ED [mmol] | E [mmol] | Solv. mL | ED conv. [%] | E conv. [%] | DAE yield [%] | AEA yield [%] | Eed yield [%] |
|---|---|---|---|---|---|---|---|---|---|
| 1 | 1 (0.01) | 15 | 20 | — | 40 | 18 | 2 | 24 | 14 |

[a]Reaction conditions: Catalyst (as specified), KO$^t$Bu (2.4 equiv relative to cat. 1), 105° C. (oil bath temperature 135° C.), reflux under Ar for 24 h.
ED = ethylenediamine, E = ethanol, DAE = N,N'-diacetylethylenediamine, AEA = N-(2-aminoethyl)acetamide, EED = N-ethylideneethane-1,2-diamine.

Example 8B: Hydrogenation of N,N-Diacetylethylenediamine (DAE) to ED and Ethanol

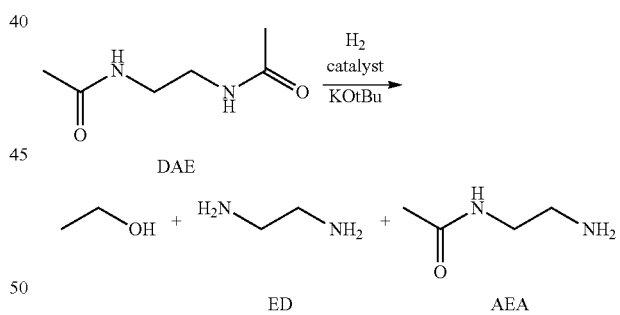

The hydrogenation of N,N'-diacetylethylenediamine (DAE) to ED and ethanol was persued as presented in Table 10.

TABLE 10 hydrogenation conditions of N,N'-diacetylethylenediamine.[a]

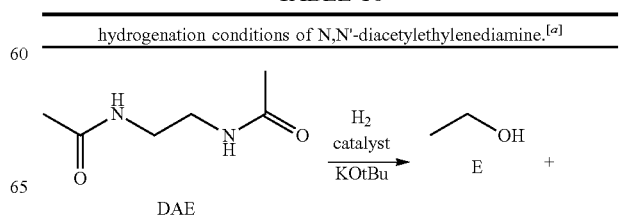

TABLE 10-continued

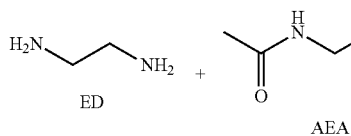

ED

AEA

| En-try | Cat. [mol %] | KOtBu [equiv to cat.] | DAE [mmol] | t [h] | Products [% yield] |
|---|---|---|---|---|---|
| 1 | 1 (0.2) | 2.4 | 1 | 48 | ED (71) + AEA (28) + E (61) |

[a]Reaction conditions: Catalyst, KO$^t$Bu, N,N'-diacetylethylenediamine, dioxane (2 mL), and H$_2$ (50 bar) were heated in a 20 mL Parr apparatus at 115° C. (oil bath temperature). Yields were determined by NMR analysis. The relatively lower yields of ethanol are probably due to the evaporation loss during the reaction and workup.

Example 9: Synthesis of Amino Acids from Amino Alcohols 2-aminoethanol was chosen as the initial reactant to test the feasibility of the reaction of converting amino alcohols to amino acids. Refluxing a water:dioxane (1:1 v/v ratio) solution containing 0.1 mol % complex (iii), 10 mmol NaOH and 5 mmol 2-aminoethanol for 24 h under an Argon atmosphere resulted in quantitative yield of the glycine sodium salt, as determined by $^1$H NMR spectroscopy (Table 9, entry 1). Applying catalyst (i) under similar conditions resulted in formation of the glycine salt in a lower yield of 73% (entry 2). Using a catalytic amount of KO$^t$Bu (1.2 equivalents relative to the catalyst), for generation of the actual catalyst (vi) in situ, with no excess base, no product was observed (entry 3). Apparently, at least a stoichiometric amount of base is required, otherwise the generated acid deactivates the catalyst. The outcome of the reaction was influenced by the amount of NaOH used; 70% yield of the glycine salt was produced when 1.1 equiv of NaOH was applied (entry 4). Glycine is an important genetic code amino acid and widely used as an additive in animal and human foods, a buffering agent in cosmetics, and an important chemical feedstock, and has many other applications. When 2-amino-1-butanol was used, 46% yield of the corresponding amino acid salt was formed, under the conditions of entry 4 (entry 5). Use of catalyst (i) led to an even lower yield of 29% (entry 6). Further optimization revealed that better results can be obtained using H$_2$O as the solvent in the absence of dioxane, leading to 70% yield of α-aminobutyric acid salt (entry 7). Changing the base from NaOH to KOH resulted in a still better yield of 77% (entry 8). The concentration of the base had a strong influence on the reaction. Thus, doubling the volume of H$_2$O resulted in a drop of the yield of α-aminobutyric acid salt to 26% (entry 9). Increasing the catalyst loading to 0.2 mol % under the conditions of entry 8 resulted in a higher yield of 89% (entry 10). Based on the results of entries 9 and 10, 0.2 mol % catalyst (iii) was applied in basic H$_2$O with higher KOH concentration, resulting in excellent yields of α-aminobutyric acid salt (entries 11, 12). α-aminobutyric acid is a key intermediate in the biosynthesis of ophthalmic acid. Employing the PNNH complex of formula (1) resulted in transformation of ethanolamine and 2-aminobutan-1-ol (entries 13, 14, respectively).

TABLE 11

Optimization studies for transformation of amino alcohols to amino acid salts

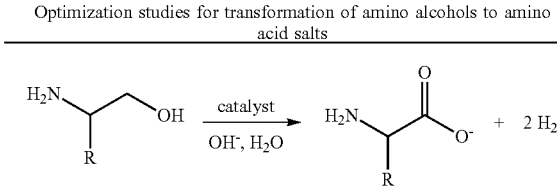

| Entry | Cat. (mol %) | R | Base (mmol) | Solvent (mL) | Conversion[a] (%) | Yield[a] (%) |
|---|---|---|---|---|---|---|
| 1 | iii (0.1) | H | NaOH (10) | H$_2$O (0.5) dioxane (0.5) | 100 | >99 |
| 2 | i (0.1) | H | NaOH (10) | H$_2$O (0.5) dioxane (0.5) | 73 | 73 |
| 3[b] | iii (0.1) | H | — | H$_2$O (0.5) dioxane (0.5) | 0 | 0 |
| 4 | iii (0.1) | H | NaOH (5.5) | H$_2$O (0.5) dioxane (0.5) | 70 | 70 |
| 5 | iii (0.1) | Et | NaOH (5.5) | H$_2$O (0.5) dioxane (0.5) | 46 | 46 |
| 6 | i (0.1) | Et | NaOH (5.5) | H$_2$O (0.5) dioxane (0.5) | 31 | 29 |
| 7 | iii (0.1) | Et | NaOH (5.5) | H$_2$O (0.5) | 70 | 70 |
| 8 | iii (0.1) | Et | KOH (5.5) | H$_2$O (0.5) | 79 | 77 |
| 9 | iii (0.1) | Et | KOH (5.5) | H$_2$O (1) | 26 | 26 |
| 10 | iii (0.2) | Et | KOH (5.5) | H$_2$O (0.5) | 90 | 89 |
| 11 | iii (0.2) | Et | KOH (5.5) | H$_2$O (0.3) | 96 | 94 |
| 12 | iii (0.2) | Et | KOH (7.5) | H$_2$O (0.5) | 98 | 95 |
| 13 | 1 (0.1) | H | NaOH (10) | H$_2$O (0.5) dioxane (0.5) | 75 | 75 |
| 14 | 1 (0.1) | Et | NaOH (5.5) | H$_2$O (0.5) dioxane (0.5) | 48 | 48 |

Reaction conditions: Catalyst (as specified in the Table), 2-aminoethanol or 2-aminobutan-1-ol (5 mmol), base (as specified in the Table) and solvent were refluxed at 125° C. (oil bath temperature) in an open system under argon for 24 h.
[a]Conversions and yields determined by NMR.
[b]0.12 mol % KO$^t$Bu was used.
R = H, Et Employing the optimized reaction conditions, the scope of the substrate amino alcohol was further explored. 2-(2-hydroxyethylamino)acetic acid salt was produced selectively in quantitative yield when diethanolamine was used as the reactant, applying water/dioxane (1:1 v/v ratio) as the solvent and catalyst (iii) (Table 10, entry 1). Employing the same reactant, similar results were obtained with catalysts 1 and (iv) (Table 11, entries 2 and 3). Reaction of 2-aminopropanol resulted in the alanine salt in quantitative yield, catalyzed by 0.1 mol % catalyst (iii) in a water/dioxane solution (entry 2). L-alanine is second only to leucine as the building block of proteins; because deamination of alanine leads to a stable alkyl free radical, it is also used in radiotherapy. Reaction of N-methylethanolamine resulted in quantitative yields of sarcosine salts using either a mixture of water/dioxane or water solely as the solvent (entry 3). Sarcosine is ubiquitous in biological materials and used in manufacturing biodegradable surfactants and toothpastes and has been investigated to treat mental illness and Major Depression. Under the same conditions, N,N-dimethylethanolamine was transformed to the corresponding dimethylglycine salts in 95% and 93% yields, respectively (entry 4). The reaction efficiency was not influenced by the steric hindrance of substituted amine groups; both N-isopropylethanolamine and N-tert-butylethanolamine produced the corresponding amino acid salts in excellent yields (entries 5 and 6). And in the case of N-tert-butylethanolamine, quantitative yield was observed when 0.5 mol % catalyst was used. However, when 2-amino-3-methyl-1-butanol was tried as a substrate, only 25% yield of leucine salt was observed, catalyzed by 0.2 mol % catalyst (iii) in ca. 18M KOH aqueous solution. The yield was increased by increasing the catalyst loading to 1 mol % and using water/dioxane (1:1 v/v ratio) as the solvent, resulting in 94% yield of the leucine salt (entry 7). Similar reaction conditions but less catalyst loading of 0.5 mol % also led to excellent yield of the proline salt when prolinol was applied (entry 8). When 2-amino-3-phenyl-1-propanol and 2-amino-2-phenyl-1-ethanol were tested, the phenylalanine salt and 2-phenylglycine salt were both produced in quantitative yields (entries 9, 10). Phenylalanine is a natural amino acid and performs as a precursor for many essential bioactive compounds, such as tyrosine, dopamine, norepinephrine, epinephrine, and the skin pigment melanin; it is also used in food and drinks and sold as a nutritional supplement. Significantly, γ-amino alcohols were also good substrates for the reaction. Thus, 3-aminopropanol reacted smoothly under the same conditions as 2-aminopropanol and offered the β-alanine salt in 94% yield (entry 11). β-alanine is the rate-limiting precursor of carnosine, which has a number of antioxidant properties and acts as an antiglycating agent. Applying N,N-dimethyl-3-aminopropanol as the substrate yielded 96% of the corresponding amino acid salt (entry 12). When 3-amino-3-phenyl-1-propanol was tested, 72% yield of 3-amino-3-phenyl-1-propanic acid salt was observed, catalyzed by 0.5 mol % catalyst (iii) (entry 13). 2-Aminobenzyl alcohol also performed well under similar conditions and 94% yield of anthranilic acid salt was produced (entry 14).

TABLE 12

Substrate scope of the transformation of amino alcohols to amino acid salt

| Entry | Reactant | Product and yield (%) |
|---|---|---|
| 1 | HOCH2CH2NHCH2CH2OH | HOCH2CH2NHCH2COO⁻  >99[a] |
| 2 | 2-aminopropanol | alanine salt  >99[b] |
| 3 | N-methylethanolamine | sarcosine salt  >99[b], >99[c] |
| 4 | N,N-dimethylethanolamine | N,N-dimethylglycine salt  95[b], 93[c] |
| 5 | N-isopropylethanolamine | N-isopropylglycine  93[b] |
| 6 | N-tert-butylethanolamine | N-tert-butylglycine  95[b], >99[d] |
| 7 | 2-amino-3-methyl-1-butanol | leucine salt  25[c], 94[e] |
| 8 | prolinol | proline salt  >99[f] |
| 9 | 2-amino-3-phenyl-1-propanol | phenylalanine salt  >99[d] |
| 10 | 2-amino-2-phenyl-1-ethanol | 2-phenylglycine salt  >99[g] |
| 11 | H2N(CH2)3OH | β-alanine salt  94[b] |
| 12 | N,N-dimethyl-3-aminopropanol | corresponding salt  96[b] |
| 13 | 3-amino-3-phenyl-1-propanol | 3-amino-3-phenyl-1-propanic acid salt  72[h] |
| 14 | 2-aminobenzyl alcohol | anthranilic acid salt  94[d] |

Reaction conditions: Reaction mixtures were refluxed at 125° C. (oil bath temperature) under Argon for 24 h. Yields determined by NMR.
[a]0.2 mol % Cat. (iii), 2.5 mmol reactant, 10 mmol NaOH, 0.5 mL H2O and 0.5 mL dioxane were used.
[b]0.1 mol % Cat. (iii), 5 mmol reactant, 10 mmol NaOH, 0.5 mL H2O and 0.5 mL dioxane were used.
[c]0.2 mol % Cat. (iii), 5 mmol reactant, 5.5 mmol KOH and 0.3 mL H2O were used.
[d]0.5 mol % Cat. (iii), 2 mmol reactant, 7.5 mmol KOH, 0.5 mL H2O were used.
[e]1 mol % Cat. (iii), 1 mmol reactant, 10 mmol NaOH, 0.5 mL H2O and 0.5 mL dioxane were used.
[f]0.5 mol % Cat. (iii), 1 mmol reactant, 10 mmol NaOH, 0.5 mL H2O and 0.5 mL dioxane were used.
[g]1 mol % Cat. (iii), 1 mmol reactant, 7.5 mmol KOH, 0.5 mL H2O were used.
[h]0.5 mol % Cat. (iii), 1 mmol reactant, 7.5 mmol KOH, 0.5 mL H2O were used.

In additional experiments, diethanolamine was used as the substrate, and the results are presented in Table 13:

TABLE 13

HOCH2CH2NHCH2CH2OH (a) →[Catalyst, H2O, NaOH]

TABLE 13-continued

[Structures shown: compound b (HO-CH2CH2-NH-CH2-C(=O)-ONa) and compound c (NaO-C(=O)-CH2-NH-CH2-C(=O)-ONa)]

| entry | Complex (mol %) | a (mmol) | base (mmol) | solvent (mL) | yield of b/% | yield of c/% |
|---|---|---|---|---|---|---|
| 1 | iii (0.2) | 2.5 | NaOH (10) | H₂O (0.5) dioxane (0.5) | >99 | — |
| 2 | 1 (0.2) | 2.5 | NaOH (10) | H₂O (0.5) dioxane (0.5) | >99 | — |
| 3 | iv (0.2) | 2.5 | NaOH (5.5) | H₂O (0.5) dioxane (0.5) | >99 | — |

Reaction conditions: Catalyst, diethanolamine, base, H₂O, dioxane, 125° C., reflux under Argon for 24 h. Yields determined by NMR.

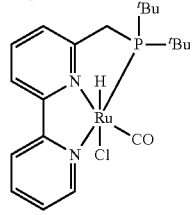

(iii)

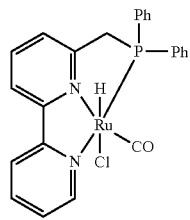

(iv)

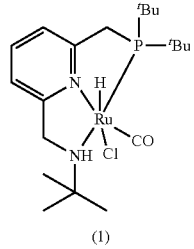

(1)

In conclusion, a highly efficient and simple method to produce α-, and β-amino acid salts directly from amino alcohols at low catalyst loadings through dehydrogenation in basic water was developed. No added oxidant is required, and the use of protection groups is avoided. Excellent yields of amino acid salts were generally obtained. In addition to the exemplified amino acids, many other important and useful natural and unnatural amino acid salts can be produced by applying this new method. In industry and laboratory, many α-amino acids, such as glycine and alanine, are usually produced through Strecker amino acid synthesis[18], of which highly toxic KCN or NaCN is needed. Importantly, the process of the present invention is atom-economical and environmentally friendly, as opposed to traditional methods, and the only by-product is hydrogen gas, which is useful by itself.

Example 10: Synthesis of Ruthenium Complexes and General Experimental Protocols

General Procedures:

All experiments with metal complexes and phosphine ligands were carried out under an atmosphere of purified nitrogen in a Vacuum Atmospheres glovebox equipped with a MO 40-2 inert gas purifier or using standard Schlenk techniques. All solvents were reagent grade or better. All non-deuterated solvents were refluxed over sodium/benzophenoneketyl and distilled under argon atmosphere. Deuterated solvents were used as received. All the solvents were degassed with argon and kept in the glovebox over 4 Å molecular sieves. Commercially available reagents were used as received. RuHCl(PPh₃)₃(CO) [Ahmad, N.; Levison, et al. *Inorganic Syntheses*; John Wiley & Sons, Inc.: (2007), p 45-64] and 2-(ClCH₂—)-6-('Bu₂P(BH₃)CH₂-)pyridine [Spasyuk, D.; Smith, S.; Gusev, D. G. *Angew. Chem. Int. Ed.* (2012), 51, 2772-2775]. were prepared according to literature procedures.

$^1$H, $^{13}$C and $^{31}$P NMR spectra were recorded at 400, 100, 162, and 376 MHz, respectively, using Bruker AMX-300, AMX-400 NMR and AMX-500 spectrometers. All spectra were recorded at 295 K, unless otherwise noted. $^1$H NMR and $^{13}$C{H} NMR chemical shifts are reported in ppm downfield from tetramethylsilane and referenced to the residual signals of an appropriate deuterated solvent. $^{31}$P{H} NMR chemical shifts are reported in ppm downfield from H₃PO₄ and referenced to an external 85% solution of phosphoric acid in D₂O.

ESI-MS spectroscopy was performed by the Department of Chemical Research Support, Weizmann Institute of Science. Complexes 1-3 and the PNNH ligands were stored at −34° C. in the dark. The abbreviation PNN stands for (6-((di-tert-butylphosphanyl)methyl)pyridin-2-yl)methanamine unit.

Accurate elemental analysis could not be obtained; HRMS was determined.

General Method for the Syntheses of PNNH Ligands (L1-L3)

A solution of 2-((BH₃)('Bu₂)PCH₂—)-6-((ClCH₂-)pyridine (1.0 g, 3.34 mmol) in excess of the respective amine (15.0 mL) was heated at 100° C. for 12 h in a J. Young Schlenk tube. It was then cooled to RT, evacuated under vacuum and refilled with N₂ and heating at 100° C. was continued for an additional 30 min. Excess solvent was then distilled out under high vacuum and the residue was extracted with pentane. The pentane solution was filtered through Celite and concentrated in vacuo to yield the corresponding BH₃-deprotected phosphine and amine substituted ligands as viscous pale yellow oils which solidified in the freezer (−30° C.).

Ligand 1: N-((6-((di-tert-butylphosphanyl)methyl)pyridin-2-yl)methyl)-2-methylpropan2-amine (L1)

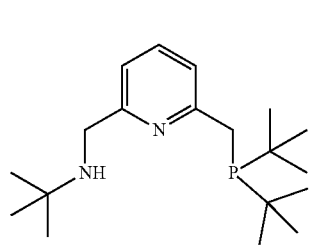

Yield: 97%, $^{31}P\{^{1}H\}$ NMR (CDCl$_3$): 36.5 (s).

$^{1}$H NMR (CDCl$_3$): 7.50 (t, $J_{H,H}$=7.6 Hz, 1H, Py-H4), 7.27 (d, $J_{H,H}$=7.6 Hz, 1H, Py-H5), 7.09 (d, $J_{H,H}$=7.6 Hz, 1H, Py-H3), 3.83 (bd, $J_{H,H}$=5.1 Hz, 2H, NHCH$_2$Py), 3.04 (d, $J_{H,P}$=3.6 Hz, 2H, PCH$_2$Py), 1.64 (bs, 1H, NH(CH$_3$)$_3$), 1.17 (bs, 18H, PC(CH$_3$)$_3$), 1.63 (bs, 9H, NH(CH$_3$)$_3$); $^{13}$C$\{^{1}$H$\}$ NMR (CDCl$_3$): 161.2 (m, Py-C2, C6) 136.5 (s, Py-C4), 121.8 (d, $J_{C,P}$=10.0 Hz, Py-C3), 118.8 (bm, Py-05), 48.6 (s, NHCH$_2$Py), 48.5 (s, NC(CH$_3$)$_3$), 31.9 (d, $J_{C,P}$=21.6 Hz, PC(CH$_3$)$_3$), 31.5 (d, $J_{C,P}$=23.8 Hz, PCH$_2$Py), 29.7 (d, $J_{C,P}$=13.0 Hz, PC(CH$_3$)$_3$), 29.2 (bs, NHC(CH$_3$)$_3$); HRMS: m/z 323.2619 (MH$^+$, calcd. m/z 323.2616).

Ligand 2: N-((6-((di-tert-butylphosphanyl)methyl)pyridin-2-yl)methyl)propan-2-amine (L2)

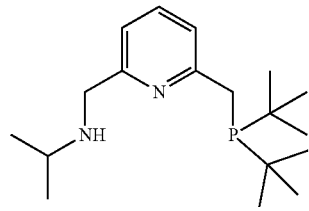

Yield: 80%, $^{31}P\{^{1}H\}$ NMR (CDCl$_3$): 35.4 (s).

$^{1}$H NMR (CDCl$_3$): 7.51 (t, $J_{H,H}$=7.6 Hz, 1H, Py-H4), 7.28 (d, $J_{H,H}$=7.6 Hz, 1H, Py-H5), 7.02 (d, $J_{H,H}$=7.6 Hz, 1H, Py-H3), 3.84 (bd, $J_{H,H}$=3.1 Hz, 2H, NHCH$_2$Py), 3.04 (d, $J_{H,P}$=3.6 Hz, 2H, PCH$_2$Py), 2.79 (sept, $J_{H,H}$=6.0 Hz, 1H, NH(CH$_3$)$_2$CH), 1.89 (bs, 1H, NH(CH$_3$)$_2$CH), 1.15 (bd, $J_{P,H}$=9.0 Hz, 18H, (CH$_3$)$_3$CPCH$_2$), 1.07 (d, 6H, NH(CH$_3$)$_2$CH); $^{13}$C$\{^{1}$H$\}$ NMR (CDCl$_3$): 161.2 (m, Py-C2, C6), 136.5 (s, Py-C4), 121.8 (d, $J_{C,P}$=10.0 Hz, Py-C3), 118.8 (bm, Py-05), 48.6 (s, NHCH$_2$Py), 48.5 (s, NC(CH$_3$)$_3$), 31.8 (d, $J_{C,P}$=21.6 Hz, PC(CH$_3$)$_3$), 31.5 (d, $J_{C,P}$=23.8 Hz, PCH$_2$Py), 29.7 (d, $J_{C,P}$=13.0 Hz, PC(CH$_3$)$_3$), 29.2 (bs, NHC(CH$_3$)$_2$). HRMS: m/z 308.2481 (MH$^+$, calcd. m/z 308.2381).

Ligand 3: N-benzyl-1-(6-((ditert-butylphosphanyl)methyl)pyridin-2-yl)methanamine (L3)

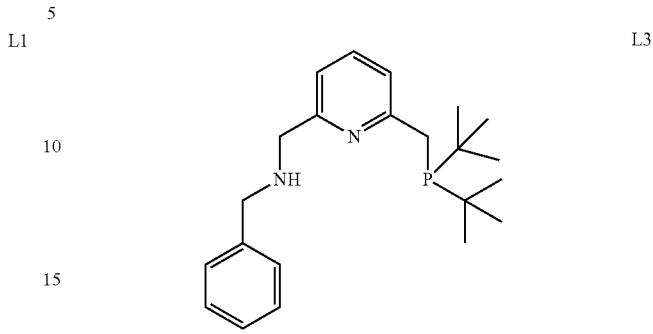

Yield: 79%, $^{31}P\{^{1}H\}$ NMR (CDCl$_3$): 37.0 (s).

$^{1}$H NMR (CDCl$_3$): 7.44 (t, $J_{H,H}$=7.5 Hz, 1H, Py-H4), 7.26-7.21 (m, 5H, Bn-arom.), 7.17 (d, $J_{H,H}$=7.5 Hz, 1H, Py-H5), 6.98 (d, $J_{H,H}$=7.5 Hz, 1H, Py-H3), 3.80 (bd, $J_{H,H}$=5.1 Hz, 2H, NHCH$_2$Py), 3.72 (bd, $J_{H,H}$=5.1 Hz, 2H, NHCH$_2$Bn), 2.97 (d, $J_{H,P}$=3.3 Hz, 2H, PCH$_2$Py), 2.13 (bs, 1H, NH(CH$_3$)), 1.09 (d, $J_{P,H}$=9.5 Hz, 18H, PC(CH$_3$)$_3$); $^{13}$C$\{^{1}$H$\}$ NMR (CD$_2$Cl$_2$): 161.7 (m, Py-C2, C6), 158.8 (s, Bn-arom-C1), 136.1 (s, Py-C4), 128.2 (s, Bn-arom-C4), 128.0 (s, Bn-arom-C2,C6), 126.7 (s, Bn-arom-C3,C5), 121.8 (d, $J_{C,P}$=10.0 Hz, Py-C3), 118.7 (s, Py-05), 54.3 (s, NHCH$_2$Py), 53.1 (s, NHCH$_2$Bn), 31.7 (d, $J_{C,P}$=23.8 Hz, PCH$_2$Py), 29.4 (d, $J_{C,P}$=13.0 Hz, PC(CH$_3$)$_3$), 26.6 (s, PC(CH$_3$)$_3$). HRMS: m/z 365.2120 (MNa$^+$, calcd. m/z 365.2122).

Synthesis of 1 (Ru(H)(Cl)(PNNH(t-butyl))(CO))

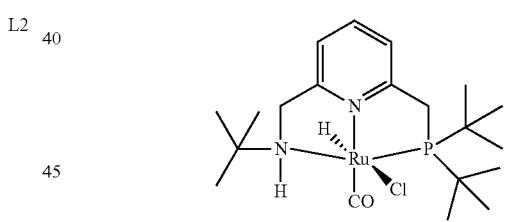

To a THF suspension (60.0 mL) of Ru(H)(Cl)(CO)(PPh$_3$)$_3$ (3.97 g, 4.16 mmol) was added 1.6 equiv. of ligand L1 (2.12 g, 6.66 mmol) under N$_2$ atmosphere and the reaction mixture was stirred at 65° C. for 4.0 h. The reaction mixture was allowed to cool to ambient temperature after which it was concentrated to approx. 25.0 mL under vacuum. Pentane was added to precipitate the product which was filtered and washed with ether to afford 1 (1.02 g) in 85% yield.

Crystals suitable for X-ray analysis were obtained by slow diffusion of pentane into a concentrated dichloromethane solution of 1.

$^{31}$P$\{^{1}$H$\}$ NMR (CD$_2$Cl$_2$): 109.2 (s); $^{1}$H NMR (CD$_2$Cl$_2$): 7.61 (bt, $J_{H,H}$=7.8 Hz, 1H, Py-H4), 7.31 (bd, $J_{H,H}$=7.6 Hz, 1H, Py-H5), 7.13 (d, $J_{H,H}$=8.0 Hz, 1H, Py-H3), 4.39 (m, 1H, NHCHHPy), 4.10 (dd, $J_{H,H}$=14.3 Hz, $J_{H,H}$=10.4 Hz, 2H, NHCHHPy), 3.63 (dd, $J_{H,P}$=16.6 Hz, $J_{H,H}$=8.1 Hz, 1H, PCHHPy), 3.42 (dd, $J_{H,P}$=16.6 Hz, $J_{H,H}$=11.1 Hz, 1H, PCHHPy), 1.60 (bs, 1H, NH(CH$_3$)), 1.40 (bm, 18H,

PC(CH$_3$)$_3$), 1.13 (d, J$_{H,P}$=13.3 Hz, 9H, NH(CH$_3$)), −15.85 (d, J$_{H,P}$=13.3 Hz, 1H, Ru—H); $^{13}$C{$^1$H} NMR (CD$_2$Cl$_2$): 208.6 (d, J$_{C,P}$=16.0 Hz, RuCO), 160.6 (d, J$_{C,P}$=4.4 Hz, Py-C2), 159.6 (s, Py-C6), 137.2 (s, Py-C4), 120.8 (d, J$_{C,P}$=9.0 Hz, Py-C3 118.8 (s, Py-5), 55.2 (s, NCCH$_3$), 54.9 (s, NHCH$_2$Py), 36.7 (d, J$_{C,P}$=10.3 Hz, PC(CH$_3$)$_3$), 36.5 (d, J$_{C,P}$=16.9 Hz, PCH$_2$Py), 36.4 (d, J$_{C,P}$=16.0 Hz, PC(CH$_3$)$_3$), 30.0 (d, J$_{C,P}$=3.9 Hz, PC(CH$_3$)$_3$)), 28.6 (bs, NHC(CH$_3$)$_3$), 28.3 (d, J$_{C,P}$=3.5 Hz, PC(CH$_3$)$_3$)); v(CO) 1896 cm$^{-1}$. HRMS: m/z 453.161 ([M−Cl]$^+$, calcd. m/z 453.1609).

Synthesis of 2 (Ru(H)(Cl)(PNNH(isopropyl))(CO))

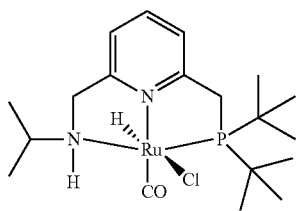

2

To a THF suspension (8.0 mL) of Ru(H)(Cl)(CO)(PPh$_3$)$_3$ (478.0 mg, 0.50 mmol) was added 1.5 equiv. of ligand L2 (232.0 mg, 0.75 mmol) under N$_2$ atmosphere and the reaction mixture was stirred at 65° C. for 4.0 h. It was brought to ambient temperature and the solvent was concentrated to one third of its volume. Pentane was added to precipitate the product which was filtered and washed with ether to afford complex 2 (212.0 mg) in 90.0% yield. Crystals suitable for X-ray analysis were obtained by slow diffusion of pentane into a concentrated CH$_2$Cl$_2$ solution of the complex.

$^{31}$P{$^1$H} NMR (CD$_2$Cl$_2$): 109.5 (s); $^1$H NMR (CD$_2$Cl$_2$): 7.61 (bt, J$_{H,H}$=7.8 Hz, 1H, Py-H4 7.31 (bd, J$_{H,H}$=9.0 Hz, 1H, Py-H5), 7.13 (d, J$_{H,H}$=9.0 Hz, 1H, Py-H3), 4.68 (bs, 1H, NH(CH$_3$)$_2$CH), 4.35 (m, 1H, NHCHHPy), 4.15 (dd, J$_{H,H}$=12.0, J$_{H,H}$=12.0 Hz, 2H, NHCHHPy), 3.63 (dd, J$_{H,P}$=12.0 Hz, J$_{H,H}$=8.9 Hz, 1H, PCHHPy), 3.42 (dd, J$_{H,P}$=16.6 Hz, J$_{H,H}$=11.1 Hz, 1H, PCHHPy), 3.03 (m, 1H, NH(CH$_3$)$_2$CH), 1.40 (d, 9H, J$_{H,P}$=13.4 Hz, PC(CH$_3$)$_3$, 1.35 (d, J$_{H,H}$=6.0 Hz, 3H, NH(CH$_3$)$_2$CH), 1.35 (d, J$_{H,H}$=6.1 Hz, 3H, NH(CH$_3$)$_2$CH), 1.16 (d, 9H, J$_{H,P}$=13.0 Hz, PC(CH$_3$)$_3$), −15.94 (d, J$_{H,P}$=23.3 Hz, 1H, Ru—H); $^{13}$C{$^1$H} NMR (CD$_2$Cl$_2$): 207.5 (d, J$_{C,P}$=16.8 Hz, RuCO), 160.3 (d, J$_{C,P}$=4.4 Hz, Py-C2 158.3 (s, Py-C6), 136.7 (s, Py-C4), 120.4 (d, J$_{C,P}$=9.0 Hz, Py-C3), 117.6 (s, Py-05), 58.08 (s, NHCH$_2$Py), 36.5 (d, J$_{C,P}$=8.5 Hz, PCH$_2$Py), 36.0 (d, J$_{C,P}$=12.3 Hz, PC(CH$_3$)$_3$), 29.4 (d, J$_{C,P}$=3.7 Hz, PC(CH$_3$)$_3$), 39.4 (d, J$_{C,P}$=3.9 Hz, PC(CH$_3$)$_3$, 27.8 (d, J$_{C,P}$=3.5 Hz, PC(CH$_3$)$_3$, 22.4 (s, (CH$_3$)$_2$CH)), 20.4 (s, (CH$_3$)$_2$CH)), IR: v(C—O) 1895 cm$^{-1}$. HRMS: m/z 439.1459 ([M−Cl]$^+$, calcd. m/z 439.1452).

Synthesis of 3 (Ru(H)(Cl)(PNNH(benzyl))(CO))

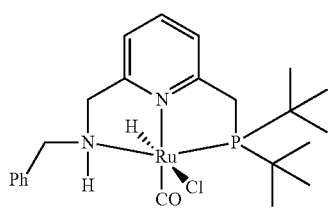

3

To a THF suspension (6.0 mL) of Ru(H)(Cl)(CO)(PPh$_3$)$_3$ (430.0 mg, 0.45 mmol) was added ligand L3 (256.0 mg, 0.72 mmol) under N$_2$ atmosphere and the reaction mixture was stirred at 65° C. for 4.0 h. It was brought to ambient temperature and the solvent was concentrated to one third of its volume. Pentane was added to precipitate the product which was filtered and washed with ether to afford complex 3 (200.0 mg) in 85% yield. Crystals suitable for X-ray analysis were obtained by slow diffusion of pentane into a concentrated CH$_2$Cl$_2$ solution of the complex.

$^{31}$P{$^1$H} NMR (CD$_2$Cl$_2$): 108.7 (s); $^1$H NMR (CD$_2$Cl$_2$): 7.61 (bt, J$_{H,H}$=7.8 Hz, 1H, Py-H4), 7.43-7.37 (m, 6H, overlapped Bn-H and Py-H5), 7.04 (d, J$_{H,H}$=7.0 Hz, 1H, Py-H3), 4.77 (bs, 1H, NH-Bn), 4.75 (bd, J$_{H,H}$=10.3 Hz, 1H, NHCHHPhenyl), 4.25 (d, J$_{H,H}$=15.0 Hz, 1H, NHCHHPy), 4.12 (t, J$_{H,H}$=11.6 Hz, 1H, NHCHHPhenyl), 4.00 (d, J$_{H,H}$=10.8 Hz, 1H, NHCHHPy), 3.67 (dd, J$_{H,P}$=15.6 Hz, J$_{H,H}$=7.5 Hz, 1H, PCHHPy), 3.51 (dd, J$_{H,P}$=12.6 Hz, J$_{H,H}$=7.5 Hz, 1H, PCHHPy), 1.45 (d, 9H, J$_{H,P}$=13.4 Hz, PC(CH$_3$)$_3$, 1.16 (d, 9H, J$_{H,H}$=13.0 Hz, PC(CH$_3$)$_3$, −15.55 (d, J$_{H,P}$=23.3 Hz, 1H, Ru—H); $^{13}$C{$^1$H} NMR (CD$_2$Cl$_2$): 209.1 (d, J$_{C,P}$=15.0 Hz, RuCO), 161.0 (d, J$_{C,P}$=4.7 Hz, Py-C2), 159.9 (s, Py-C6), 137.2 (s, Py-C4), 129.1 (s, Bn-arom-C2, C6), 128.8 (s, Bn-arom-C3,C5), 128.2 (s, Bn-arom.-C4), 121.0 (d, J$_{C,P}$=9.0 Hz, Py-C3), 118.8 (s, Py-05), 61.8 (s, CH$_2$Bn), 59.4 (s, NHCH$_2$Py), 36.7 (d, J$_{C,P}$=15.0 Hz, PCH$_2$Py), 36.5 (d, J$_{C,P}$=3.3 Hz, PC(CH$_3$)$_3$, 36.3 (d, J$_{C,P}$=3.3 Hz, PC(CH$_3$)$_3$, 30.1 (d, J$_{C,P}$=3.9 Hz, PC(CH$_3$)$_3$, 28.4 (d, J$_{C,P}$=3.5 Hz, PC(CH$_3$)$_3$. ESI (MS): 487.21 [M−Cl]$^+$; IR: v(C—O) 1907 cm$^{-1}$. HRMS: m/z 487.1458 ([M−Cl]$^+$, calcd. m/z 487.1452).

Synthesis of the anionic enamido complex 4' (Ru(H)(PNN(t-butyl))(CO)K$^+$)

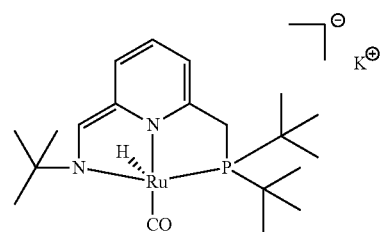

4'

To a suspension of the hydridochloride 1 (15.0 mg, 0.03 mmol) in dry THF-d8, was added KH (3.2 mg, 0.077 mmol) and solution was stirred for 18 h at RT in a J. Young NMR tube. The reaction mixture initially turns dark brown and later violet at which stage it was characterized in situ by NMR. The product was then filtered through a celite plug, concentrated and washed with ether. Crystals suitable for X-ray analysis can be obtained by slow diffusion of ether in concentrated solution of the complex in THF at RT.

Yield: 11.0 mg (73%). $^{31}$P{$^1$H} NMR (THF-d8): 124.1 (d, J$_{H,P}$=15.0 Hz); $^1$H NMR (THF-d8): 6.65 (bs, 1H, (t-butyl) NCHC—), 6.29 (bd, 1H, J$_{H,H}$=12.0 Hz, Py-05), 5.62 (bt, 1H, J$_{H,H}$=12.0 Hz, Py-C4), 5.08 (bs, 1H, Py-C3), 3.20 (dd, J$_{H,P}$=12.0 Hz, J$_{H,H}$=4.5 Hz, 1H, PCHHPy), 2.91 (dd, J$_{H,P}$=12.0 Hz, J$_{H,H}$=4.5 Hz, 1H, PCHHPy), 1.63 (s, 9H, (CH$_3$)$_3$N), 1.32 (d, 9H, J$_{H,P}$=12.0 Hz, PC(CH$_3$)$_3$, 1.16 (d, 9H, J$_{H,P}$=12.0 Hz, PC(CH$_3$)$_3$), −18.45 (d, 1H, J$_{H,P}$=28.0 Hz, Ru—H); $^{13}$C{$^1$H} NMR (THF-d8): 212.6 (bd, J$_{C,P}$=15.0 Hz, RuCO), 156.4 (s, Py-C6), 132.0 (s, Py-C2), 116.1 (s, Py-C4), 114.8 (s, (t-butyl)NCHC—), 114.6 (s, py-05), 92.0 (d, $J_{C,P}$=9.0 Hz, Py-C3 36.3 (s, (CH$_3$)$_3$CN), 32.5 (d, $J_{C,P}$=6.0 Hz, PC(CH$_3$)$_3$), 32.3 (d, $J_{C,P}$=6.0 Hz, PC(CH$_3$)$_3$), 34.2 (d, $J_{C,P}$=15.0 Hz, PCH$_2$Py), 33.5 (s, NC(CH$_3$)$_3$), 33.0 (s, NC(CH$_3$)$_3$), 28.4 (d, $J_{C,P}$=3.9 Hz, PC(CH$_3$)$_3$, 26.3 (d, $J_{C,P}$=3.5 Hz, PC(CH$_3$)$_3$). ES (MS) negative mode: 451.07 [M$^-$]; IR: ν(CO) 1907 cm$^{-1}$.

Catalytic Experiments—General Procedures

All the dehydrogenation experiments were carried out by the addition of the appropriate amounts of mentioned complex and base to the pure substrate in dry solvents. The mixture was then refluxed in a flask fitted with condenser with vigorous stirring under bubbling argon for the specified amount of time (open system). For reactions with diethyl ether as the solvent cold water circulation needed to be maintained throughout the reaction course. After the specified reaction time, a known quantity of an internal standard was added to the reaction mixture. It was then analyzed by GC for conversions and yields.

General Procedure for the Dehydrogenation of 2-Aminoethanol:

In a glove box, a 25 mL Schlenk flask was charged with a stirring bar, catalyst (0.005 mmol), KOtBu (0.006-0.012 mmol), 2-aminoethanol (1 mmol) and dioxane (4 mL) under an atmosphere of nitrogen. The flask was taken out of the glove box, equipped with a condenser and the solution was refluxed with stirring in an open system under a flow of argon for 12 h. After cooling to room temperature, 1 mmol of 1,3,5-trimethylbenzene was added to the crude reaction mixture as an internal standard. Then 0.05 mL of the solution was dissolved in CDCl$_3$ for determination of the conversion of 2-aminoethanol by $^1$H NMR spectroscopy. To the rest of the solution was added 10-15 mL hexane and the mixture was cooled down to 0° C. The formed precipitate was collected by simple filtration and washed with 10 mL of hexane and dried under vacuum. 1 mmol pyridine was then added to the dry solid as an internal standard and the mixture was analyzed by $^1$H NMR spectroscopy to determine the yield of glycine anhydride (GA), using D$_2$O as the solvent.

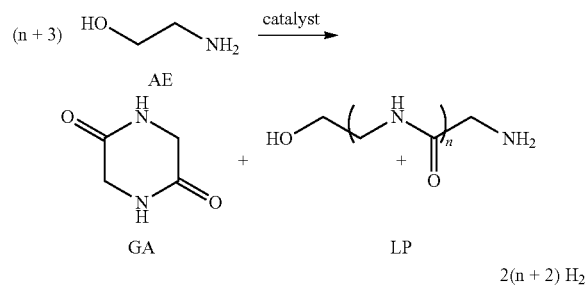

MS (ESI) of products obtained under conditions of Table 4 entry 4: 119.02 (linear peptide (n=1)+H), 141.03 (linear peptide (n=1)+Na), 198.05 (linear peptide (n=2)+Na), 233.06 (GA+linear peptide (n=1)+H), 255.13 (GA+linear peptide (n=1)+Na or linear peptide (n=3)+Na), 312.21 (linear peptide (n=4)+Na), 369.15 (linear peptide (n=5)+Na), 430.34 (linear peptide (n=6)+4H+Na), 453.17 (linear peptide (n=6)+4H+2Na). MS (CI): 112.93 (GA–H), 116.99 (linear peptide (n=1)–H), 174.01 (linear peptide (n=2)–H), 231.03 (GA+linear peptide (n=1)–H), 288.30 (linear peptide (n=4)–H), 402.25 (linear peptide (n=6)–H).

General Procedure for the Hydrogenation of Glycine Anhydride

In a glove box, a 100 mL Fischer-Porter tube or a 20 mL Parr apparatus was charged with catalyst (0.005 mmol), KOtBu (0.006-0.012 mmol), glycine anhydride (0.5-1.0 mmol) and dioxane or THF (2 or 4 mL) under an atmosphere of purified nitrogen. The pressure equipment was taken out of the glove box, and subjected to three successive cycles of pressurization/venting with H$_2$ (3 atm), then pressurized with H$_2$ (10-50 bar) and closed. The pressure equipment was placed behind a protective shield and the reaction mixture was heated in an oil bath at 110° C. with constant stirring for 24-48 h. After cooling to room temperature, excess H$_2$ was vented off carefully. The unreacted glycine anhydride was filtered off washed with 10 mL of hexane and dried under vacuum. To the dry solid was then added 1 mmol of pyridine as an internal standard, dissolved in D$_2$O for determination of the amount of glycine anhydride by $^1$H NMR spectroscopy The filtrate was collected and evaporated under vacuum to give a mixture. To the mixture was added 1 mmol of pyridine as an internal standard, dissolved in D$_2$O and analyzed by $^1$H NMR spectroscopy to determine the yield of 2-aminoethanol and the amount of glycine anhydride in solution. The total amount and the relative conversion of glycine anhydride were obtained in this way (the reason for this procedure is inaccurate determination of 2-aminoethanol in the presence of a large amount of glycine anhydride).

General Procedure for Transformation of Amino Alcohols to Amino Acid Salts:

In a glove box, a 25 mL Schlenk flask was charged with a stirring bar, catalyst (0.005-0.01 mmol), NaOH or KOH (5.5-10 mmol), amino alcohol (1-5 mmol), water (0.3-0.5 mL) and dioxane (0-0.5 mL) under an atmosphere of nitrogen (see Table 9 for specific amounts used). The flask was taken out of the glove box, equipped with a condenser and the solution was refluxed (oil bath temperature 125° C.) with stirring in an open system under a flow of argon for 24 h. After cooling to room temperature, 1-5 mmol of pyridine was added to the crude reaction mixture as an internal standard. 0-2 mL water was added, leading to a homogeneous solution. Then 0.05 mL of the solution was dissolved in D$_2$O for determination of the conversion of amino alcohol and the yield of amino acid salt by $^1$H NMR spectroscopy. Isolation of alanine is given as a specific example.

Isolation of Alanine:

The general procedure was followed using 0.1 mol % Cat. (iii), 5 mmol 2-aminopropanol, 10 mmol NaOH, 0.5 mL H$_2$O and 0.5 mL dioxane. The reaction was cooled to r.t. and the mixture was transferred to a 100 mL flask. 5 M HCl was added dropwise until the pH value was ca. 2. Then the solvent was evaporated, resulting in a brown residue. The brown residue was then refluxed with 200 mL methanol for 0.5 h and the resulting solution was filtered. The insoluble residue was extracted with hot methanol (3×100 mL) and the filtrates were combined. The solution was concentrated under vacuum and a light brown solid was obtained. The solid was washed with diethyl ether (3×15 mL) and dried, offering alanine as a light yellow solid in 71% yield.

N-Phth Protection of Alanine without Purification (Eq S1):

The brown residue obtained from the above procedure was mixed with phthalic anhydride (5.5 mmol), triethylamine (5.5 mmol) and toluene (50 mL). The mixture was refluxed overnight in a round bottom flask equipped with a Dean-Stark trap. The reaction was cooled to r.t. and the mixture was concentrated in vacuum to give the crude product, which was then dissolved in dichloromethane (DCM). To the DCM solution was added a concentrated aqueous HCl solution (37%, 1 mL). The mixture was washed with water and the organic layer was dried over Na$_2$SO$_4$. The solvent was removed under vacuum and the resulting solid was recrystallized from DCM/pentane (2/1 to 1/2 in v/v), resulting the N-Phth protected product in 82% yield.

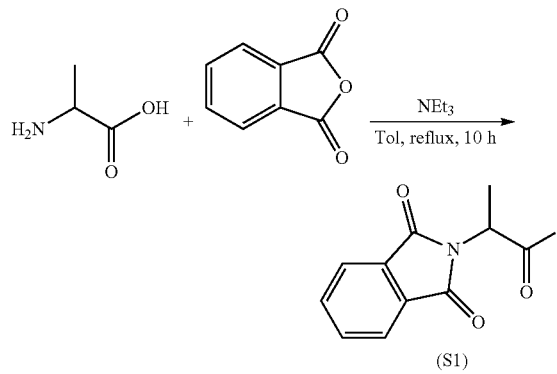

(S1)

Except for N-isopropylglycine and N-tert-butylglycine, the other amino acids or amino acid salts were reported in the literature and fully characterized.

N-isopropylglycine potassium salt:

$^1$H NMR (D$_2$O): 3.12 (2H, s), 2.78-2.69 (1H, m), 0.99 (6H, d, J=6.3 Hz); $^{13}$C{$^1$H} NMR (D$_2$O): 179.99, 49.87, 47.59, 21.32. HRMS calcd for C$_5$H$_{10}$K$_2$NO$_2$ [M+K]$^+$: 193.9986. found: 193.9985.

N-Tert-Butylglycine Potassium Salt:

$^1$H NMR (D$_2$O): 3.10 (2H, s), 1.04 (9H, s); $^{13}$C{$^1$H} NMR (D$_2$O): 180.10, 49.73, 45.78, 27.26. HRMS calcd for C$_6$H$_{12}$K$_2$NO$_2$+: 208.0142. found: 208.0144.

Example 11: Crystallographic Details

XRD Experimental Details of 1
Crystal Data:

C$_{20}$H$_{36}$N$_2$O$_1$P$_1$Cl$_1$Ru$_1$ yellow, 0.16×0.06×0.04 mm$^3$, Monoclinic, P2$_1$/c (N14), a=8.856(2), b=18.710(4), c=15.825(5) Å, β=120.92(2°) from 20 degrees of data, T=120(2) K, V=2249.5(10) Å$^3$, Z=4, Fw=488.00, Dc=1.441 Mg·m$^{-3}$, μ=0.898 mm$^{-1}$.

Data Collection and Processing:

Nonius KappaCCD diffractometer, MoKα (λ=0.71073 Å), graphite monochromator, 10136 reflections collected, −11≤h≤11, −24≤k≤24, −20≤l≤20, frame scan width=1°, scan speed 1.0° per 20 sec, typical peak mosaicity 0.47°, 5147 independent reflections (R-int=0.0226). The data were processed with Denzo-Scalepack.

Solution and Refinement:

Structure solved by direct methods with SHELXS-97. Full matrix least-squares refinement based on F$^2$ with SHELXL-97. 252 parameters with 0 restraints, final R$_1$=0.0417 (based on F$^2$) for data with I>2σ(I) and, R$_1$=0.0518 on 5147 reflections, goodness-of-fit on F$^2$=1.159, largest electron density peak=2.023 Å$^{-3}$, deepest hole −0.760 Å$^{-3}$.

XRD Experimental Details of 2
Crystal Data:

C$_{19}$H$_{34}$ClN$_2$OPRu, colourless needle, 0.30×0.10×0.04 mm$^3$, monoclinic P2(1)/n, a=8.7861(14)Å, b=18.177(2)Å, c=13.5212(18)Å, α=90 β=91.140(8°), γ=90 from 3931 reflections, T=100(2) K, V=2159.0(5)Å$^3$, Z=4, Fw=473.97, Dc=1.458 Mg·m$^{-3}$, μ=0.934 mm$^{-1}$.

Data Collection and Processing:

Bruker KappaApexll CCD diffractometer, MoKα (λ=0.71073 Å), graphite monochromator, MiraCol optics, −5≤h≤10, −22≤k≤20, −16≤l≤16, frame scan width=0.5°, scan speed 1.0° per 180 sec, typical peak mosaicity 0.62°, 10953 reflections collected, 4381 independent reflections (R-int=0.037). The data were processed with Bruker Apex2 Suite.

Solution and Refinement:

Structure solved with SHELXS-97. Full matrix least-squares refinement based on F$^2$ with SHELXL-97 on 241 parameters with 0 restraints gave final R$_1$=0.0292 (based on F$^2$) for data with I>2σ(I) and, R$_1$=0.0427 on 4381 reflections, goodness-of-fit on F$^2$=1.016, largest electron density peak 0.473 e·Å$^{-3}$. Largest hole −0717 e·Å$^{-3}$.

XRD Experimental Details of 3
Crystal Data:

C$_{23}$H$_{34}$O$_1$P$_1$N$_2$Cl$_1$Ru$_1$, colourless, 0.16×0.10×0.10 mm$^3$, Monoclinic, P2(1)/c, a=9.785(2)Å, b=10.694(2)Å, c=23.029(5)Å, β=93.83(3°) from 20 degrees of data, T=120(2)K, V=2404.4(8) Å$^3$, Z=4, Fw=522.01, Dc=1.442 Mg·m$^{-3}$, μ=0.846 mm$^{-1}$.

Data Collection and Processing:

Nonius KappaCCD diffractometer, MoKα (λ=0.71073 Å), graphite monochromator, 10258 reflections collected, −12≤h≤12, −13≤k≤13, −29≤l≤29, frame scan width=1°, scan speed 1° per 60 sec, typical peak mosaicity 0.48°, 5300 independent reflections (R-int=0.0399). The data were processed with Denzo-Scalepack.

Solution and Refinement:

Structure solved by direct methods with SHELXS-97. Full matrix least-squares refinement based on F$^2$ with SHELXL-97. 276 parameters with 1 restraint, final R$_1$=0.0459 (based on F$^2$) for data with I>2σ(I) and, R$_1$=0.0599 on 5300 reflections, goodness-of-fit on F$^2$=1.109, largest electron density peak=2.091 Å$^{-3}$, deepest hole −0.999 Å$^{-3}$.

XRD Experimental Details of 4
Crystal Data:

C$_{20}$H$_{34}$O$_1$P$_1$N$_2$K$_1$Ru$_1$, (C$_{20}$H$_{34}$O$_1$P$_1$N$_2$Ru$_1$+K$_1$) black, 0.17×0.05×0.05 mm$^3$, Monoclinic, P2(1)/c, a=14.4472(13) Å, b=24.334(2)Å, c=14.7244(11)Å, β=115.652(3°) from 20 degrees of data, T=100(2)K, V=4665.9(7) Å$^3$, Z=8, Fw=489.63, Dc=1.394 Mg·m$^{-3}$, μ=0.930 mm$^{-1}$.

Data Collection and Processing:

Bruker Apex2 KappaCCD diffractometer, MoKα (λ=0.71073 Å), graphite monochromator, 52954 reflections collected, −17≤h≤17, −29≤k≤22, −17≤l≤17, frame scan width=0.5°, scan speed 1° per 100 sec, typical peak mosaicity 0.69°, 8836 independent reflections (R-int=0.0564). The data were processed with Bruker Apex2 Suite.

Solution and Refinement:

Structure solved by direct methods with SHELXS-97. Full matrix least-squares refinement based on F$^2$ with SHELXL-97. 493 parameters with 0 restraints, final R$_1$=0.0418 (based on F$^2$) for data with I>2σ(I) and, R$_1$=0.0571 on 8836 reflections, goodness-of-fit on F$^2$=1.062, largest electron density peak=2.483 Å$^{-3}$, deepest hole −0.915 Å$^{-3}$.

TABLE 14

| | Selected bond distances/angles of 1-3 | | | | |
|---|---|---|---|---|---|
| 1 | Distances (Å) | 2 | Distances (Å) | 3 | Distances (Å) |
| Ru1—Cl1 | 2.562 (1) | Ru—Cl | 2.5623 (7) | Ru—Cl | 2.5536 (10) |
| Ru—H1A | 1.5126 (5) | Ru—H1A | 1.58 (3) | Ru—H1 | 1.853 (18) |
| Ru1—C20 | 1.841 (3) | Ru—C(19) | 1.839 (3) | Ru—C(23) | 1.826 (4) |
| Ru1—N1 | 2.109 (3) | Ru—N(1) | 2.107 (2) | Ru—N(1) | 2.100 (3) |
| Ru1—N2 | 2.234 (3) | Ru—N(2) | 2.200 (2) | Ru—N(2) | 2.182 (3) |
| Ru1—P1 | 2.2695 (9) | Ru—P1 | 2.2728 (7) | Ru—P1 | 2.2672 (9) |
| 1 | Angles (°) | 2 | Angles (°) | 3 | Angles (°) |
| N1—Ru—H1A | 90.70 | N1—Ru—H1A | 88.5 (10) | N1—Ru—H1 | 99.4 (14) |
| N2—Ru1—P1 | 157.96 (7) | N2—Ru—P1 | 157.36 (6) | N2—Ru—P1 | 160.18 (9) |
| N1—Ru1—C20 | 173.3 (1) | N1—Ru—C19 | 174.36 (10) | N1—Ru—C23 | 175.15 (13) |

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A Ruthenium complex represented by the structure of any of formulae A1, A2, A3 or A4:

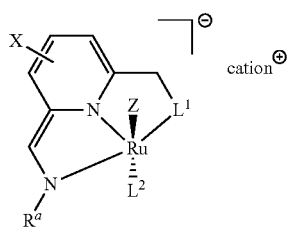

A1

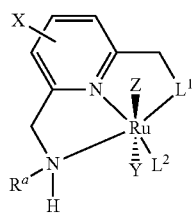

A2

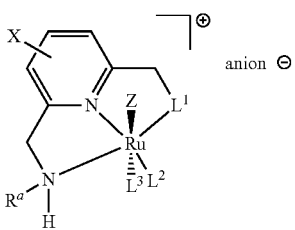

A3

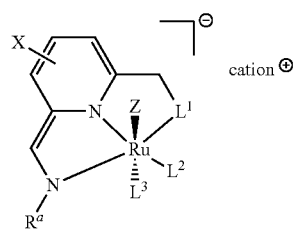

A4 wherein $L^1$ is selected from the group consisting of phosphine ($PR^bR^c$), phosphite $P(OR^b)(OR^c)$, phosphinite $P(OR^b)(R^c)$, amine ($NR^bR^c$), imine, oxazoline, sulfide ($SR^b$), sulfoxide ($S(=O)R^b$), heteroaryl containing at least one heteroatom selected from nitrogen and sulfur; arsine ($AsR^bR^c$), stibine ($SbR^bR^c$) and a N-heterocyclic carbene represented by the structures:

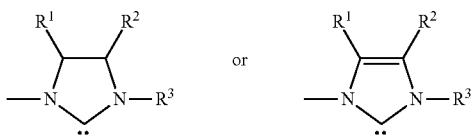

$L^2$ is a mono-dentate two-electron donor selected from the group consisting of CO, $PR^bR^cR^d$, $P(OR^b)(OR^c)(OR^d)$, $NO^+$, $AsR^bR^cR^d$, $SbR^bR^cR^d$, $SR^bR^c$, nitrile (RCN), isonitrile (RNC), $N_2$, $PF_3$, CS, heteroaryl, tetrahydrothiophene, alkene and alkyne;

$L^3$ is absent or is $L^2$;

Y and Z are each independently H or an anionic ligand selected from the group consisting of H, halogen, OCOR, $OCOCF_3$, $OSO_2R$, $OSO_2CF_3$, CN, OR, $N(R)_2$ and RS;

$R^a$ is H, alkyl, cycloalkyl, aryl, heterocyclyl, heteroaryl, alkylcycloalkyl, alkylaryl, alkylheterocyclyl or alkylheteroaryl;

$R^b$, $R^c$ and $R^d$ are each independently alkyl, cycloalkyl, aryl, heterocyclyl, heteroaryl, alkylcycloalkyl, alkylaryl, alkylheterocyclyl or alkylheteroaryl;

R, $R^1$, $R^2$ and $R^3$ are each independently H, alkyl, cycloalkyl, aryl, heterocyclyl, heteroaryl, alkylcycloalkyl, alkylaryl, alkylheterocyclyl or alkylheteroaryl;

X represents zero, one, two or three substituents independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety;

anion ⊖ represents a group bearing a single negative charge; and cation ⊕ represents a group bearing a single positive charge.

2. The complex of claim 1, wherein X represents zero substituents; $L^1$ is phosphine ($PR^bR^c$); $L^2$ is CO; and Z and Y are independently H or halogen.

3. The complex of claim 1, wherein Z of structure A1 is H, and the complex is represented by the structure A1':

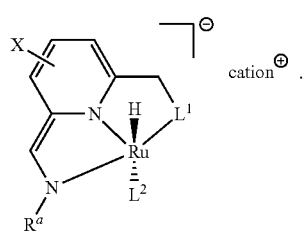

A1'

4. The complex of claim 1, which is represented by the structure of formula B1:

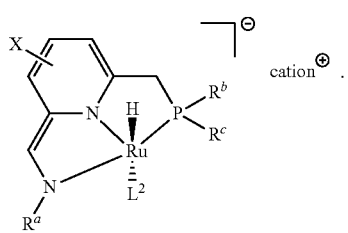

B1

5. The complex of claim 4, wherein $L^2$ is CO; Ra is selected from the group consisting of H, alkyl, cycloalkyl, aryl, alkylaryl, heterocyclyl and heteroaryl; and Rb and Rc are each independently selected from the group consisting of alkyl, cycloalkyl, aryl, alkylaryl, heterocyclyl and heteroaryl.

6. The complex of claim 4, which is represented by the structure of formula 4:

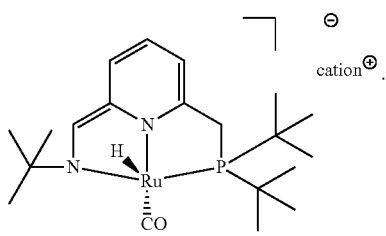

4

7. The complex of claim 1, wherein the structure of formula A2 is represented by the structure of formula B2:

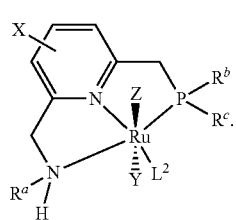

B2

8. The complex of claim 7, which is represented by the structure of formula 1, 2 or 3:

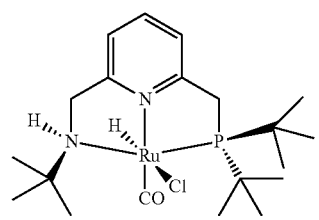

1

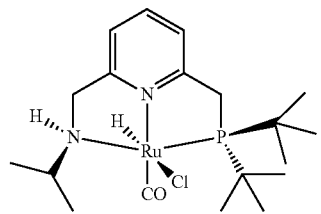

2

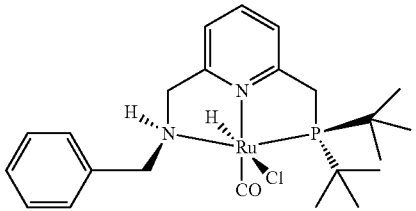

3

9. A process for preparing an ester by dehydrogenative coupling of alcohols, comprising the step of reacting an alcohol or a combination of alcohols in the presence of a Ruthenium complex as a catalyst, thereby generating the ester and molecular hydrogen; or a process of hydrogenating an ester, comprising the step of reacting the ester with molecular hydrogen ($H_2$) in the presence a Ruthenium complex as a catalyst, thereby hydrogenating the ester; wherein the Ruthenium complex is a Ruthenium complex according to claim 1.

10. The process of claim 9, which is selected from the group consisting of:
(i) a process comprising the step of converting a primary alcohol represented by formula $R^4CH_2OH$ to an ester by the structure $R^4-C(=O)-OCH_2R^4$:

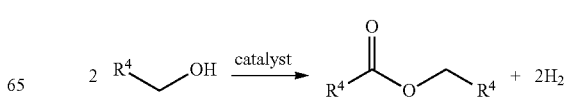

wherein R⁴ is selected from the group consisting of H, an unsubstituted or substituted alkyl, alkoxyalkyl, haloalkyl, cycloalkyl, aryl, alkylaryl, heterocyclyl and heteroaryl;

(ii) a process comprising the step of reacting a first primary alcohol represented by formula R⁴CH₂OH with a second primary alcohol represented by formula R⁴'CH₂OH so as to generate an ester by the structure R⁴—C(=O)—OCH₂R⁴' or an ester of formula R⁴'—C(=O)—OCH₂R⁴

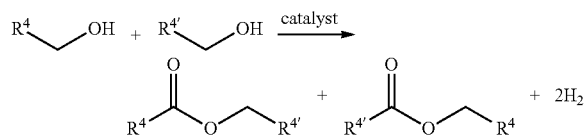

wherein R⁴ and R⁴' are each independently selected is from the group consisting of H, an unsubstituted or substituted alkyl, alkoxyalkyl, haloalkyl, cycloalkyl, aryl, alkylaryl, heterocyclyl and heteroaryl; and (iii) a process comprising the step of reacting a primary alcohol represented by formula R⁴CH₂OH with a secondary alcohol of formula R⁴'R⁴''CHOH so as to generate an ester by the structure R⁴—C(=O)—OCHR⁴'R⁴'':

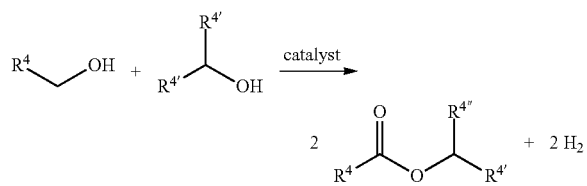

wherein R⁴, R⁴' and R⁴'' are each independently selected from the group consisting of H, an unsubstituted or substituted alkyl, alkoxyalkyl, haloalkyl, cycloalkyl, aryl, alkylaryl, heterocyclyl and heteroaryl.

11. The process of claim 9, wherein the alcohol is selected from the group consisting of methanol, ethanol, n-propanol, iso-propanol, n-butanol, isobutanol, t-butanol, n-pentanol, 2-pentanol, 3-pentanol, 1-hexanol, 2-hexanol, 3-hexanol, 2-methoxyethanol, 2,2,2-trifluoroethanol, 2-methyl-1-butanol, 3-methyl-1-butanol, benzyl alcohol, 2-methoxy benzyl alcohol, 3-methoxy benzyl alcohol, 4-methoxy benzyl alcohol, 1-phenylethanol, and cyclohexane methanol; or
wherein the alcohol is a dialcohol, and the process results in a polyester or a lactone.

12. The process of claim 9, comprising the step of hydrogenating an ester represented by the formula R⁵C(=O)—OR⁶ to the corresponding alcohol or alcohols:

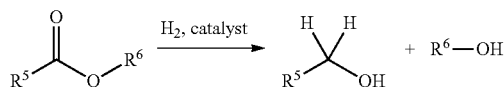

wherein
R⁵ is selected from the group consisting of H, an unsubstituted or substituted alkyl, alkoxyalkyl, cycloalkyl, aryl, alkylaryl, heterocyclyl and heteroaryl; and R⁶ is selected from the group consisting of an unsubstituted or substituted alkyl, alkoxyalkyl, cycloalkyl, aryl, alkylaryl, heterocyclyl and heteroaryl.

13. The process of claim 9, wherein R⁵ is H and the process comprises hydrogenating a formate ester of formula H—C(=O)—OR⁶ to methanol and an alcohol of formula R⁶—OH.

14. The process of claim 9, wherein the ester is selected from the group consisting of hexyl hexanoate, methyl hexanoate, cyclohexyl hexanoate, tert-butyl acetate, cyclohexyl acetate, 2,2,2-trifluoroethyl 2,2,2-trifluoroacetate, benzyl benzoate, ethyl 3-phenylpropanoate, ethyl benzoate, butyl butyrate, methyl formate, ethyl formate, propyl formate butyl formate, methyl trifluoroacetate, methyl difluoroacetate and methyl monofluoroacetate; or
wherein the ester is a cyclic ester (lactone), or
wherein the ester is a cyclic di-ester (di-lactone), and the process results in the formation of a diol.

15. A process for preparing an amide, comprising the step of reacting a primary or secondary amine with a primary alcohol in the presence of the Ruthenium complex according to as a catalyst, thereby generating the amide and molecular hydrogen; or a process for hydrogenating an amide to an alcohol and an amine, comprising the step of reacting the amide with molecular hydrogen (H₂) in the presence of the Ruthenium complex as a catalyst, thereby generating the amine and alcohol; wherein the Ruthenium complex is a Ruthenium complex according to claim 1.

16. The process of claim 15, comprising the step of reacting an amine represented by formula R⁷R⁷'NH with an alcohol represented by the formula R⁸CH₂OH to generate an amide represented by the structure R⁸—C(=O)—NR⁷R⁷':

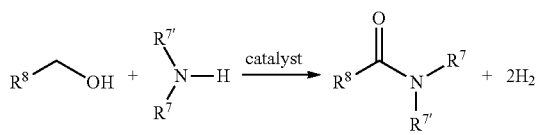

wherein R⁷, R⁷' and R⁸ are each independently selected from the group consisting of H an unsubstituted or substituted alkyl, alkoxyalkyl, cycloalkyl, aryl, alkylaryl, heterocyclyl and heteroaryl; or R⁷ and R⁷' are joined to form a ring together with the nitrogen.

17. The process of claim 15, wherein (a) the amine is a diamine or the alcohol is a dialcohol, and the process results in a diamide; or (b) the amine is a diamine and the alcohol is a dialcohol, and the process results in a polyamide; or (c) the amine and alcohol are present in the same molecule, and the process is an intra-molecular process which results in a lactam; or (d) the amine and the alcohol are present in the same molecule, and the process is an inter-molecular process which results in a polyamide; or (e) the amine and alcohol together represent a beta-amino alcohol, and the process results in a polypeptide; or (f) the amine and alcohol together represent a beta-amino alcohol, and the process is an intra-molecular process which results in a cyclic dipeptide.

18. The process of claim 17, wherein said amide is prepared by reacting ethylenediamine (ED) with ethanol in the presence of said Ruthenium catalyst, to generate N,N'-diacetylethylenediamine (DAE)

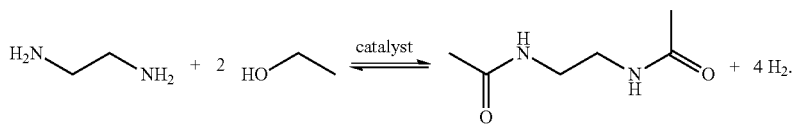

19. The process of claim 15, wherein the amine and alcohol together represent a beta-amino alcohol, and the process is an inter-molecular process which results in a polypeptide, an intra-molecular process which results in a cyclic dipeptide, or a combination thereof:

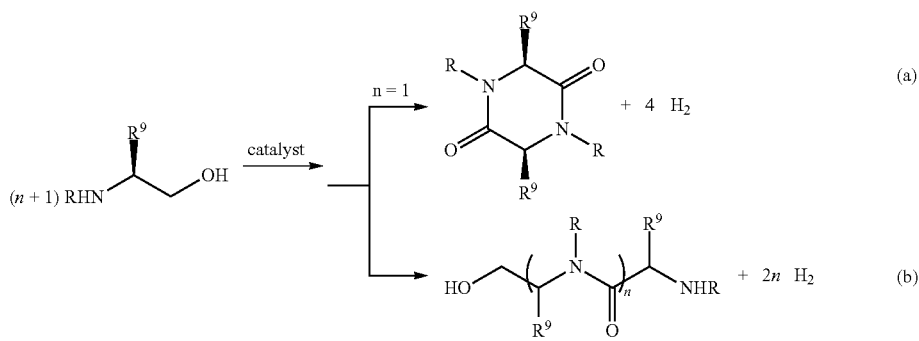

wherein R is H or alkyl;
$R^9$ is selected from the group consisting of H an unsubstituted or substituted alkyl, cycloalkyl, aryl, alkylaryl, heterocyclyl and heteroaryl; and
n is 1 to 20;
wherein the process optionally results in a mixture of (i) glycine anhydride or N,N-dimethyl GA; and (ii) a linear peptide represented by the structure:

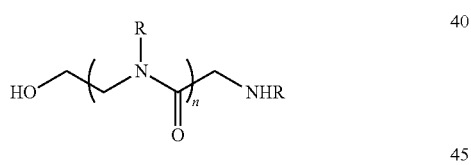

wherein R is H or $CH_3$, and n is an integer of 1 to 20.

20. The process of claim 15, comprising the step of hydrogenating an amide represented by the formula $R^{10}C(=O)-N-R^{11}R^{11'}$ to an alcohol of formula $R^{10}CH_2OH$ and amine of formula $R^{11}R^{11'}NH$:

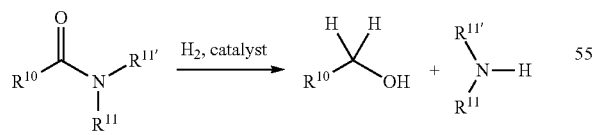

wherein $R^{10}$, $R^{11}$ and $R^{11'}$ are each independently selected from the group consisting of H, an unsubstituted or substituted alkyl, alkoxyalkyl, cycloalkyl, aryl, alkylaryl, heterocyclyl and heteroaryl.

21. The process of claim 15, wherein said amide is N,N-diacetylethylenediamine (DAE), and said N,N'-diacetylethylenediamine (DAE) is hydrogenated to generate ethylenediamine (ED) and ethanol

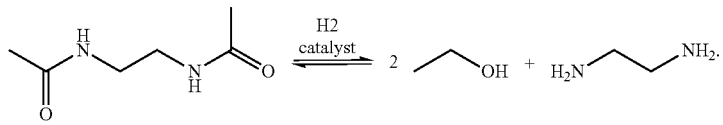

22. The process of claim 15 wherein the amide is selected from the group consisting of N-benzyl-2-methoxyacetamide, N-hexyl-2-methoxyacetamide, N-hexyl-3-methyloxetane-3-carboxamide, N-hexyl-2-furanylcarboxamide, N-benzylbenzamide, N-ethylacetamide, N-methylpropionamide, N-cyclohexyl-2-methoxyacetamide, N-phenylacetamide, N-phenylhexylamide, 2-methoxy-N-phenylacetamide, N-phenylbenzamide, Ethylenediamine-N,N'-(2-methoxyacetamide), N-hexanoylmorpholine, N-butanoylmorpholine, N-2-metoxyacetylpyrrolidine, N-formylmorpholine, N,N-dimethylformamide, N,N-diethylbenzamide, benzamide, 4-methylbenzamide, cyclohexanecarboxamide, hexanamide, acetamide, acrylamide and pivalamide; or
  the amide is a cyclic amide (lactam) and the process results in an amino alcohol.

23. A process for hydrogenating an organic carbonate, carbamate or urea derivative, comprising the step of reacting the organic carbonate, carbamate or urea derivative with molecular hydrogen ($H_2$) in the presence of the Ruthenium complex according to claim 1 as a catalyst, thereby hydrogenating the organic carbonate, carbamate or urea derivative and generating at least one alcohol, amine or combination thereof.

24. The process of claim 23, which is selected from the group consisting of:
  (i) a process comprising the step of hydrogenating a carbonate represented by the formula $R^{12}O—C(=O)—OR^{12'}$ to the corresponding alcohols(s) and methanol:

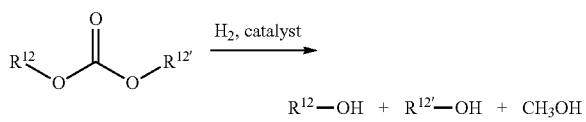

wherein $R^{12}$ and $R^{12'}$ are the same or different and are selected from the group consisting of an unsubstituted or substituted alkyl, alkoxyalkyl, cycloalkyl, aryl, alkylaryl, heterocyclyl and heteroaryl;
  (ii) a process comprising the step of hydrogenating a carbamate represented by the formula $R^{13}O—C(=O)—NHR^{14}$ to the corresponding amine, alcohol and methanol:

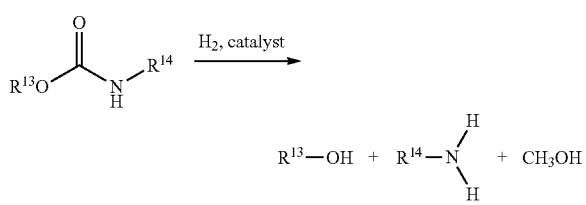

wherein $R^{13}$ is selected from the group consisting of an unsubstituted or substituted alkyl, alkoxyalkyl, cycloalkyl, aryl, alkylaryl, heterocyclyl and heteroaryl; and $R^{14}$ is selected from the group consisting of H or an unsubstituted or substituted alkyl, alkoxyalkyl, cycloalkyl, aryl, alkylaryl, heterocyclyl and heteroaryl; and
  (iii) a process comprising the step of hydrogenating a urea derivative to the corresponding amine and methanol:

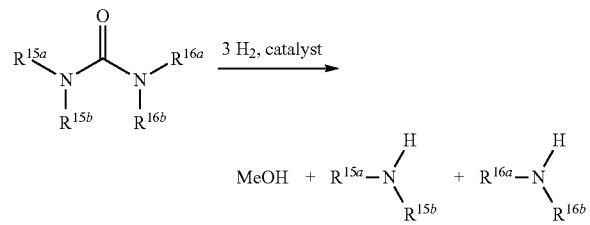

wherein each of $R^{15a}$ and $R^{16a}$, which may be the same or different, is selected from the group consisting of H, an unsubstituted or substituted alkyl, alkoxyalkyl, cycloalkyl, aryl, alkylaryl, and heterocyclyl, and each of $R^{15b}$ and $R^{16b}$, which may be the same or different, is selected from the group consisting of H, an unsubstituted or substituted alkyl, alkoxyalkyl, cycloalkyl, aryl, alkylaryl, and heterocyclyl; or wherein at least one of $R^{15a}$ and $R^{15b}$, and/or $R^{16a}$ and $R^{16b}$ together with the nitrogen to which they are attached form a heterocyclic ring.

25. The process of claim 24 wherein the carbonate is a polycarbonate, or wherein the carbamate is a polycarbamate or wherein the urea derivative is a polyurea derivative.

26. A process for preparing a ketone by dehydrogenation of a secondary alcohol, comprising the step of reacting the secondary alcohol in the presence of the Ruthenium complex according to claim 1 as a catalyst, thereby generating the ketone and molecular hydrogen.

27. The process of claim 26, comprising the step of converting a secondary alcohol represented by formula $R^{17}CH(OH)R^{17'}$ to a ketone represented by the structure $R^{17}—C(=O)—R^{17'}$:

wherein $R^{17}$ and $R^{17'}$ are each independently selected from the group consisting of H or an unsubstituted or substituted alkyl, alkoxyalkyl, cycloalkyl, aryl, alkylaryl, heterocyclyl and heteroaryl.

28. A process for preparing an amide, comprising the step of reacting a primary or secondary amine with an ester in the presence of the Ruthenium complex according to claim 1 as a catalyst, thereby generating the amide and molecular hydrogen.

29. The process of claim 28, comprising the step of reacting an amine represented by formula $R^{18}R^{18'}NH$ with an ester represented by the formula $R^{19}$—C(=O)—OCH$_2$R$^{19'}$ to generate an amide represented by the structure $R^{19}$—C(=O)—NR$^{18}$R$^{18'}$ or $R^{19'}$—C(=O)—NR$^{18}$R$^{18'}$:

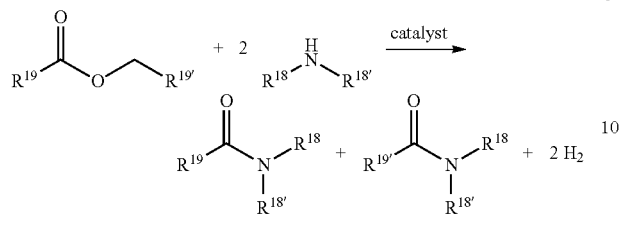

wherein $R^{18}$, $R^{18'}$, $R^{19}$ and $R^{19'}$ are each independently selected from the group consisting of H an unsubstituted or substituted alkyl, alkoxyalkyl, cycloalkyl, aryl, alkylaryl, heterocyclyl and heteroaryl.

30. A process for preparing an ester by reacting a primary or secondary alcohol with an ester in the presence of the Ruthenium complex according to claim 1 as a catalyst, thereby generating the ester and molecular hydrogen.

31. The process of claim 30, comprising the step of reacting a primary or secondary alcohol represented by formula $R^{21}R^{21'}$CHOH with an ester by the structure $R^{20}$—C(=O)—OCH$_2$R$^{20'}$:

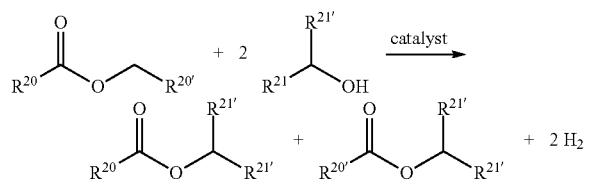

wherein $R^{20}$, $R^{20'}$, $R^{21}$ and $R^{21'}$ are each independently selected from the group consisting of H, an unsubstituted or substituted alkyl, alkoxyalkyl, cycloalkyl, aryl, alkylaryl, heterocyclyl and heteroaryl.

32. A process for preparing a carboxylic acid comprising the step of reacting a primary alcohol with water and a base in the presence of the Ruthenium complex according to claim 1 as a catalyst, thereby generating the carboxylic acid and molecular hydrogen.

33. The process of claim 32, comprising the step of reacting a primary alcohol represented by formula $R^{22}$CH$_2$OH with water in the presence of a base so as to generate a carboxylic acid salt represented by the structure $R^{22}$—C(=O)O$^-$ and, optionally, if desired, converting the carboxylic acid salt to the corresponding carboxylic acid of formula $R^{22}$—C(=O)OH:

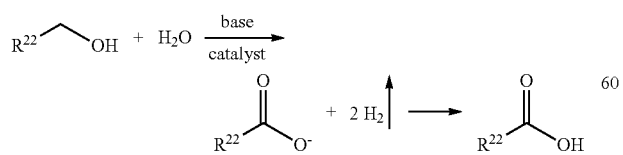

wherein $R^{22}$ is selected from the group consisting of H, an unsubstituted or substituted alkyl, aminoalkyl, alkoxyalkyl, cycloalkyl, aryl, alkylaryl, heterocyclyl and heteroaryl.

34. A process for preparing an amino acid or a salt thereof, by contacting an amino alcohol with the Ruthenium complex according to claim 1 as a catalyst, in the presence of water and a base, under conditions sufficient to generate the amino acid or a salt thereof.

35. The process of claim 34, wherein the amino alcohol is a β- or γ-amino alcohol and the reaction is represented by the scheme:

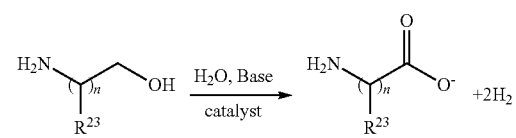

wherein $R^{23}$ is H or an unsubstituted or substituted alkyl; and n is 1 or 2.

36. The process of claim 34, wherein the amino alcohol is selected from the group consisting of 2-aminoethanol (ethanolamine), 2-amino-1-butanol, diethanolamine, 2-aminopropanol, N-methylethanolamine, N,N-dimethylethanolamine, N-isopropylethanolamine, t-tert-butylethanolamine, 2-amino-3-methyl-1-butanol, prolinol, 2-amino-3-phenyl-1-propanol, 2-amino-2-phenyl-1-ethanol, 3-aminopropanol, N,N-dimethyl-3-aminopropanol, 3-amino-3-phenyl-1-propanol, and 2-aminobenzyl alcohol, or salts of any of the foregoing.

37. The process of claim 34, wherein the resultant amino acid is selected from the group consisting of glycine, α-aminobutyric acid, 2-(2-hydroxyethylamino)acetic acid, alanine, sarcosine, dimethylglycine, N-isopropyl glycine, N-tert-butyl glycine, leucine, proline, phenylalanine, 2-phenylglycine, β-alanine, N,N-dimethyl-β-alanine, 3-amino-3-phenyl propanoic acid, and anthranilic acid, or salts of any of the foregoing.

38. A process selected from the group consisting of:
(i) a process for preparing a Ruthenium complex represented by the structure of formula A1 of claim 1, the process comprising the step of reacting a Ruthenium complex of formula A2 of claim 1, in the presence of at least two equivalents of a base:

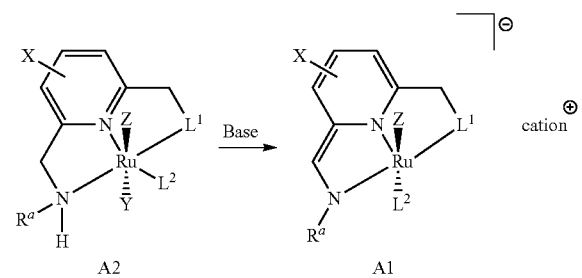

wherein $L^1$, $L^2$, X, Y, Z and $R^a$ are as defined in claim 1;

(ii) a process for preparing a Ruthenium complex represented by the structure of formula A4 of claim 1, the process comprising the step of reacting a Ruthenium complex of formula A3 of claim 1, in the presence of at least two equivalents of a base:

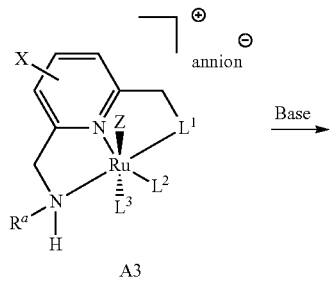

A3 wherein $L^1$, $L^2$, $L^2$, Y, Z and $R^a$ are as defined in claim 1; and (iii) a process for preparing a Ruthenium complex represented by the structure of formula A2 of claim 1, the process comprising the steps of reacting a precursor of formula B with a Ruthenium reagent represented by the structure $Ru(Z)(Y)(L^2)(P(Ar)_3)$ wherein Ar is phenyl or an alkyl-substituted phenyl.

39. The process of claim 14, wherein the cyclic ester is oxepan-2-one and the diol formed is hexane 1,6-diol; the cyclic di-ester is biomass-derived; the cyclic di-ester is glycolide or lactide; or the ester is a polyester.

40. The process of claim 19, wherein $R^9$ is H or methyl, and the process is conducted in the presence of a solvent; or wherein the beta-amino alcohol is ethanolamine or 2-(methylamino) ethanol, and the process results in glycine anhydride (GA) or N,N-dimethyl GA:

R = H, CH₃

41. The process of claim 22, wherein the cyclic amide is glycine anhydride (GA) or N,N-dimethyl GA and the process results in ethanolamine or 2-(methylamino) ethanol:

wherein R is H or CH₃; or the amide is a polyamide, or the amide is a polypeptide.

42. The process of claim 38, wherein said process (i) further comprises the step of preparing a Ruthenium complex represented by the structure of formula 4 from a precursor of formula 1 or
said process (iii) further comprises the step of reacting a precursor of formula B' with Ru(H)Cl(CO)(PPh₃) to generate a compound of formula 1, 2 or 3:
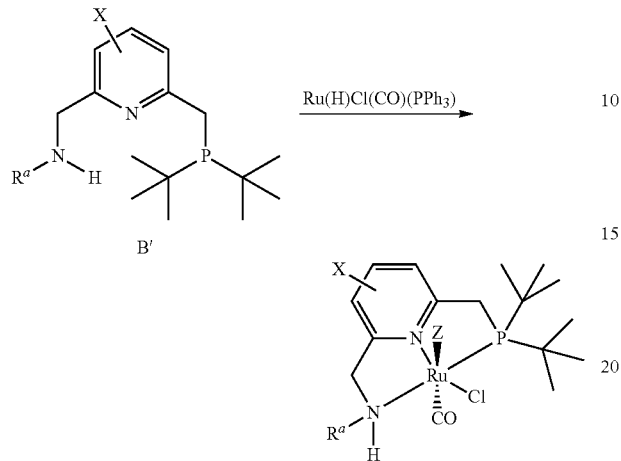
wherein $R^a$ is t-butyl (compound 1), isopropyl (compound 2) or benzyl (compound 3).
* * * * *